(12) United States Patent
Wang et al.

(10) Patent No.: US 12,281,082 B2
(45) Date of Patent: Apr. 22, 2025

(54) ELECTROLUMINESCENT MATERIAL AND DEVICE

(71) Applicant: BEIJING SUMMER SPROUT TECHNOLOGY CO., LTD., Beijing (CN)

(72) Inventors: Qiang Wang, Beijing (CN); Le Wang, Beijing (CN); Junfei Wang, Beijing (CN); Han Zhang, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 766 days.

(21) Appl. No.: 17/336,941

(22) Filed: Jun. 2, 2021

(65) Prior Publication Data

US 2022/0289681 A1 Sep. 15, 2022

(30) Foreign Application Priority Data

Jun. 5, 2020 (CN) .......................... 202010505906.4
Apr. 28, 2021 (CN) .......................... 202110464197.4

(51) Int. Cl.
*C07D 223/32* (2006.01)
*C07D 405/14* (2006.01)
(Continued)

(52) U.S. Cl.
CPC ......... *C07D 223/32* (2013.01); *C07D 405/14* (2013.01); *C09K 11/06* (2013.01);
(Continued)

(58) Field of Classification Search
CPC .... C07D 223/32; C07D 405/14; C09K 11/06; C09K 2211/1029; H10K 85/654;
(Continued)

(56) References Cited

U.S. PATENT DOCUMENTS

| | | | |
|---|---|---|---|
| 5,703,436 | A | 12/1997 | Forrest et al. |
| 5,707,745 | A | 1/1998 | Forrest et al. |

(Continued)

FOREIGN PATENT DOCUMENTS

| | | |
|---|---|---|
| CN | 107431136 | 12/2017 |
| CN | 108391433 | 8/2018 |

(Continued)

OTHER PUBLICATIONS

Chinese First Office Action for Chinese Application No. 202110464197.4, dated Oct. 31, 2022, 20 pages with translation.

(Continued)

*Primary Examiner* — Ruiyun Zhang
(74) *Attorney, Agent, or Firm* — Workman Nydegger

(57) ABSTRACT

Disclosed are an electroluminescent material and device. The compound is a compound formed by connecting an indole- and pyrrole-fused azamacrocycle to triazine or a similar structure thereof at a specific position and is used as the host material of the electroluminescent device. These novel compounds have significantly reduced evaporation temperature and better thermal stability, can effectively reduce energy consumption, which more facilitates the device manufacturing process, and in addition, can also effectively improve device efficiency and reduce device drive voltage, which can provide better device performance. Further disclosed are an electroluminescent device, a compound formulation, and a display assembly.

25 Claims, 2 Drawing Sheets

(51) Int. Cl.
  *C09K 11/06* (2006.01)
  *H10K 85/30* (2023.01)
  *H10K 85/60* (2023.01)
  *H10K 50/11* (2023.01)

(52) U.S. Cl.
  CPC ......... *H10K 85/342* (2023.02); *H10K 85/654* (2023.02); *H10K 85/6572* (2023.02); *H10K 85/6574* (2023.02); *H10K 85/6576* (2023.02); *C09K 2211/1029* (2013.01); *H10K 50/11* (2023.02)

(58) Field of Classification Search
  CPC ........... H10K 85/6572; H10K 85/6574; H10K 85/6576; H10K 50/11
  USPC .................................. 257/40; 428/690, 917
  See application file for complete search history.

(56) References Cited

U.S. PATENT DOCUMENTS

| | | | |
|---|---|---|---|
| 5,844,363 | A | 12/1998 | Gu et al. |
| 6,097,147 | A | 8/2000 | Baldo et al. |
| 6,303,238 | B1 | 10/2001 | Thompson et al. |
| 7,279,704 | B2 | 10/2007 | Walters et al. |
| 7,968,146 | B2 | 6/2011 | Wagner et al. |
| 2003/0230980 | A1 | 12/2003 | Forrest et al. |
| 2004/0174116 | A1 | 9/2004 | Lu et al. |
| 2015/0349273 | A1 | 12/2015 | Hung et al. |
| 2016/0359122 | A1 | 12/2016 | Boudreault et al. |
| 2018/0337340 | A1 | 11/2018 | Moon |

FOREIGN PATENT DOCUMENTS

| | | | | |
|---|---|---|---|---|
| CN | 111269239 | | 6/2020 | |
| CN | 111269239 | A * | 6/2020 | ........... C07D 487/16 |
| CN | 112876489 | A | 6/2021 | |
| CN | 113527315 | A | 10/2021 | |
| CN | 113527316 | A | 10/2021 | |
| CN | 113527317 | A | 10/2021 | |
| CN | 114437134 | | 5/2022 | |
| JP | 2021176839 | | 11/2021 | |
| KR | 20150077220 | | 7/2015 | |
| KR | 20150077220 | A * | 7/2015 | |
| KR | 20170066241 | A | 6/2017 | |
| KR | 20170132493 | A | 12/2017 | |
| KR | 101926771 | | 12/2018 | |
| KR | 20210031409 | | 3/2021 | |
| WO | 2016158540 | | 10/2016 | |
| WO | 2017095156 | | 6/2017 | |
| WO | 2019177407 | | 9/2019 | |
| WO | 2019194599 | | 10/2019 | |

OTHER PUBLICATIONS

Japanese Notice of Reasons for Refusal for Japanese Application No. 2021-093959, dated Sep. 28, 2022, 47 pages with English translation.
German Office Action for Application No. 10 2021 114 330.6, dated Nov. 3, 2021, 9 pages with translation.
Uoyama, Hiroki, et al., "Highly efficient organic light—emitting diodes from delayed fluorescence", Nature, vol. 492, Dec. 13, 2012.
Tang, C.W., et al., "Orgnaic electroluminescent diodes", Applied Physics Letters, 1987 (accepted for publication Jul. 20, 1987).
Chinese Notice to Grant for Chinese Application No. 202110464197.4, dated Jul. 28, 2023, 3 pages with English translation.
Chinese Second Office Action for Chinese Application No. 202110464197.4, dated Feb. 22, 2023, 16 pages withEnglish translation.
Korean Notice of Final Rejection for Korean Application No. 10-2021-0072713, dated Sep. 26, 2023, 7 pages with English translation.
Korean Written Opinion for Korean Application No. 10-2021-0072713 dated Feb. 28, 2023, 16 pages with English translation.
Korean Written Decision on Registration for Korean Application No. 10-2021-0072713 dated Feb. 29, 2024, 16 pages with English translation.
Japanese Decision to Grant for Japanese Application No. 2021-093959, dated Mar. 28, 2023, 5 pages with English translation.
Germany Second Office Action for German Application No. 10 2021 114 330.6, dated Apr. 23, 2024, 16 pages with English Translation.

* cited by examiner

ELECTROLUMINESCENT MATERIAL AND DEVICE

CROSS-REFERENCE TO RELATED APPLICATION(S)

This application claims priority to Chinese Patent Application No. CN202010505906.4, filed on Jun. 5, 2020, and Chinese Patent Application No. CN202110464197.4, filed on Apr. 28, 2021, the disclosures of which are incorporated herein by reference in their entireties.

TECHNICAL FIELD

The present disclosure relates to compounds for organic electronic devices such as organic light-emitting devices. More particularly, the present disclosure relates to a compound formed by connecting an indole- and pyrrole-fused azamacrocycle to triazine or a similar structure thereof at a specific position, and an organic electroluminescent device and a compound formulation comprising the compound.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This device laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. A small molecule refers to any organic or organometallic material that is not a polymer. The molecular weight of the small molecule can be large as long as it has well defined structure. Dendrimers with well-defined structures are considered as small molecules. Polymer OLEDs include conjugated polymers and non-conjugated polymers with pendant emitting groups. Small molecule OLED can become the polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

KR1020150077220A discloses an organic electroluminescent compound having an organic optical compound of the following structure:

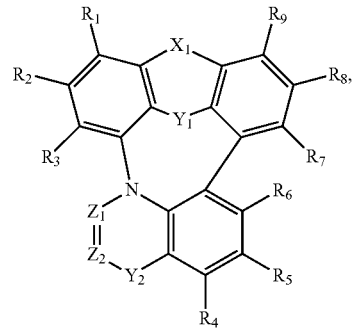

and the $X_1$ of the general formula disclosed therein may be $N(Ar_1)$. However, this disclosure does not disclose or teach the application of connecting an indole- and pyrrole-fused azamacrocyclic structure to triazine or a similar structure thereof through specific connecting structures.

US20180337340A1 discloses an organic electroluminescent compound and an organic electroluminescent device comprising the same, wherein the organic electroluminescent device includes an organic layer containing one or more hosts, wherein a first host is an organic optical compound having the following structure:

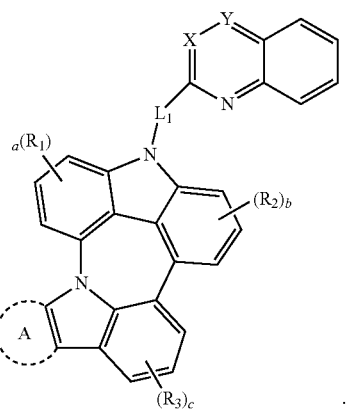

However, the compound disclosed by this disclosure is required to include a structure unit of quinazoline or quinoxaline and bond to the 2-position of quinazoline or quinoxaline, and this disclosure does not disclose or teach the organic compound formed by connecting an indole fused azamacrocyclic structure unit to a structure unit of triazine or a similar structure thereof through specific connecting structures.

However, various host materials reported so far still need to be improved. In order to meet the increasing requirements of the industry, especially requirements for higher device efficiency, longer device life, and lower driving voltage performance, a novel material still needs to be further researched and developed.

SUMMARY

The present disclosure aims to provide a series of compounds formed by connecting an indole- and pyrrole-fused azamacrocycle to triazine or a similar structure thereof at a specific position to solve at least part of the above problems. These compounds can be used as the host material in organic electroluminescent devices. These novel compounds have significantly reduced evaporation temperature and better thermal stability, can effectively reduce energy consumption, which more facilitates the device manufacturing process, and in addition, can also effectively improve device efficiency and reduce device driving voltage, which can provide better device performance.

According to an embodiment of the present disclosure, disclosed is a compound having a structure of H-L-E, wherein H has a structure represented by Formula 1:

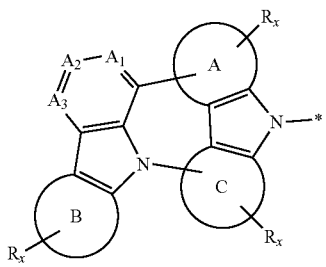

Formula 1 wherein, in Formula 1, $A_1$, $A_2$, and $A_3$ are, at each occurrence identically or differently, selected from N or CR, and the ring A, the ring B, and the ring C are, at each occurrence identically or differently, selected from a carbocyclic ring having 5 to 18 carbon atoms or a heterocyclic ring having 3 to 18 carbon atoms;

$R_x$ represents, at each occurrence identically or differently, mono-substitution, multiple substitutions, or non-substitution;

E has a structure represented by Formula 2:

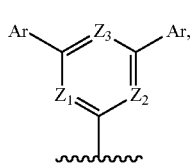

Formula 2 in Formula 2, Ar is, at each occurrence identically or differently, selected from substituted or unsubstituted aryl having 6 to 30 carbon atoms or substituted or unsubstituted heteroaryl having 3 to 30 carbon atoms;

$Z_1$ to $Z_3$ are each independently selected from N or $CR_z$, and at least one of $Z_1$ to $Z_3$ is N;

L has a structure represented by Formula 3:

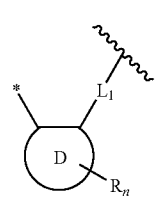

Formula 3 in Formula 3, the ring D is, at each occurrence identically or differently, selected from a carbocyclic ring having 5 to 18 carbon atoms or a heterocyclic ring having 3 to 18 carbon atoms;

$R_n$ represents, at each occurrence identically or differently, mono-substitution, multiple substitutions, or non-substitution;

$L_1$ is selected from a single bond, substituted or unsubstituted arylene having 6 to 30 carbon atoms, substituted or unsubstituted heteroarylene having 3 to 30 carbon atoms, or combinations thereof; and when $L_1$ is selected from substituted arylene having 6 to 30 carbon atoms or substituted heteroarylene having 3 to 30 carbon atoms, $L_1$ has a substituent $R_m$; and $R_m$ represents, at each occurrence identically or differently, mono-substitution or multiple substitutions;

R, $R_x$, $R_z$, $R_n$, and $R_m$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents R, $R_x$ can be optionally joined to form a ring;

adjacent substituents $R_n$, $R_m$ can be optionally joined to form a ring.

According to another embodiment of the present disclosure, further disclosed is an electroluminescent device including an anode, a cathode, and an organic layer disposed between the anode and the cathode, wherein the organic layer includes a compound having a structure of H-L-E;

wherein H has a structure represented by Formula 1:

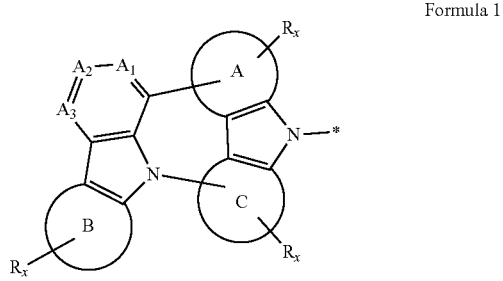

Formula 1 in Formula 1, $A_1$, $A_2$, and $A_3$ are, at each occurrence identically or differently, selected from N or CR, and the ring A, the ring B, and the ring C are, at each occurrence identically or differently, selected from a carbocyclic ring having 5 to 18 carbon atoms or a heterocyclic ring having 3 to 18 carbon atoms;

$R_x$ represents, at each occurrence identically or differently, mono-substitution, multiple substitutions, or non-substitution;

E has a structure represented by Formula 2:

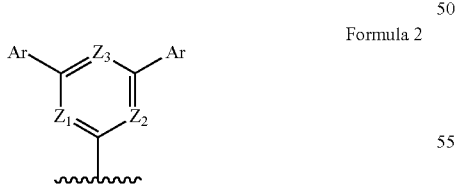

Formula 2 in Formula 2, Ar is, at each occurrence identically or differently, selected from substituted or unsubstituted aryl having 6 to 30 carbon atoms or substituted or unsubstituted heteroaryl having 3 to 30 carbon atoms;

$Z_1$ to $Z_3$ are each independently selected from N or $CR_z$, and at least one of $Z_1$ to $Z_3$ is N;

L has a structure represented by Formula 3:

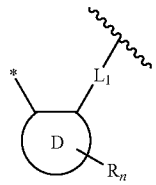

Formula 3 in Formula 3, the ring D is, at each occurrence identically or differently, selected from a carbocyclic ring having 5 to 18 carbon atoms or a heterocyclic ring having 3 to 18 carbon atoms;

$R_n$ represents, at each occurrence identically or differently, mono-substitution, multiple substitutions, or non-substitution;

$L_1$ is selected from a single bond, substituted or unsubstituted arylene having 6 to 30 carbon atoms, substituted or unsubstituted heteroarylene having 3 to 30 carbon atoms, or combinations thereof; and when $L_1$ is selected from substituted arylene having 6 to 30 carbon atoms or substituted heteroarylene having 3 to 30 carbon atoms, $L_1$ has a substituent $R_m$; and $R_m$ represents, at each occurrence identically or differently, mono-substitution or multiple substitutions;

R, $R_x$, $R_z$, $R_n$, and $R_m$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents R, $R_x$ can be optionally joined to form a ring;

adjacent substituents $R_n$, $R_m$ can be optionally joined to form a ring.

According to another embodiment of the present disclosure, further disclosed is a compound formulation comprising the compound having a structure of H-L-E.

According to another embodiment of the present disclosure, further disclosed is a display assembly comprising the organic electroluminescent device that includes the compound having a structure of H-L-E in an organic layer.

The novel compound disclosed by the present disclosure, which is formed by connecting an indole- and pyrrole-fused azamacrocycle to triazine or a similar structure thereof at a specific position, can be used as the host material of the electroluminescent device. These novel compounds have an electron transporting unit based on triazine or a similar structure thereof and a hole transporting unit based on an indole- and pyrrole-fused azamacrocyclic structure, wherein the electron transporting unit is connected to the hole transporting unit at a specific position. Such a molecular structure design of connecting the hole transporting unit and the electron transporting unit at a specific position enables the molecules of these compounds to have special spatial structures, which brings unexpected effects, so that such a novel compound has significantly reduced evaporation temperature and better thermal stability, can effectively reduce energy consumption, which more facilitates the device manufacturing process, and in addition, can also effectively improve device efficiency, which can provide better device performance.

DETAILED DESCRIPTION

Figure 1:
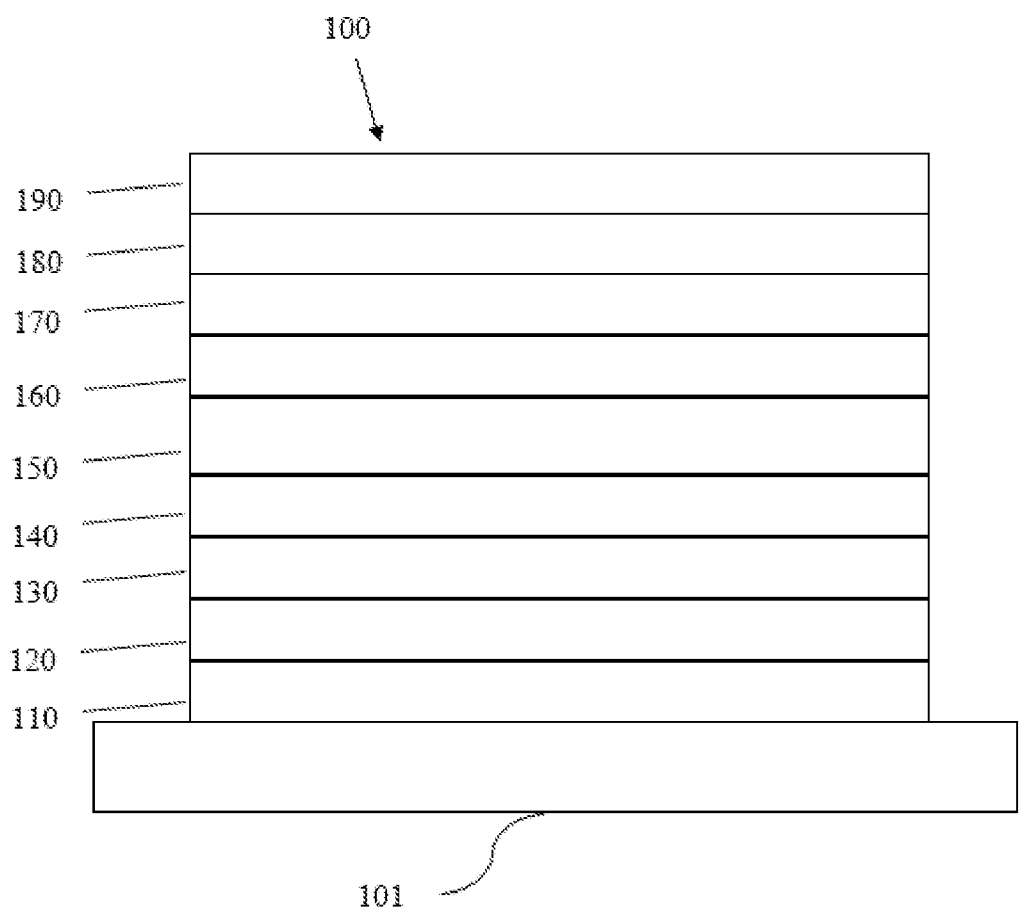
FIG. 1 is a schematic diagram of an organic light-emitting apparatus that may include a compound and a compound formulation disclosed by the present disclosure.

OLEDs can be fabricated on various types of substrates such as glass, plastic, and metal foil. FIG. 1 schematically shows an organic light emitting device 100 without limitation. The figures are not necessarily drawn to scale. Some of the layers in the figures can also be omitted as needed. Device 100 may include a substrate 101, an anode 110, a hole injection layer 120, a hole transporting layer 130, an electron blocking layer 140, an emissive layer 150, a hole blocking layer 160, an electron transporting layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transporting layer is m-MTDATA doped with $F_4$-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transporting layer is BPhen doped with $L_1$ at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties.

Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting examples. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
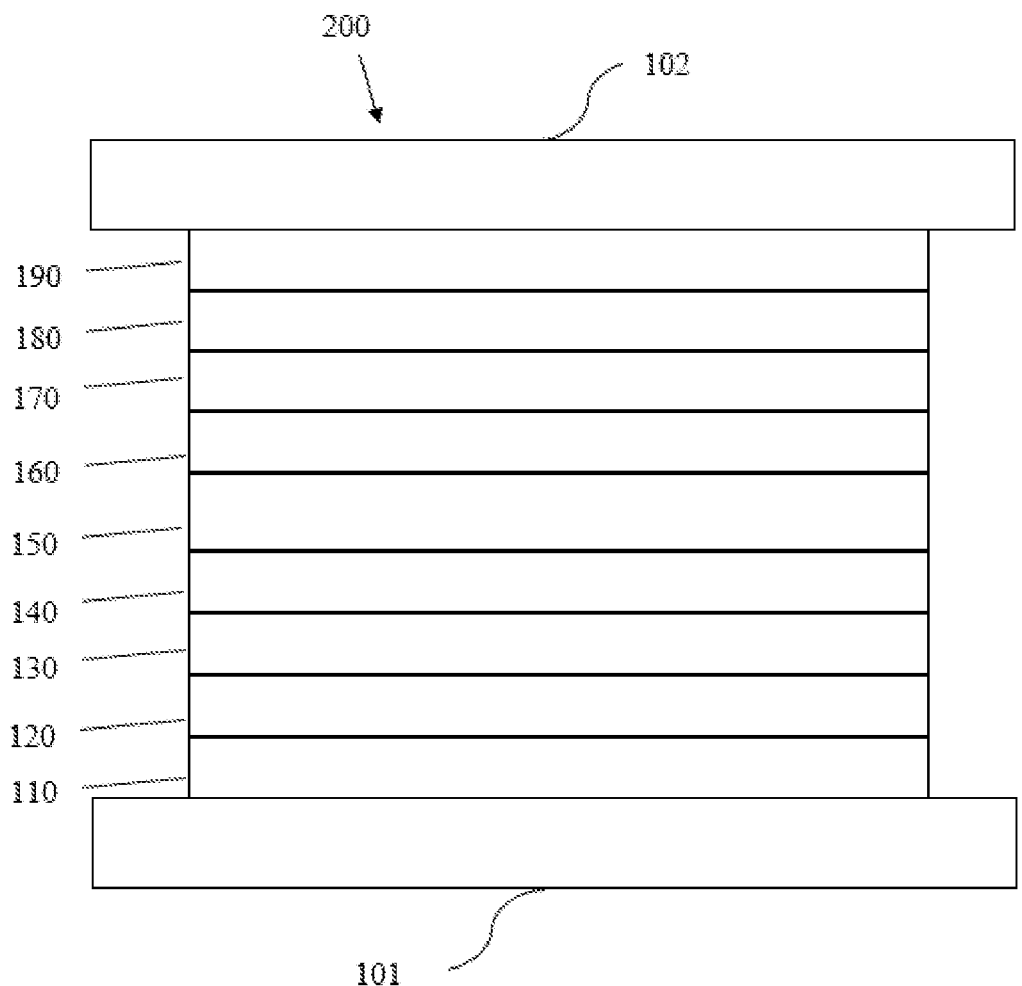
FIG. 2 is a schematic diagram of another organic light-emitting apparatus that may include a compound and a compound formulation disclosed by the present disclosure.

An OLED can be encapsulated by a barrier layer. FIG. 2 schematically shows an organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass or organic-inorganic hybrid layers. The barrier layer should be placed directly or indirectly outside of the OLED device. Multilayer thin film encapsulation was described in U.S. Pat. No. 7,968,146, which is incorporated by reference herein in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from the substrate. There may be other layers between the first and second layers, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is generally characterized as a donor-acceptor charge-transfer (CT) type emission. The spatial separation of the HOMO and LUMO in these donor-acceptor type compounds generally results in small $\Delta E_{S-T}$. These states may involve CT states. Generally, donor-acceptor luminescent materials are constructed by connecting an electron donor moiety such as amino- or carbazole-derivatives and an electron acceptor moiety such as N-containing six-membered aromatic rings.

DEFINITION OF TERMS OF SUBSTITUENTS

Halogen or halide—as used herein includes fluorine, chlorine, bromine, and iodine.

Alkyl—as used herein includes both straight and branched chain alkyl groups. Alkyl may be alkyl having 1 to 20 carbon atoms, preferably alkyl having 1 to 12 carbon atoms, and more preferably alkyl having 1 to 6 carbon atoms. Examples of alkyl groups include a methyl group, an ethyl group, a propyl group, an isopropyl group, a n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group. Additionally, the alkyl may be optionally substituted. Of the above, preferred are a methyl group, an ethyl group, a propyl group, an isopropyl group, a n-butyl group, an s-butyl group, an isobutyl group, a t-butyl group, an n-pentyl group, a neopentyl group, and an n-hexyl group. Additionally, the alkyl group may be optionally substituted.

Cycloalkyl—as used herein includes cyclic alkyl groups. The cycloalkyl groups may be those having 3 to 20 ring carbon atoms, preferably those having 4 to 10 carbon atoms.

Examples of cycloalkyl include cyclobutyl, cyclopentyl, cyclohexyl, 4-methylcyclohexyl, 4,4-dimethylcylcohexyl, 1-adamantyl, 2-adamantyl, 1-norbornyl, 2-norbornyl, and the like. Of the above, preferred are cyclopentyl, cyclohexyl, 4-methylcyclohexyl, and 4,4-dimethylcylcohexyl. Additionally, the cycloalkyl group may be optionally substituted.

Heteroalkyl—as used herein, includes a group formed by replacing one or more carbons in an alkyl chain with a hetero-atom(s) selected from the group consisting of a nitrogen atom, an oxygen atom, a sulfur atom, a selenium atom, a phosphorus atom, a silicon atom, a germanium atom, and a boron atom. Heteroalkyl may be those having 1 to 20 carbon atoms, preferably those having 1 to 10 carbon atoms, and more preferably those having 1 to 6 carbon atoms. Examples of heteroalkyl include methoxymethyl, ethoxymethyl, ethoxyethyl, methylthiomethyl, ethylthiomethyl, ethylthioethyl, methoxymethoxymethyl, ethoxymethoxymethyl, ethoxyethoxyethyl, hydroxymethyl, hydroxyethyl, hydroxypropyl, mercaptomethyl, mercaptoethyl, mercaptopropyl, aminomethyl, aminoethyl, aminopropyl, dimethylaminomethyl, trimethylsilyl, dimethylethylsilyl, dimethylisopropylsilyl, t-butyldimethylsilyl, triethylsilyl, triisopropylsilyl, trimethylsilylmethyl, trimethylsilylethyl, and trimethylsilylisopropyl. Additionally, the heteroalkyl group may be optionally substituted.

Alkenyl—as used herein includes straight chain, branched chain, and cyclic alkene groups. Alkenyl may be those having 2 to 20 carbon atoms, preferably those having 2 to 10 carbon atoms. Examples of alkenyl include vinyl, propenyl, 1-butenyl, 2-butenyl, 3-butenyl, 1,3-butandienyl, 1-methylvinyl, styryl, 2,2-diphenylvinyl, 1,2-diphenylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl, 3-phenyl-1-butenyl, cyclopentenyl, cyclopentadienyl, cyclohexenyl, cycloheptenyl, cycloheptatrienyl, cyclooctenyl, cyclooctatetraenyl, and norbornenyl. Additionally, the alkenyl group may be optionally substituted.

Alkynyl—as used herein includes straight chain alkynyl groups. Alkynyl may be those having 2 to 20 carbon atoms, preferably those having 2 to 10 carbon atoms. Examples of alkynyl groups include ethynyl, propynyl, propargyl, 1-butynyl, 2-butynyl, 3-butynyl, 1-pentynyl, 2-pentynyl, 3,3-dimethyl-1-butynyl, 3-ethyl-3-methyl-1-pentynyl, 3,3-diisopropyl-1-pentynyl, phenylethynyl, phenylpropynyl, etc. Of the above, preferred are ethynyl, propynyl, propargyl, 1-butynyl, 2-butynyl, 3-butynyl, 1-pentynyl, and phenylethynyl. Additionally, the alkynyl group may be optionally substituted.

Aryl or an aromatic group—as used herein includes non-condensed and condensed systems. Aryl may be those having 6 to 30 carbon atoms, preferably those having 6 to 20 carbon atoms, and more preferably those having 6 to 12 carbon atoms. Examples of aryl groups include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl may be optionally substituted. Examples of non-condensed aryl groups include phenyl, biphenyl-2-yl, biphenyl-3-yl, biphenyl-4-yl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-(2-phenylpropyl)phenyl, 4'-methylbiphenylyl, 4"-t-butyl-p-terphenyl-4-yl, o-cumenyl, m-cumenyl, p-cumenyl, 2,3-xylyl, 3,4-xylyl, 2,5-xylyl, mesityl, and m-quarterphenyl. Additionally, the aryl group may be optionally substituted.

Heterocyclic groups or heterocyclic ring—as used herein include non-aromatic cyclic groups. Non-aromatic heterocyclic groups include saturated heterocyclic groups having 3 to 20 ring atoms and unsaturated non-aromatic heterocyclic groups having 3 to 20 ring atoms, where at least one ring atom is selected from the group consisting of a nitrogen atom, an oxygen atom, a sulfur atom, a selenium atom, a silicon atom, a phosphorus atom, a germanium atom, and a boron atom. Preferred non-aromatic heterocyclic groups are those having 3 to 7 ring atoms, each of which includes at least one hetero-atom such as nitrogen, oxygen, silicon, or sulfur. Examples of non-aromatic heterocyclic groups include oxiranyl, oxetanyl, tetrahydrofuranyl, tetrahydropyranyl, dioxolanyl, dioxanyl, aziridinyl, dihydropyrrolyl, tetrahydropyrrolyl, piperidinyl, oxazolidinyl, morpholinyl, piperazinyl, oxepinyl, thiepinyl, azepinyl, and tetrahydrosilolyl. Additionally, the heterocyclic group may be optionally substituted.

Heteroaryl—as used herein, includes non-condensed and condensed hetero-aromatic groups having 1 to 5 hetero-atoms, wherein at least one hetero-atom is selected from the group consisting of a nitrogen atom, an oxygen atom, a sulfur atom, a selenium atom, a silicon atom, a phosphorus atom, a germanium atom, and a boron atom. A hetero-aromatic group is also referred to as heteroaryl. Heteroaryl may be those having 3 to 30 carbon atoms, preferably those having 3 to 20 carbon atoms, and more preferably those having 3 to 12 carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridoindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indenoazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—as used herein, is represented by —O-alkyl, —O-cycloalkyl, —O-heteroalkyl, or —O-heterocyclic group. Examples and preferred examples of alkyl, cycloalkyl, heteroalkyl, and heterocyclic groups are the same as those described above. Alkoxy groups may be those having 1 to 20 carbon atoms, preferably those having 1 to 6 carbon atoms. Examples of alkoxy groups include methoxy, ethoxy, propoxy, butoxy, pentyloxy, hexyloxy, cyclopropyloxy, cyclobutyloxy, cyclopentyloxy, cyclohexyloxy, tetrahydrofuranyloxy, tetrahydropyranyloxy, methoxypropyloxy, ethoxyethyloxy, methoxymethyloxy, and ethoxymethyloxy. Additionally, the alkoxy group may be optionally substituted.

Aryloxy—as used herein, is represented by —O-aryl or —O-heteroaryl. Examples and preferred examples of aryl and heteroaryl are the same as those described above. Aryloxy groups may be those having 6 to 30 carbon atoms, preferably those having 6 to 20 carbon atoms. Examples of aryloxy groups include phenoxy and biphenyloxy. Additionally, the aryloxy group may be optionally substituted.

Arylalkyl—as used herein, contemplates alkyl substituted with an aryl group. Arylalkyl may be those having 7 to 30 carbon atoms, preferably those having 7 to 20 carbon atoms, and more preferably those having 7 to 13 carbon atoms. Examples of arylalkyl groups include benzyl, 1-phenylethyl, 2-phenylethyl, 1-phenylisopropyl, 2-phenylisopropyl, phenyl-t-butyl, alpha-naphthylmethyl, 1-alpha-naphthylethyl, 2-alpha-naphthylethyl, 1-alpha-naphthylisopropyl, 2-alpha-naphthylisopropyl, beta-naphthylmethyl, 1-beta-naphthylethyl, 2-beta-naphthylethyl, 1-beta-naphthylisopropyl, 2-beta-naphthylisopropyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, and 1-chloro-2-phenylisopropyl. Of the above, preferred are benzyl, p-cyanobenzyl, m-cyanobenzyl, o-cyanobenzyl, 1-phenylethyl, 2-phenylethyl, 1-phenylisopropyl, and 2-phenylisopropyl. Additionally, the arylalkyl group may be optionally substituted.

Alkylsilyl—as used herein, contemplates a silyl group substituted with an alkyl group. Alkylsilyl groups may be those having 3 to 20 carbon atoms, preferably those having 3 to 10 carbon atoms. Examples of alkylsilyl groups include trimethylsilyl, triethylsilyl, methyldiethylsilyl, ethyldimethylsilyl, tripropylsilyl, tributylsilyl, triisopropylsilyl, methyldiisopropylsilyl, dimethylisopropylsilyl, tri-t-butylsilyl, triisobutylsilyl, dimethyl t-butylsilyl, and methyl di-t-butylsilyl. Additionally, the alkylsilyl group may be optionally substituted.

Arylsilyl—as used herein, contemplates a silyl group substituted with at least one aryl group. Arylsilyl groups may be those having 6 to 30 carbon atoms, preferably those having 8 to 20 carbon atoms. Examples of arylsilyl groups include triphenylsilyl, phenyldibiphenylylsilyl, diphenylbiphenylsilyl, phenyldiethylsilyl, diphenylethylsilyl, phenyldimethylsilyl, diphenylmethylsilyl, phenyldiisopropylsilyl, diphenylisopropylsilyl, diphenylbutylsilyl, diphenylisobutylsilyl, diphenyl t-butylsilyl, tri-t-butylsilyl, dimethyl t-butylsilyl, methyl di-t-butylsilyl. Additionally, the arylsilyl group may be optionally substituted.

The term "aza" in azadibenzofuran, azadibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, substituted heterocyclic group, substituted arylalkyl, substituted alkoxy, substituted aryloxy, substituted alkenyl, substituted alkynyl, substituted aryl, substituted heteroaryl, substituted alkylsilyl, substituted arylsilyl, substituted amino group, substituted acyl, substituted carbonyl, substituted carboxylic acid group, substituted ester group, substituted sulfinyl, substituted sulfonyl and substituted phosphino is used, it means that any group of alkyl, cycloalkyl, heteroalkyl, arylalkyl, alkoxy, aryloxy, alkenyl, aryl, heteroaryl, alkylsilyl, arylsilyl, amino group, acyl, carbonyl, carboxylic acid group, ester group, sulfinyl, sulfonyl and phosphino may be substituted with one or more groups selected from the group consisting of deuterium, a halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted heterocyclic group having 3 to 20 carbon atoms, an unsubstituted arylalkyl group having 7 to 30 carbon atoms, an unsubstituted alkoxy group having 1 to 20 carbon atoms, an unsubstituted aryloxy group having 6 to 30 carbon atoms, an unsubstituted alkenyl group having 2 to 20 carbon atoms, an unsubstituted alkynyl group having 2 to 20 carbon atoms, an unsubstituted aryl group having 6 to 30 carbon atoms, an unsubstituted heteroaryl group having 3 to 30 carbon atoms, an unsubstituted alkylsilyl group having 3 to 20 carbon atoms, an unsubstituted arylsilyl group having 6 to 20 carbon atoms, an unsubstituted amino group having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group and a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in the present disclosure, the hydrogen atoms can be partially or fully replaced by deuterium. Other atoms such as carbon and nitrogen can also be replaced by their other stable isotopes. The replacement by other stable isotopes in the compounds may be preferred due to its enhancements of device efficiency and stability.

In the compounds mentioned in the present disclosure, multiple substitutions refer to a range that includes double substitutions, up to the maximum available substitutions. When a substitution in the compounds mentioned in the present disclosure represents multiple substitutions (including di, tri, tetra substitutions, etc.), that means the substituent may exist at a plurality of available substitution positions on its linking structure, the substituents present at a plurality of available substitution positions may be the same structure or different structures.

In the compounds mentioned in the present disclosure, adjacent substituents in the compounds cannot connect to form a ring unless otherwise explicitly defined, for example, adjacent substituents can be optionally joined to form a ring. In the compounds mentioned in the present disclosure, adjacent substituents can be optionally joined to form a ring, including both the case where adjacent substituents can be joined to form a ring, and the case where adjacent substituents are not joined to form a ring. When adjacent substituents can be optionally joined to form a ring, the ring formed may be monocyclic or polycyclic, as well as alicyclic, heteroalicyclic, aromatic or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that adjacent substituents can be optionally joined to form a ring is also intended to mean that two substituents bonded to the same carbon atom are joined to each other via a chemical bond to form a ring, which can be exemplified by the following formula:

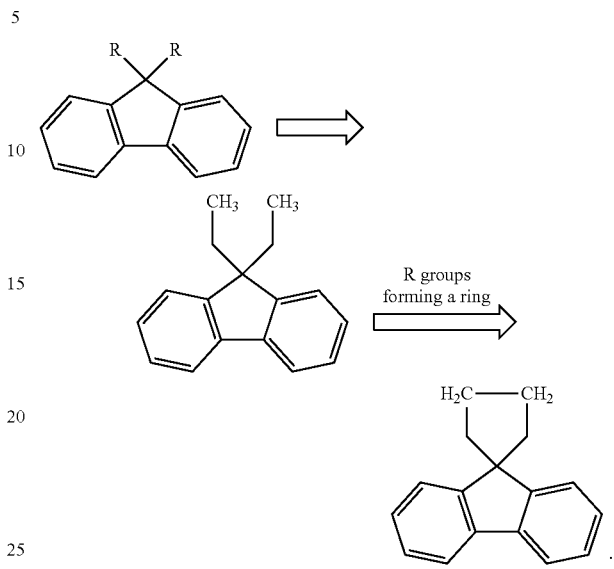

The expression that adjacent substituents can be optionally joined to form a ring is also intended to mean that two substituents bonded to carbon atoms which are directly bonded to each other are joined to each other via a chemical bond to form a ring, which can be exemplified by the following formula:

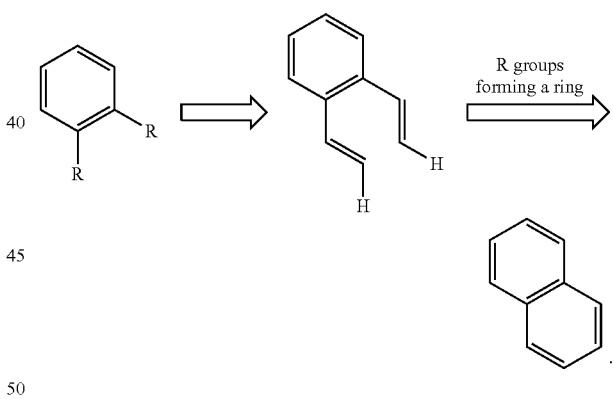

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

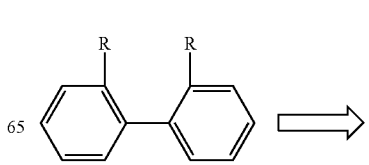

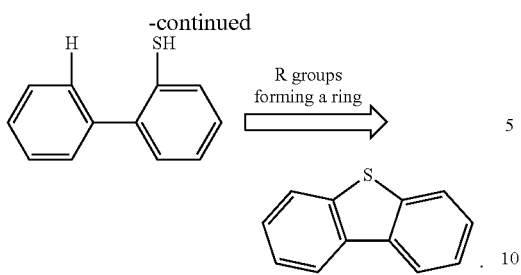

According to an embodiment of the present disclosure, disclosed is a compound having a structure of H-L-E, wherein H has a structure represented by Formula 1:

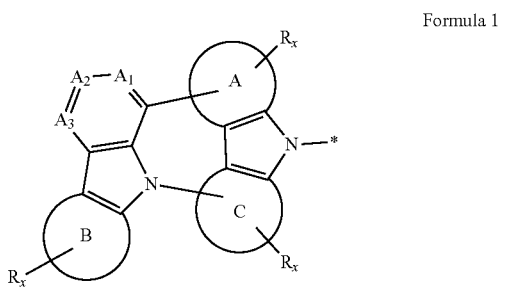

Formula 1 in Formula 1, $A_1$, $A_2$, and $A_3$ are, at each occurrence identically or differently, selected from N or CR, and the ring A, the ring B, and the ring C are, at each occurrence identically or differently, selected from a carbocyclic ring having 5 to 18 carbon atoms or a heterocyclic ring having 3 to 18 carbon atoms;

$R_x$ represents, at each occurrence identically or differently, mono-substitution, multiple substitutions, or non-substitution;

E has a structure represented by Formula 2:

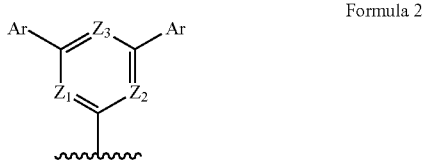

Formula 2 in Formula 2, Ar is, at each occurrence identically or differently, selected from substituted or unsubstituted aryl having 6 to 30 carbon atoms or substituted or unsubstituted heteroaryl having 3 to 30 carbon atoms;

$Z_1$ to $Z_3$ are each independently selected from N or $CR_z$, and at least one of $Z_1$ to $Z_3$ is N;

L has a structure represented by Formula 3:

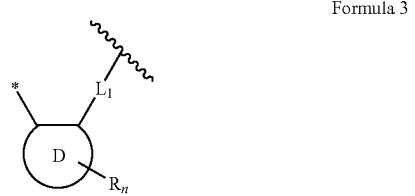

Formula 3 in Formula 3, the ring D is, at each occurrence identically or differently, selected from a carbocyclic ring having 5 to 18 carbon atoms or a heterocyclic ring having 3 to 18 carbon atoms;

$R_n$ represents, at each occurrence identically or differently, mono-substitution, multiple substitutions, or non-substitution;

$L_1$ is selected from a single bond, substituted or unsubstituted arylene having 6 to 30 carbon atoms, substituted or unsubstituted heteroarylene having 3 to 30 carbon atoms, or combinations thereof; and when $L_1$ is selected from substituted arylene having 6 to 30 carbon atoms or substituted heteroarylene having 3 to 30 carbon atoms, $L_1$ has a substituent $R_m$; and $R_m$ represents, at each occurrence identically or differently, mono-substitution or multiple substitutions;

R, $R_x$, $R_z$, $R_n$, and $R_m$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents R, $R_x$ can be optionally joined to form a ring;

adjacent substituents $R_n$, $R_m$ can be optionally joined to form a ring.

In the present embodiment, in Formula 3, "*" represents the position where the structure L represented by Formula 3 is connected to the structure H represented by Formula 1, and the "~~~" represents the position where the structure L represented by Formula 3 is connected to the structure E represented by Formula 2.

In the present embodiment, the expression that adjacent substituents R, $R_x$ can be optionally joined to form a ring is intended to mean that adjacent substituents R can be optionally joined to form a ring, is also intended to mean that when there are a plurality of $R_x$ on the ring A, adjacent substituents $R_x$ can be optionally joined to form a ring, is also intended to mean that when there are a plurality of $R_x$ on the ring B, adjacent substituents $R_x$ can be optionally joined to form a ring, is also intended to mean that when there are a plurality of $R_x$ on the ring C, adjacent substituents $R_x$ can be optionally joined to form a ring, and is also intended to mean that adjacent substituents R and $R_x$ can be optionally joined to form a ring. It is obvious for those skilled in the art that adjacent substituents R and $R_x$ may not be joined to form a ring, and in this case, adjacent substituents R are not joined to form a ring, and/or adjacent substituents $R_x$ are not joined to form a ring, and/or adjacent substituents R and $R_x$ are also not joined to form a ring.

In the present disclosure, the expression that adjacent substituents $R_n$, $R_m$ can be optionally joined to form a ring is intended to mean that when there are substituents $R_n$ and $R_m$, any one or more of groups of adjacent substituents, for example, adjacent substituents $R_n$, adjacent substituents $R_m$, and substituents $R_n$ and $R_m$, can be joined to form a ring. Obviously, in the presence of substituents $R_n$ and $R_m$, it is possible that none of these groups of adjacent substituents are joined to form a ring.

According to an embodiment of the present disclosure, wherein, in Formula 1, the ring A, the ring B, and the ring C are, at each occurrence identically or differently, selected from a five-membered carbocyclic ring, an aromatic ring having 6 to 18 carbon atoms, or a heteroaromatic ring having 3 to 18 carbon atoms.

According to an embodiment of the present disclosure, wherein in Formula 1, the ring A, the ring B, and the ring C are, at each occurrence identically or differently, selected from a five-membered carbocyclic ring, a benzene ring, a five-membered heteroaromatic ring, or a six-membered heteroaromatic ring.

According to an embodiment of the present disclosure, wherein the H has a structure represented by Formula 1-a:

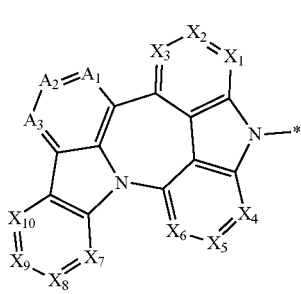

Formula 1-a $A_1$ to $A_3$ are, at each occurrence identically or differently, selected from N or CR, and $X_1$ to $X_{10}$ are, at each occurrence identically or differently, selected from N or $CR_x$;

R and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents R, $R_x$ can be optionally joined to form a ring.

In the present disclosure, the expression that adjacent substituents R, $R_x$ can be optionally joined to form a ring is intended to mean that adjacent substituents R can be optionally joined to form a ring, is also intended to mean that adjacent substituents $R_x$ in $X_1$ to $X_3$ can be optionally joined to form a ring, is also intended to mean that that adjacent substituents $R_x$ in $X_4$ to $X_6$ can be optionally joined to form a ring, is also intended to mean that that adjacent substituents $R_x$ in $X_7$ to $X_{10}$ can be optionally joined to form a ring, and is also intended to mean that that adjacent substituents R and $R_x$ can be optionally joined to form a ring, for example, adjacent substituents in $A_1$ and $X_3$, and/or adjacent substituents in $A_3$ and $X_{10}$, and/or adjacent substituents in $X_6$ and $X_7$ can be optionally joined to form a ring. It is obvious for those skilled in the art that adjacent substituents R and $R_x$ may not be joined to form a ring, and in this case, adjacent substituents R are not joined to form a ring, and/or adjacent substituents $R_x$ are not joined to form a ring, and/or adjacent substituents R and $R_x$ are also not joined to form a ring.

According to an embodiment of the present disclosure, wherein, in Formula 1-a, R and $R_x$ are, at each occurrence identically or differently, selected from the group consisting of: hydrogen, deuterium, halogen, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a hydroxyl group, a sulfanyl group, and combinations thereof, adjacent substituents R, $R_x$ can be optionally joined to form a ring.

According to an embodiment of the present disclosure, wherein in Formula 1-a, at least one of R and $R_x$ is selected from deuterium, substituted or unsubstituted aryl having 6 to 30 carbon atoms, or substituted or unsubstituted heteroaryl having 3 to 30 carbon atoms.

According to an embodiment of the present disclosure, wherein in Formula 1-a, at least one of R and $R_x$ is selected from deuterium, phenyl, biphenyl, or pyridyl.

According to an embodiment of the present disclosure, wherein in Formula 1-a, at least one of groups of adjacent substituents: adjacent substituents R in $A_1$ to $A_3$, adjacent substituents $R_x$ in $X_1$ to $X_3$, adjacent substituents $R_x$ in $X_4$ to $X_6$, and adjacent substituents $R_x$ in $X_7$ to $X_{10}$ is joined to form a ring.

In the present embodiment, the expression that at least one of groups of adjacent substituents is joined to form a ring is intended to mean that for groups of adjacent substituents present in Formula 1-a, for example, two adjacent substituents R in $A_1$ and $A_2$, two adjacent substituents R in $A_2$ and $A_3$, two adjacent substituents $R_x$ in $X_1$ and $X_2$, two adjacent substituents $R_x$ in $X_2$ and $X_3$, two adjacent substituents $R_x$ in $X_4$ and $X_5$, two adjacent substituents $R_x$ in $X_5$ and $X_6$, two adjacent substituents $R_x$ in $X_7$ and $X_8$, two adjacent substituents $R_x$ in $X_8$ and $X_9$, and two adjacent substituents $R_x$ in $X_9$ and $X_{10}$, at least one of these groups of substituents is joined to form a ring.

According to an embodiment of the present disclosure, wherein the H is selected from the group consisting of the following structures:
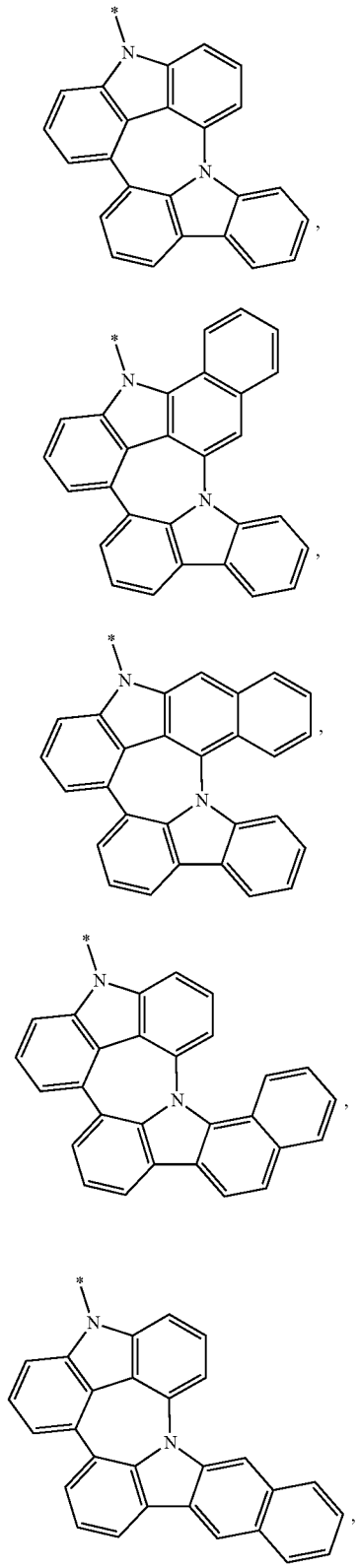
H-1
H-2
H-3
H-4
H-5
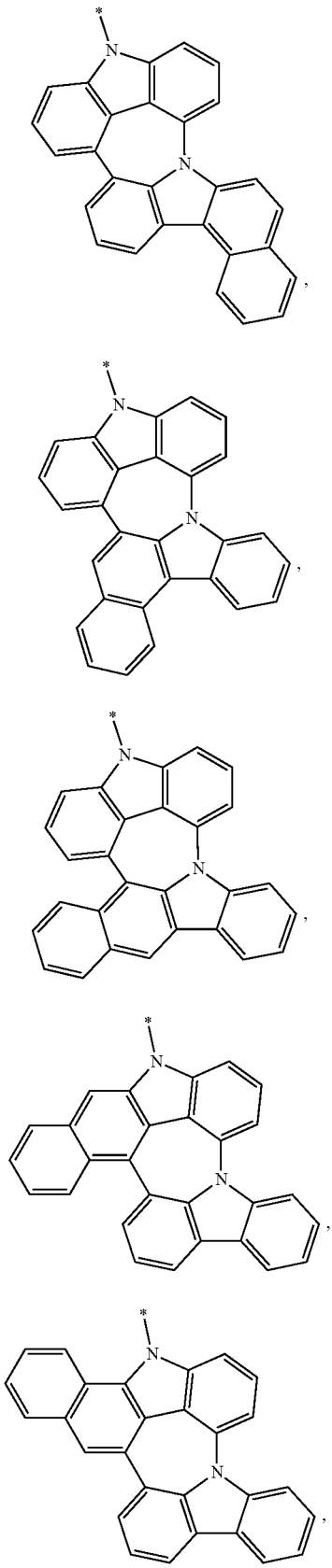
H-6
H-7
H-8
H-9
H-10

-continued
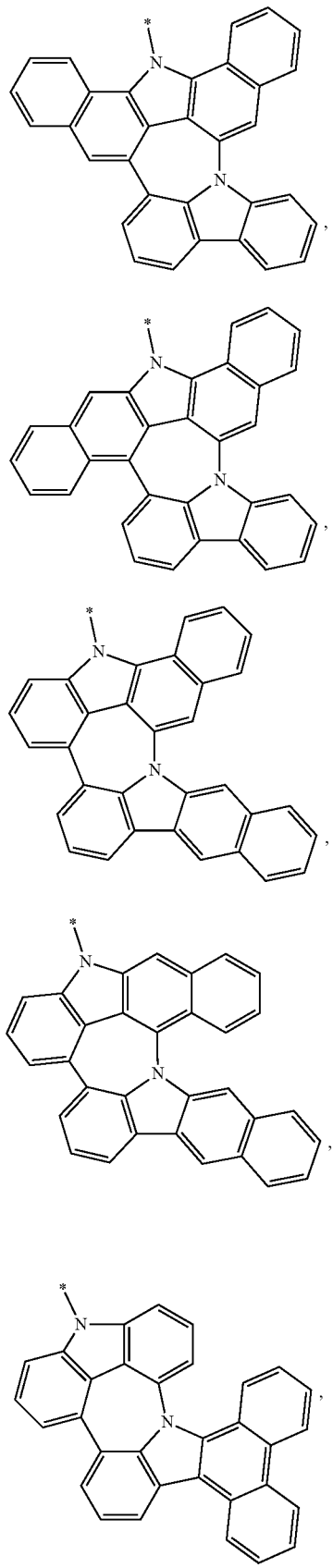
H-11
H-12
H-13
H-14
H-15
-continued
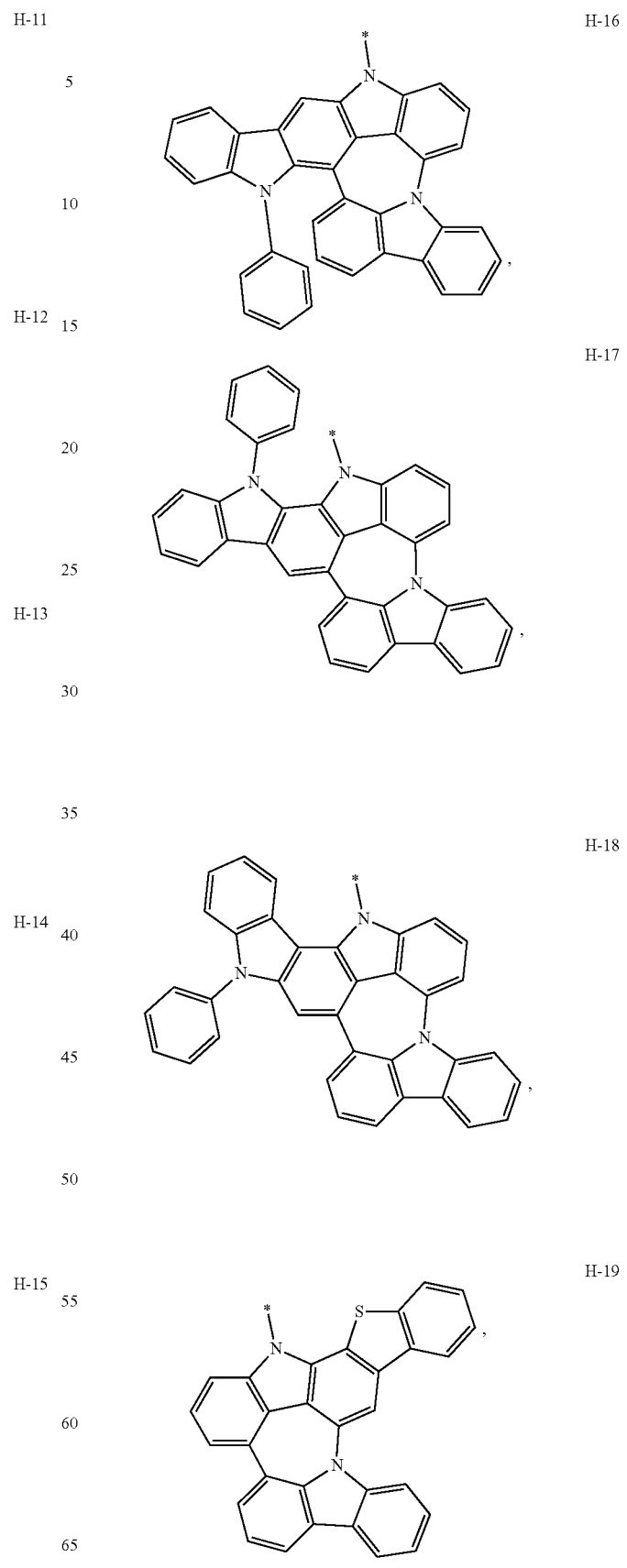
H-16
H-17
H-18
H-19

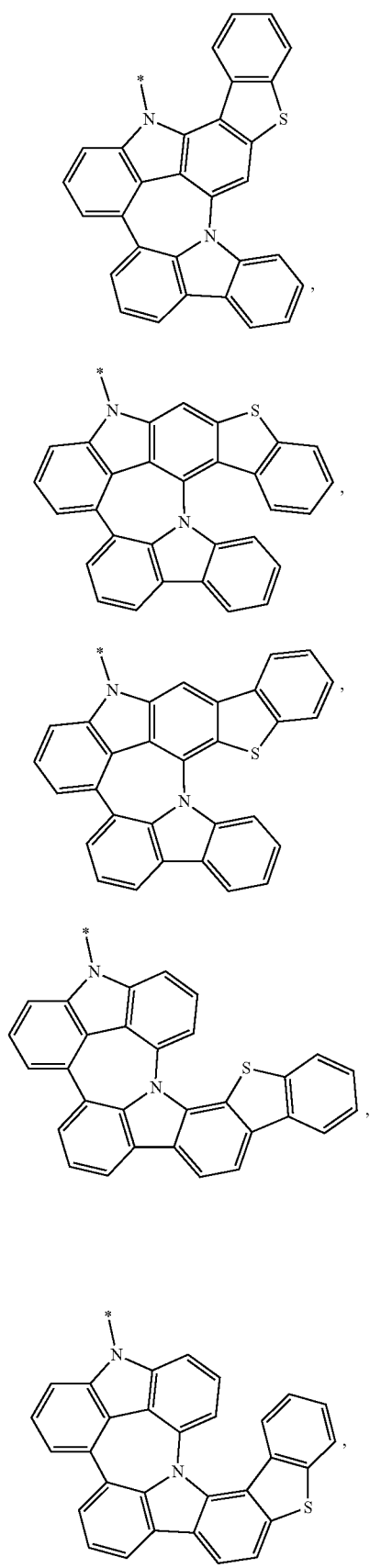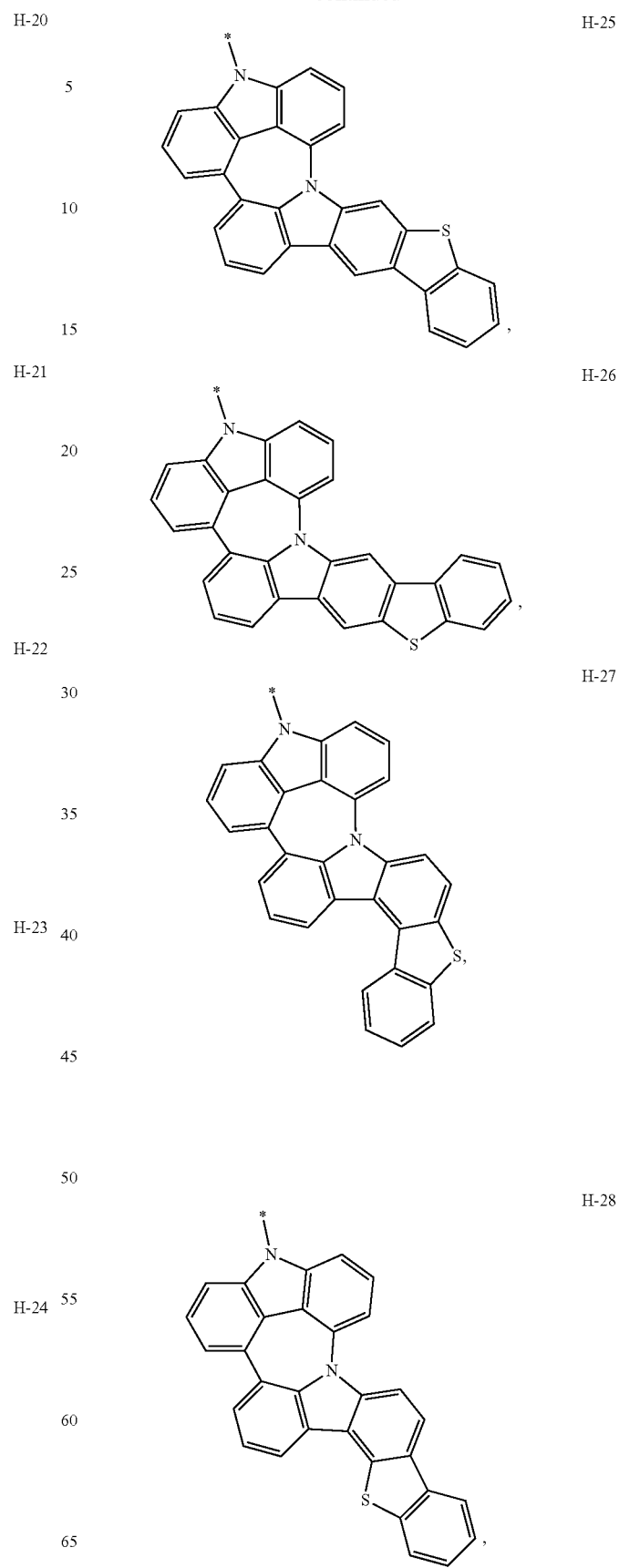

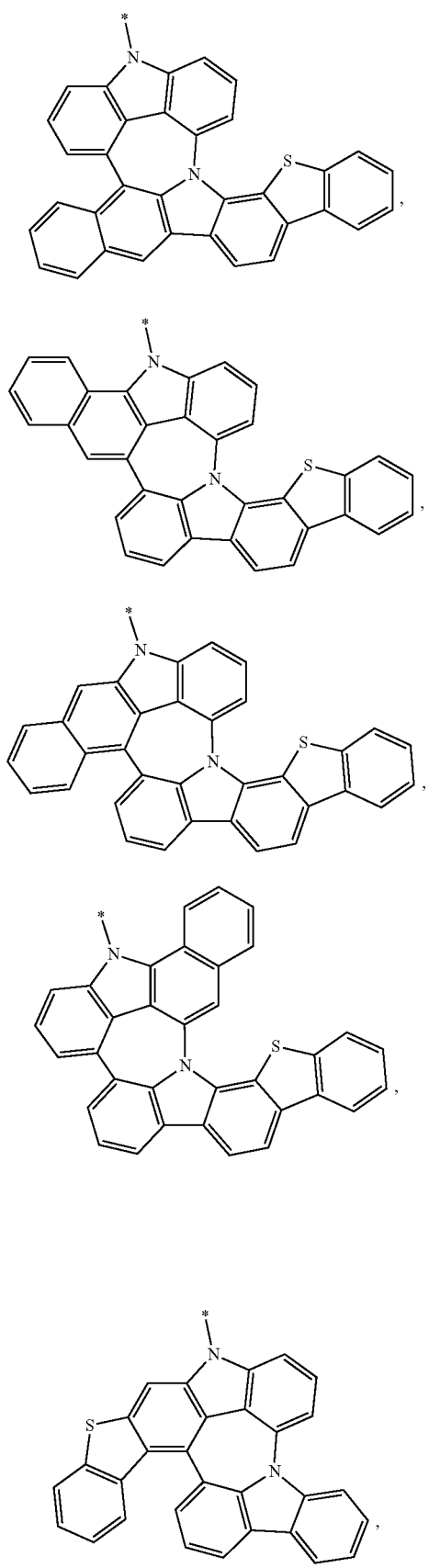

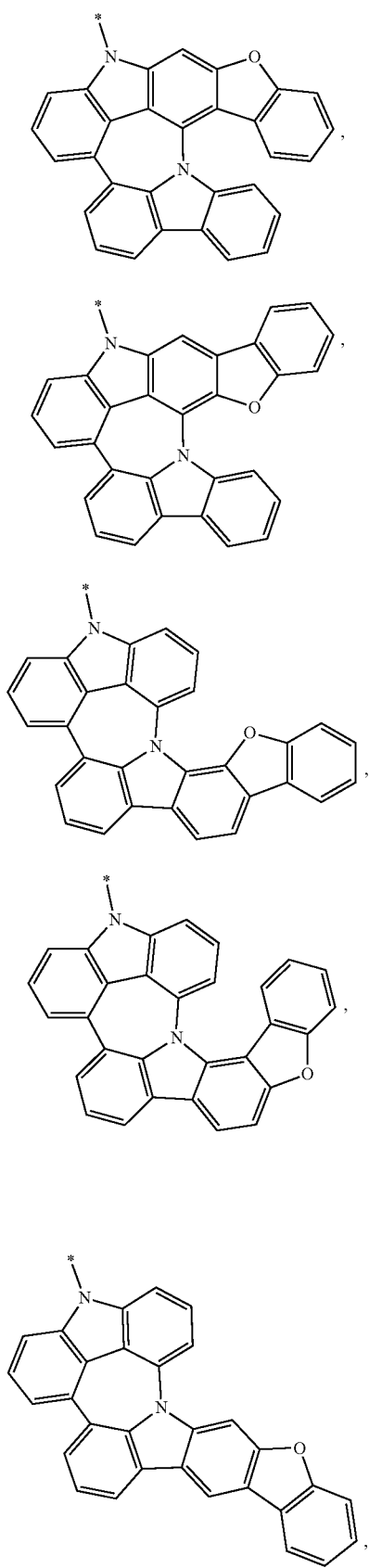
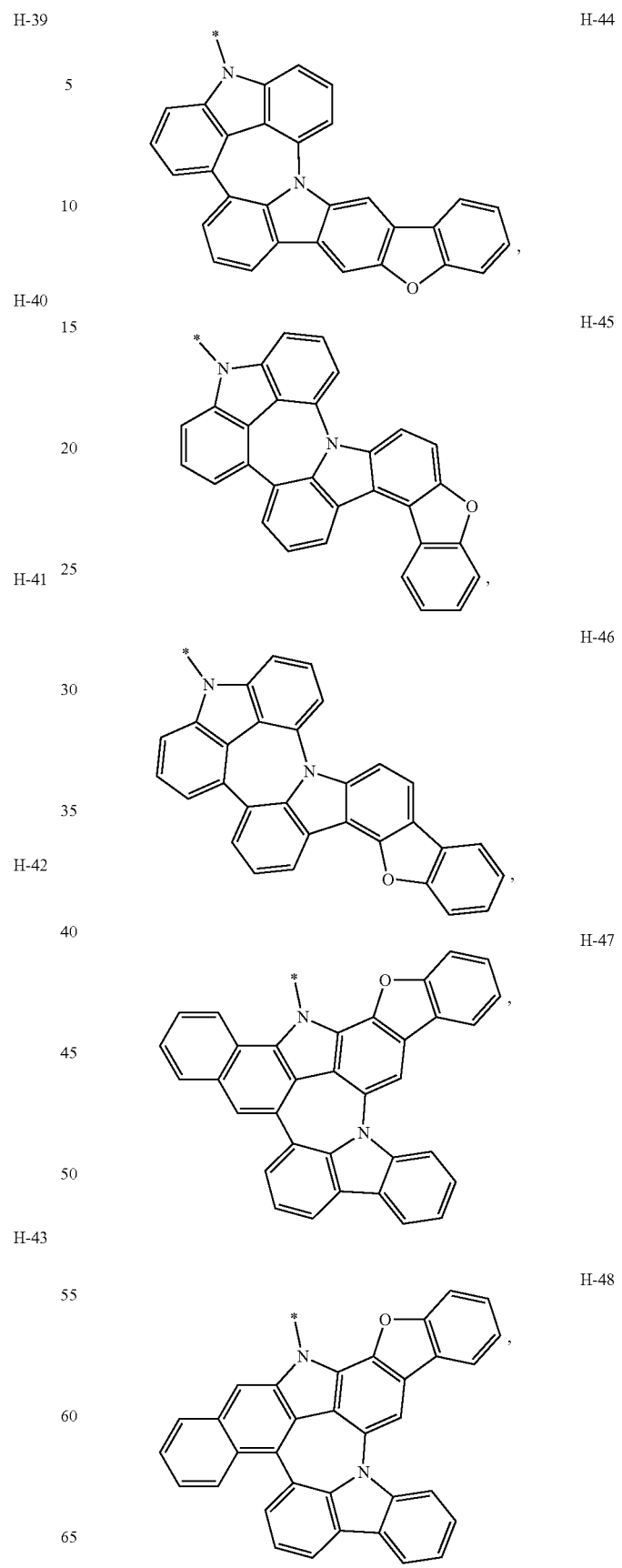

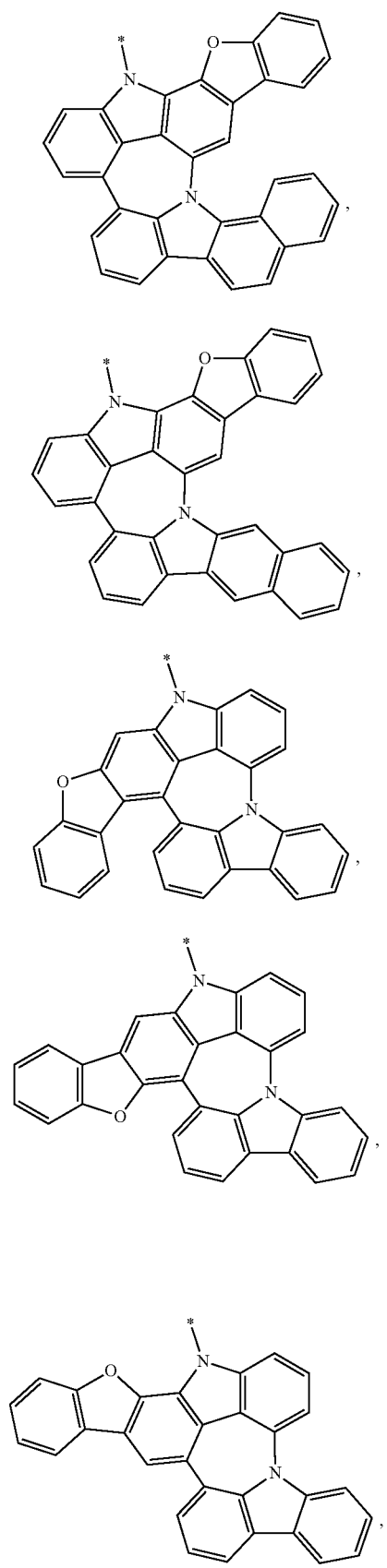
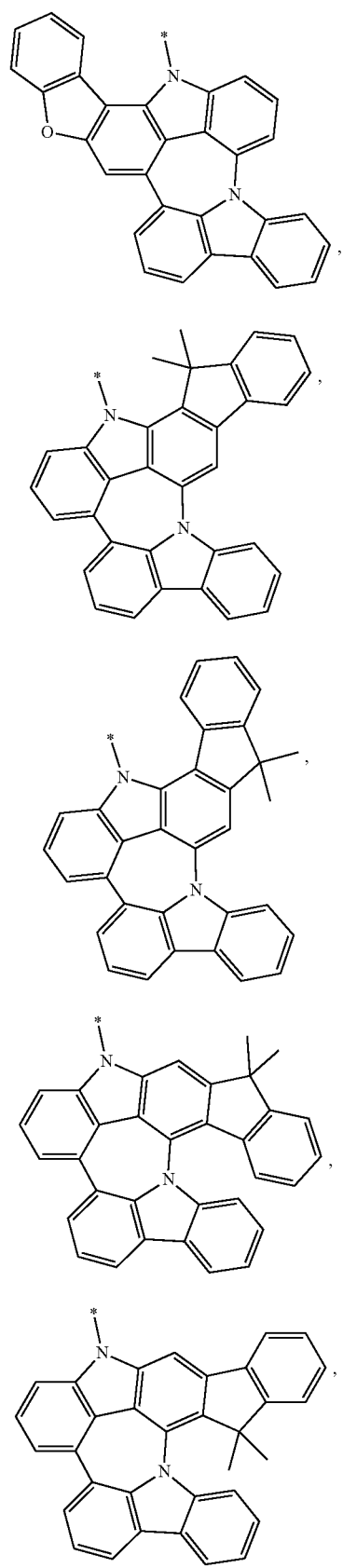

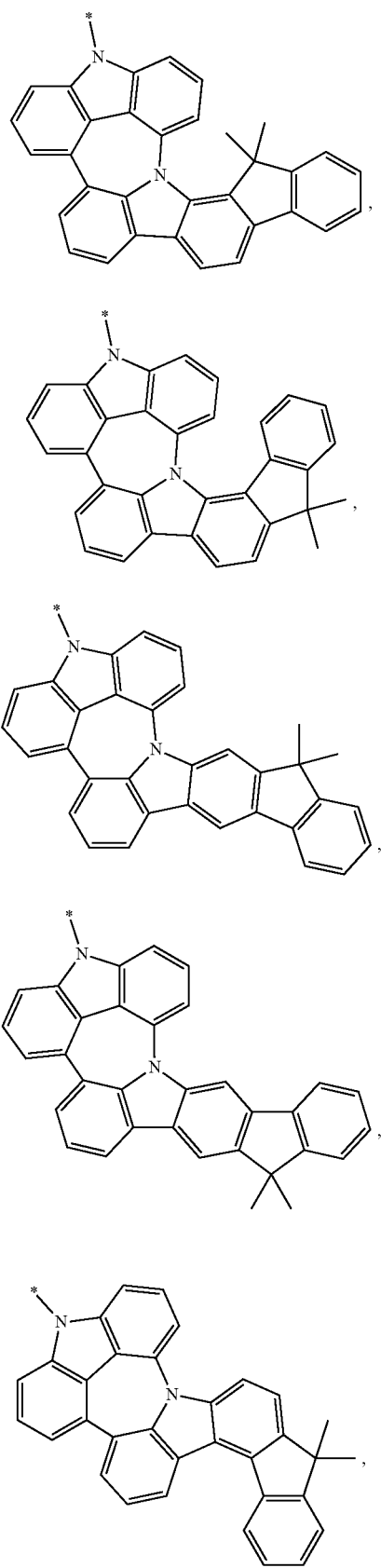
H-59
H-60
H-61
H-62
H-63
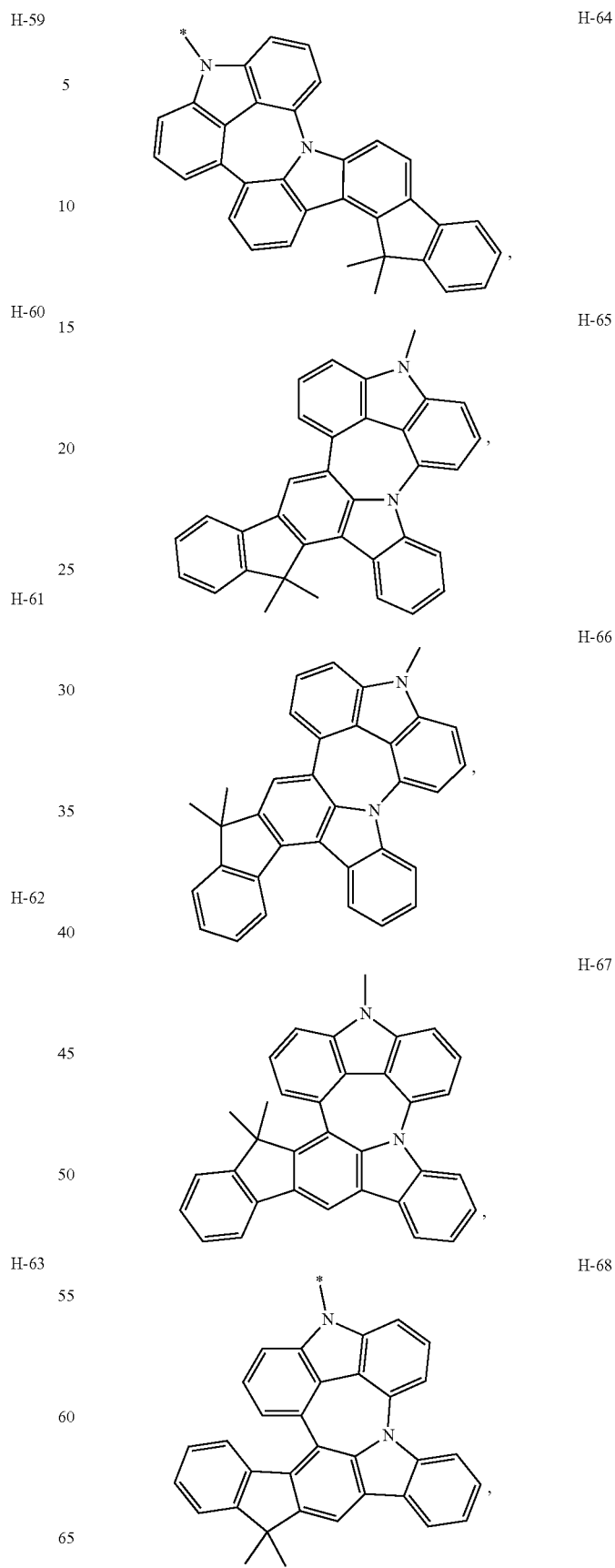
H-64
H-65
H-66
H-67
H-68

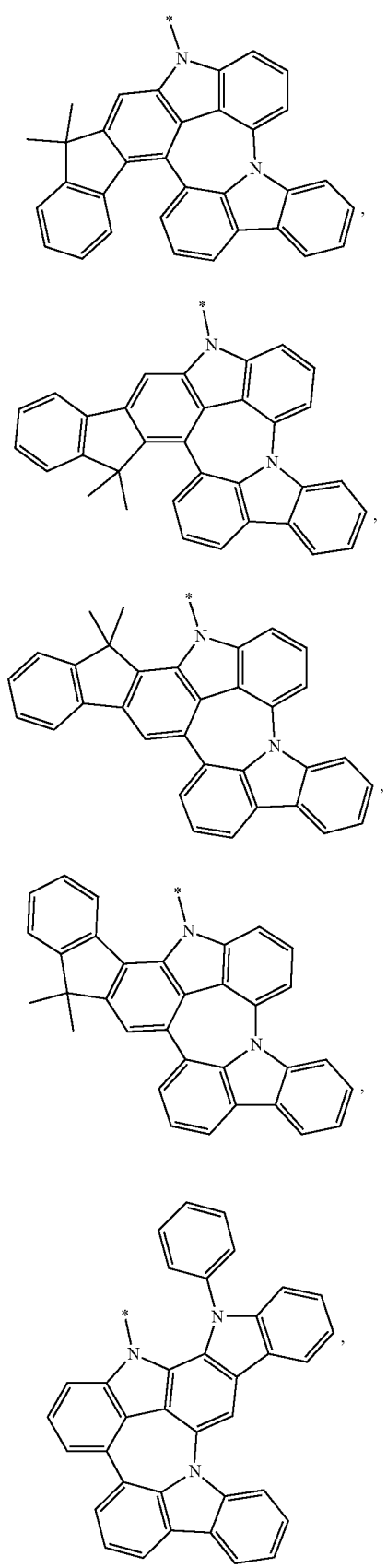
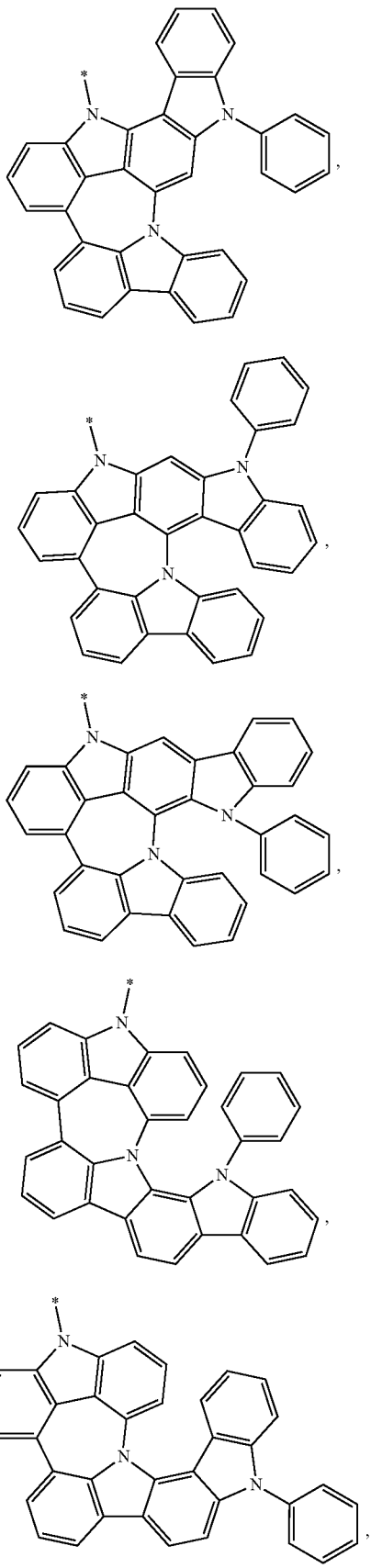

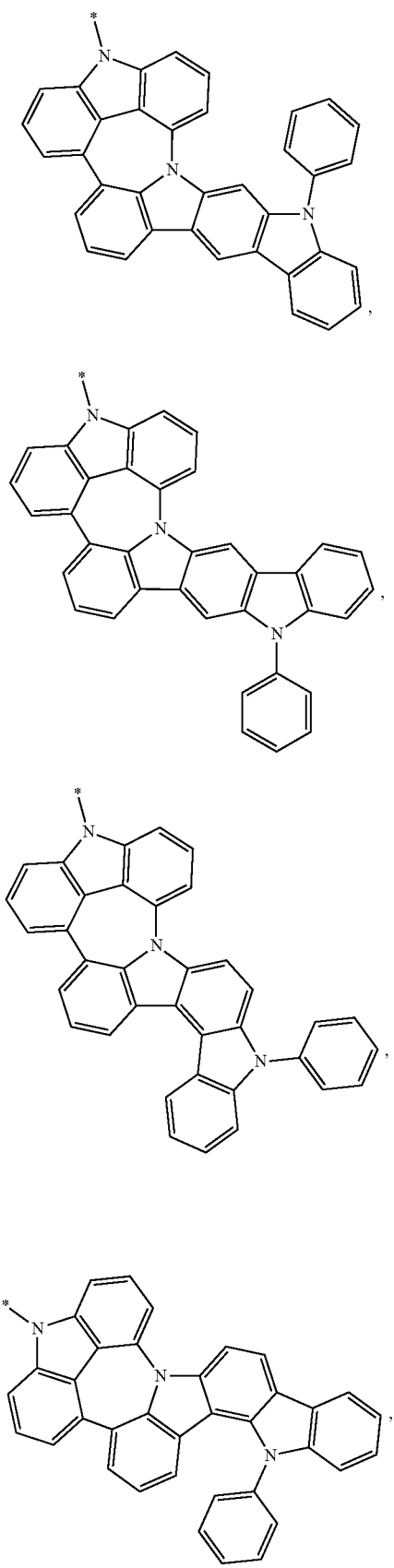
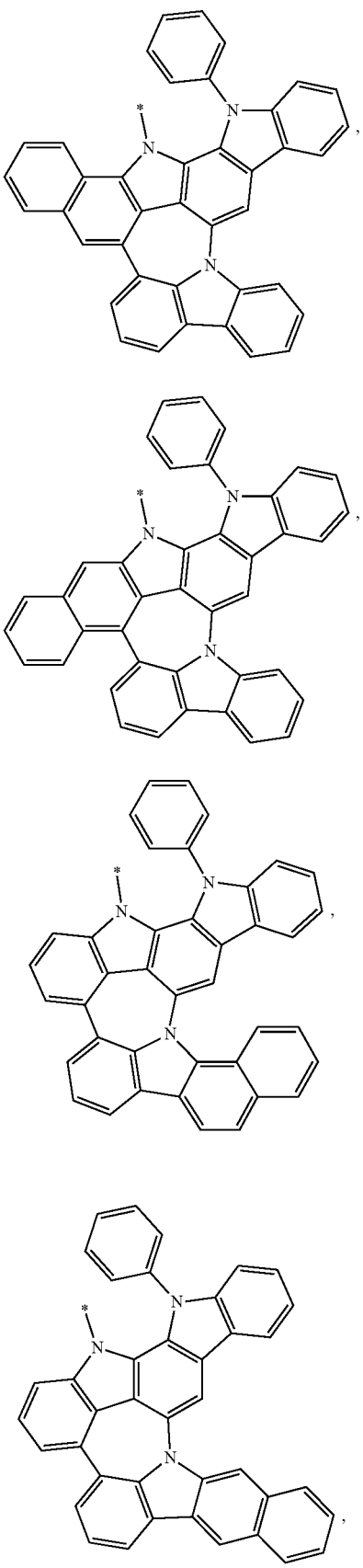

-continued
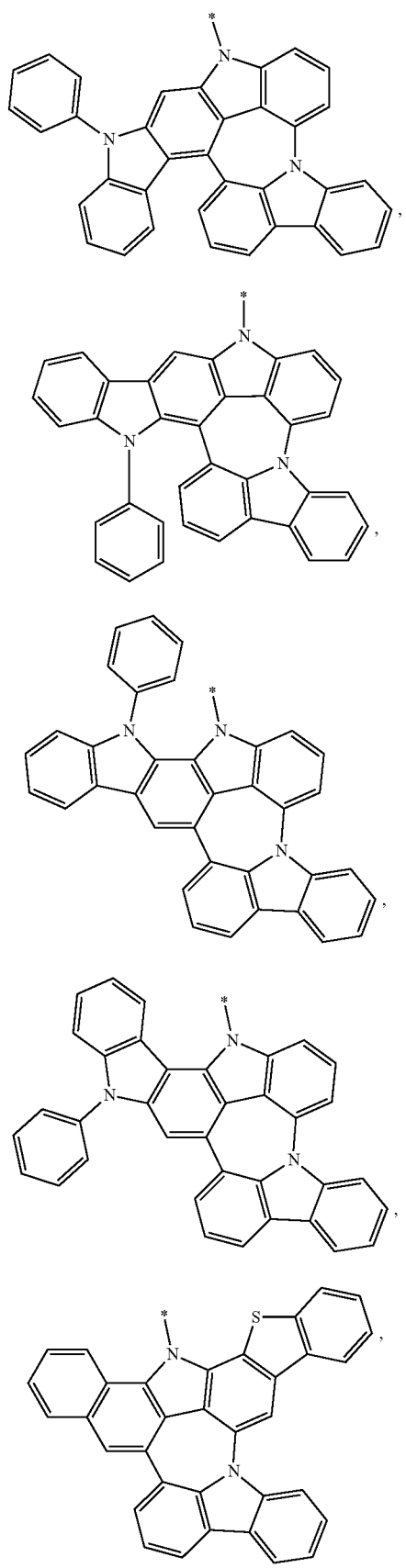
H-87
H-88
H-89
H-90
H-91
-continued
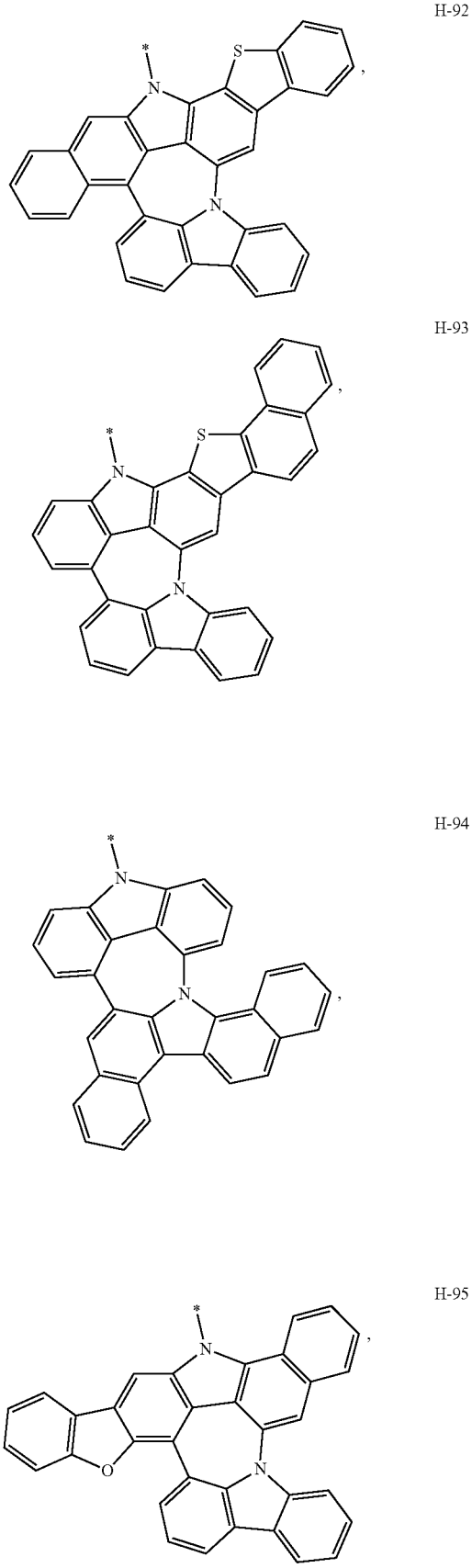
H-92
H-93
H-94
H-95

H-96
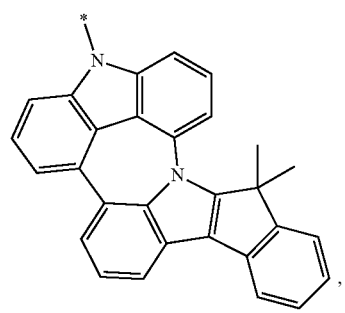
H-97
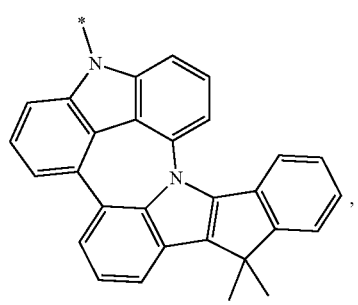
H-98
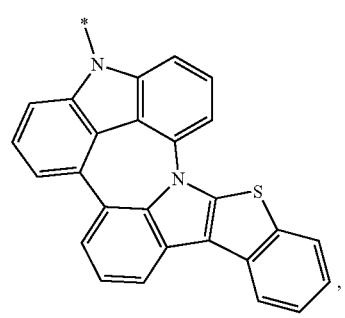
H-99
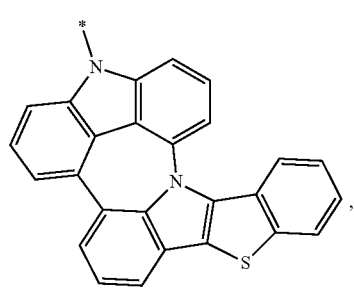
H-100
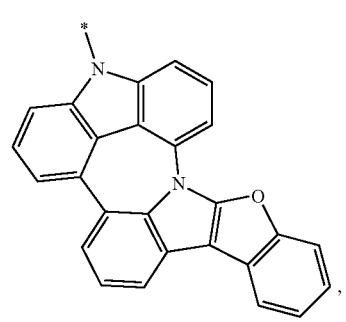
H-101
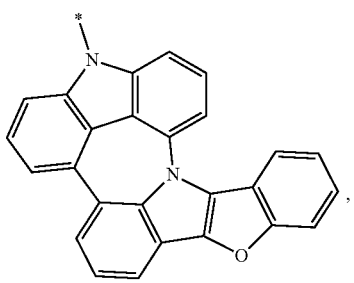
H-102
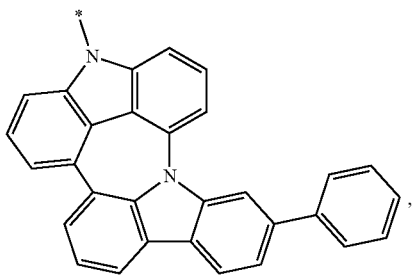
H-103
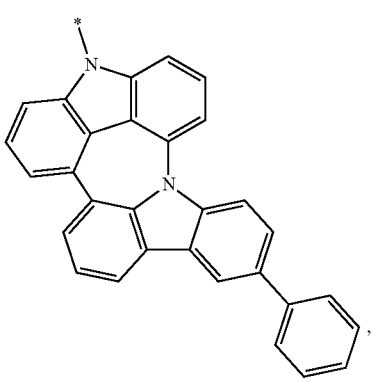
H-104
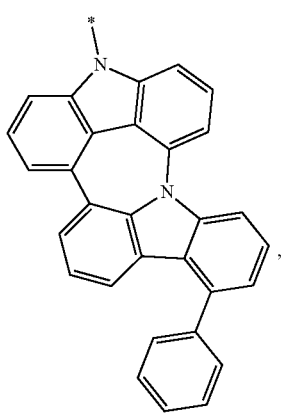

-continued
H-105
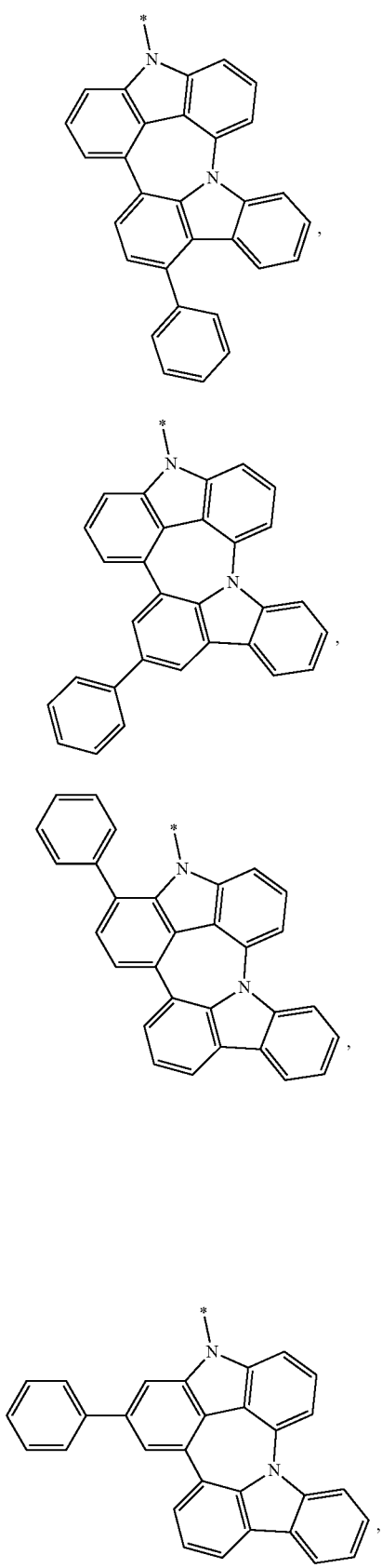
H-106
H-107
H-108
-continued
H-109
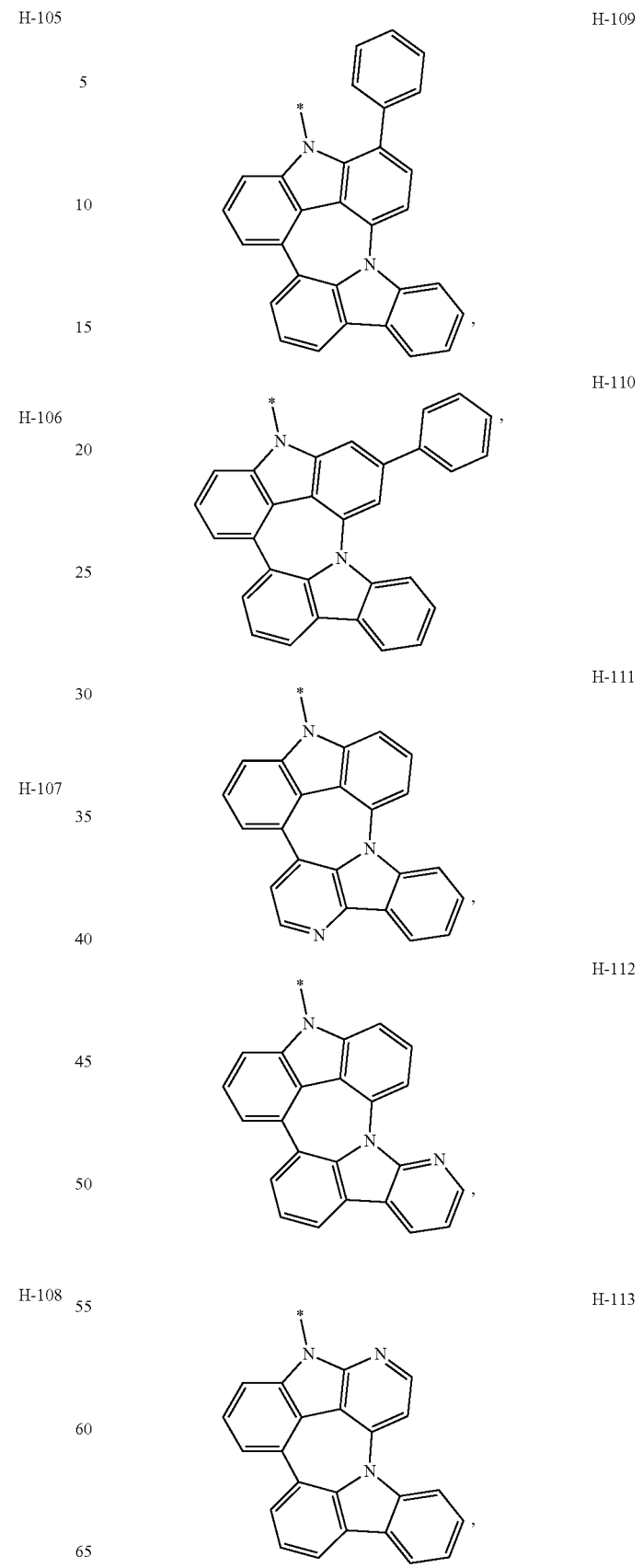
H-110
H-111
H-112
H-113

H-114 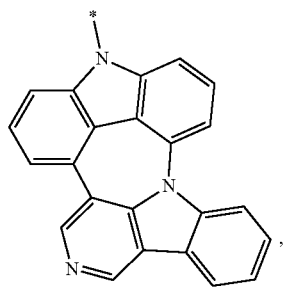
H-115 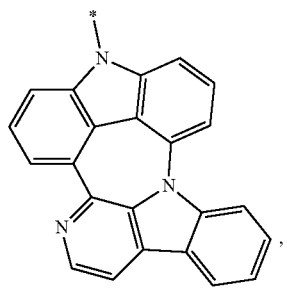
H-116 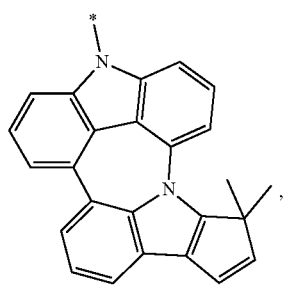
H-117 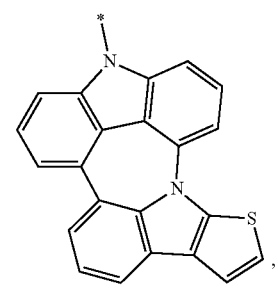
H-118 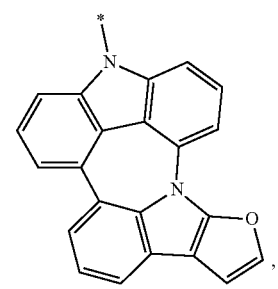
H-119 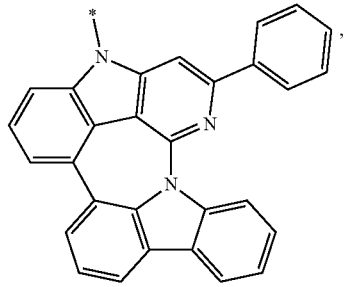
H-120 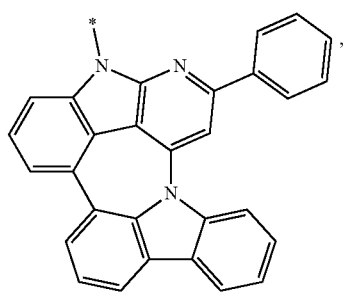
H-121 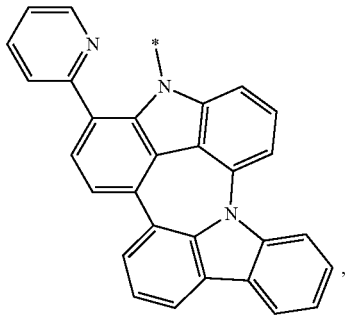
H-122 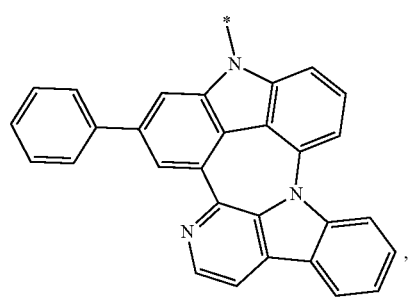
H-123 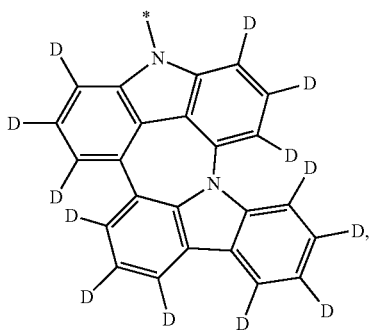

H-124
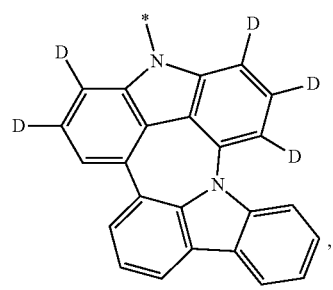
H-125
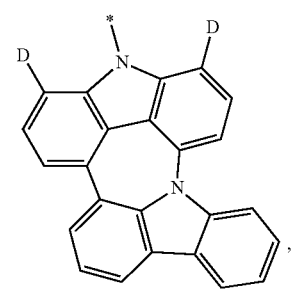
H-126
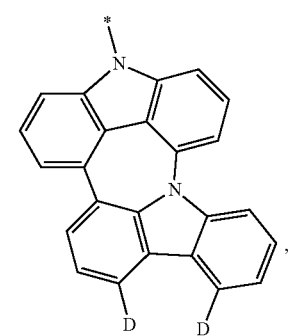
H-127
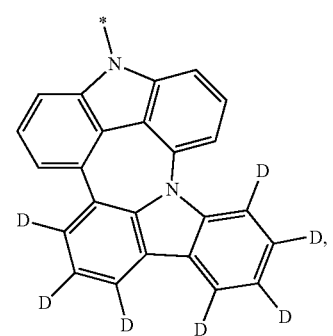
H-128
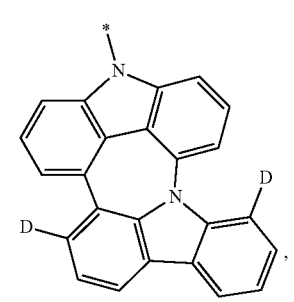
H-129
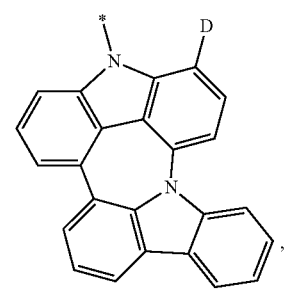
H-130
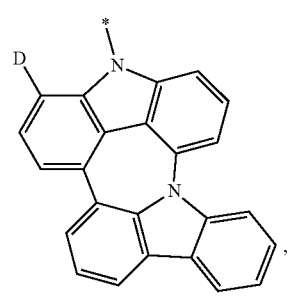
H-131
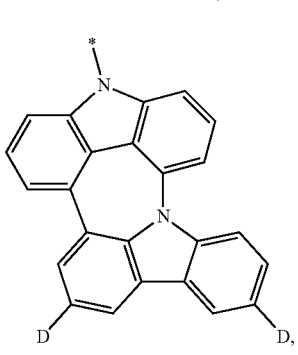
H-132
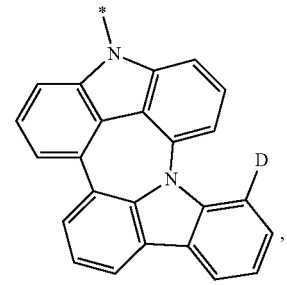
H-133
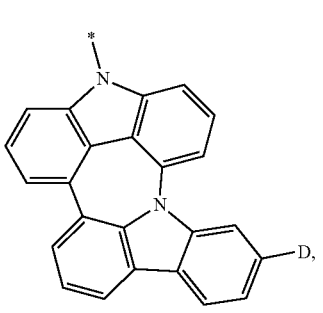

H-134 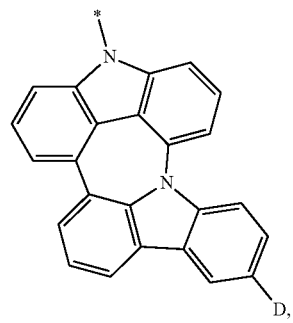

H-135 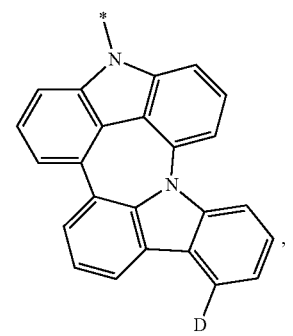

H-136 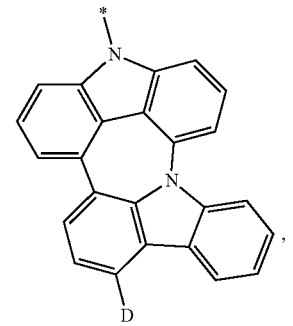

H-137 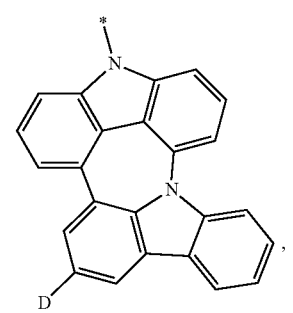

H-138 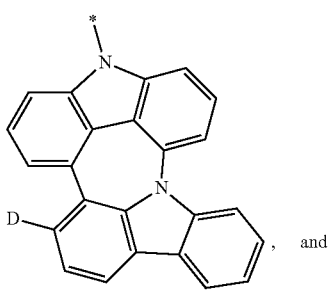, and

H-139 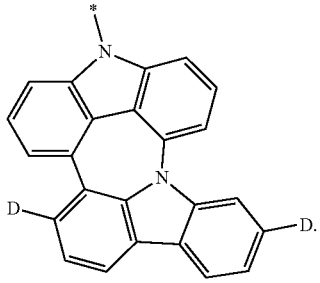

According to an embodiment of the present disclosure, wherein, hydrogens in the structures of H-1 to H-139 can be partially or completely substituted with deuterium.

According to an embodiment of the present disclosure, wherein E has a structure

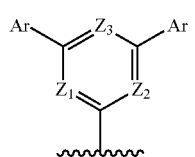

Formula 2 wherein $Z_1$ to $Z_3$ are each independently selected from N or $CR_z$, and at least two of $Z_1$ to $Z_3$ are N; for example, $Z_1$ and $Z_3$ are N, or $Z_1$ and $Z_2$ are N;

wherein $R_z$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, an isocyano group, a hydroxyl group, a sulfanyl group, and combinations thereof, Ar is, at each occurrence identically or differently, selected from substituted or unsubstituted aryl having 6 to 18 carbon atoms or substituted or unsubstituted heteroaryl having 3 to 18 carbon atoms.

According to an embodiment of the present disclosure, wherein, in Formula 2, $Z_1$ to $Z_3$ are each N.

According to an embodiment of the present disclosure, wherein, in Formula 2, Ar is, at each occurrence identically or differently, selected from the group consisting of: substituted or unsubstituted phenyl, substituted or unsubstituted naphthyl, substituted or unsubstituted dibenzofuranyl, substituted or unsubstituted dibenzothienyl, substituted or unsubstituted fluorenyl, substituted or unsubstituted carbazolyl, substituted or unsubstituted pyridyl, substituted or unsubstituted pyrimidinyl, substituted or unsubstituted triphenylene, and combinations thereof.

According to an embodiment of the present disclosure, wherein, in Formula 2, Ar is, at each occurrence identically or differently, selected from the group consisting of: phenyl, deuterated phenyl, methylphenyl, fluorophenyl, tert-butylphenyl, trideuteratedmethyl phenyl, biphenyl, naphthyl, deuterated naphthyl, dibenzofuranyl, dibenzothienyl, 9,9-dimethylfluorenyl, carbazolyl, pyridyl, pyrimidinyl, 4-cyanophenyl, 3-cyanophenyl, triphenylene, and combinations thereof.

According to an embodiment of the present disclosure, wherein, the E is selected from the group consisting of the following structures:

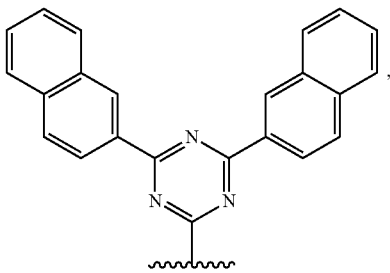

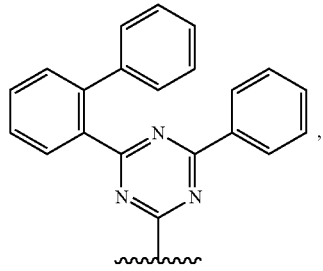

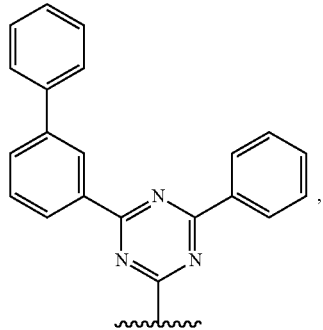

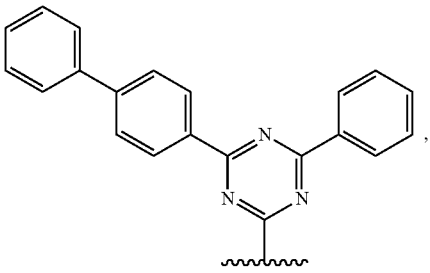

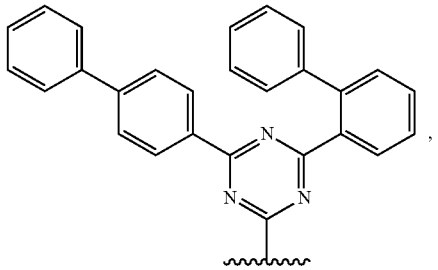

E-11
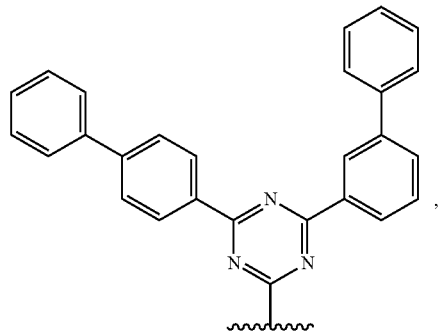
E-12
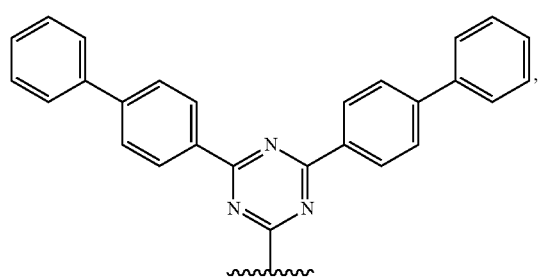
E-13
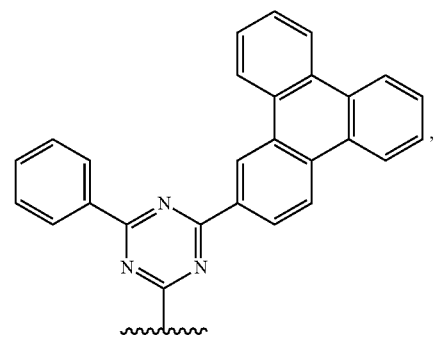
E-14
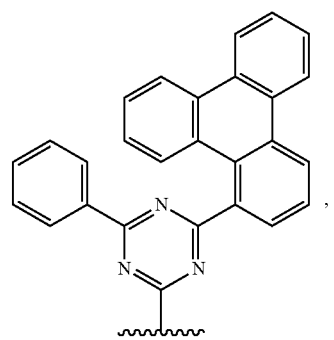
E-15
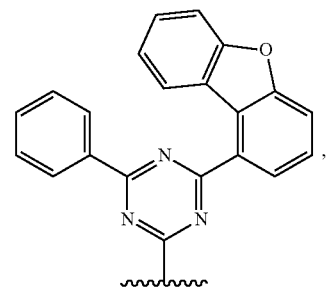
E-16
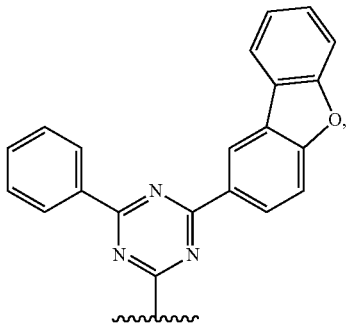
E-17
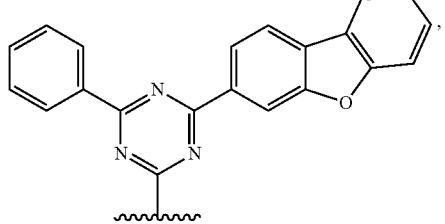
E-18
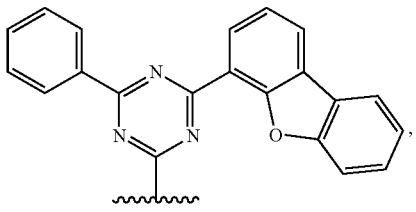
E-19
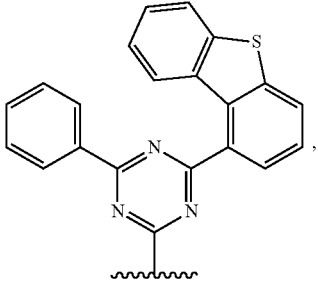
E-20
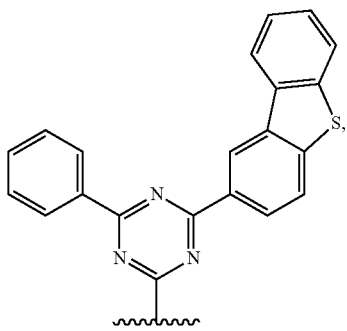

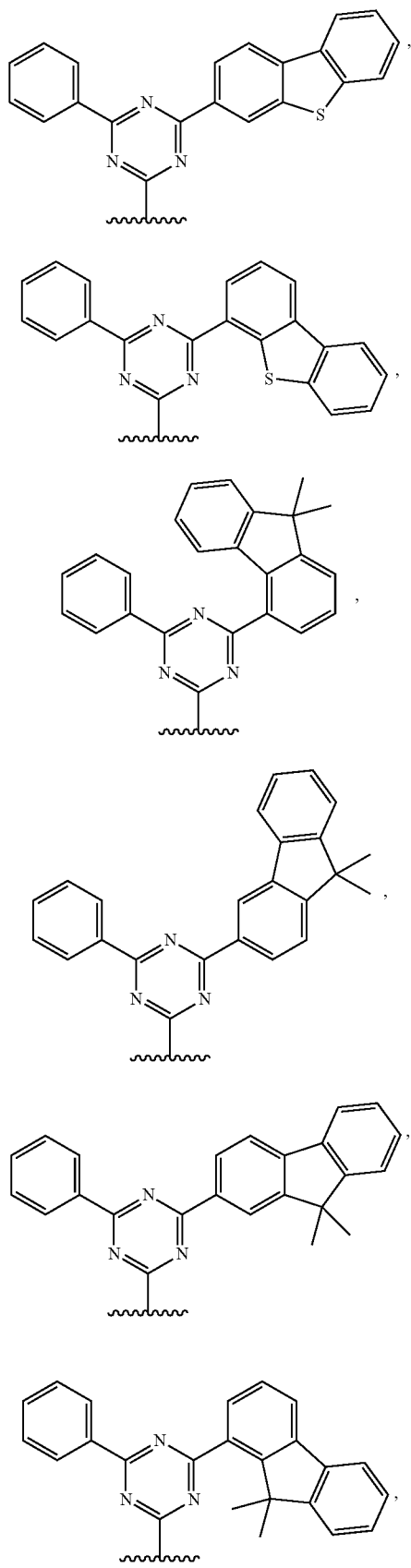
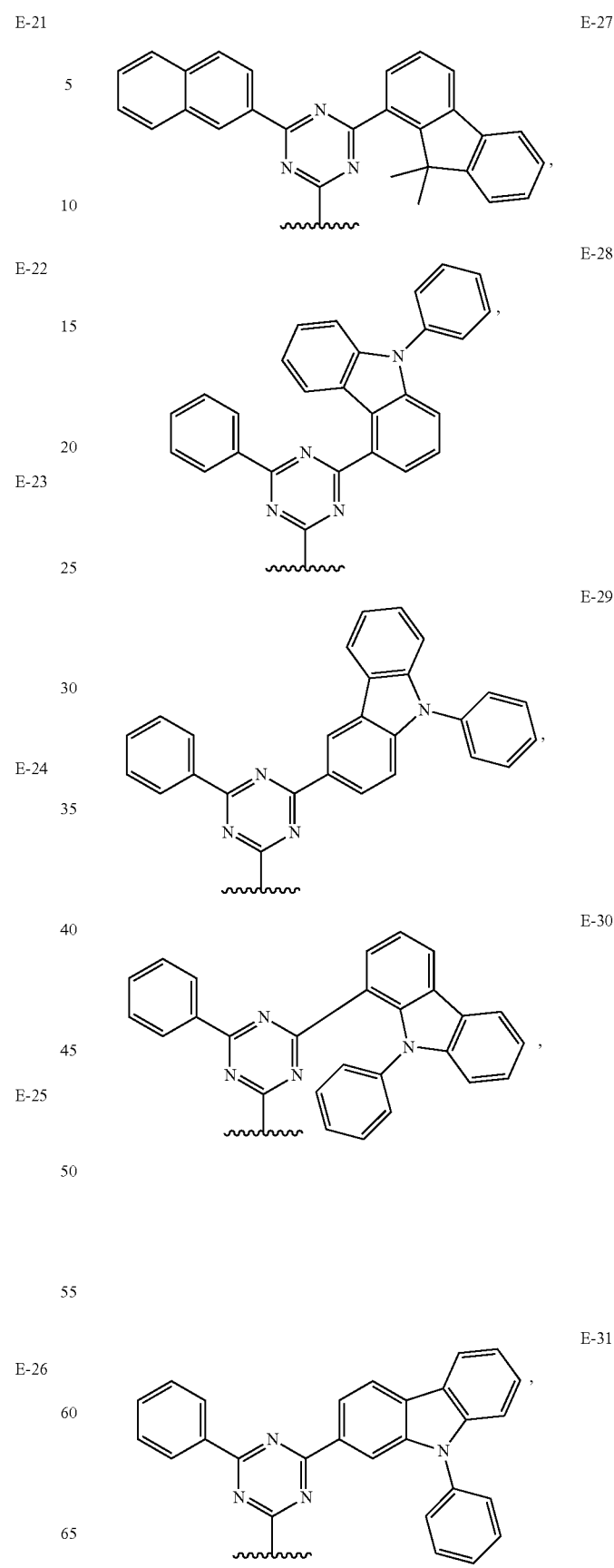

E-32 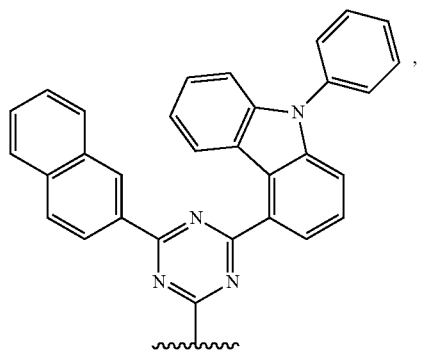
E-33 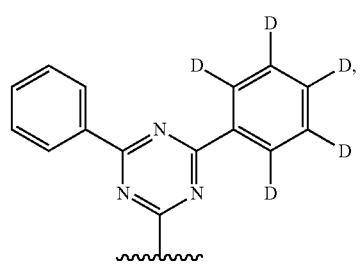
E-34 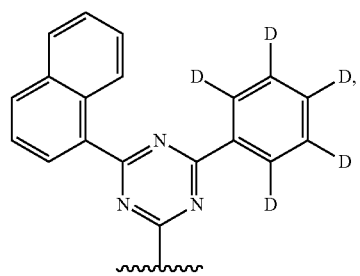
E-35 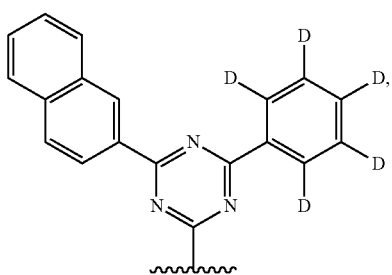
E-36 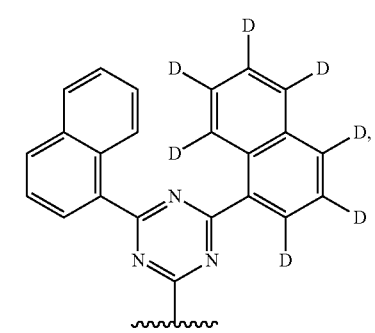
E-37 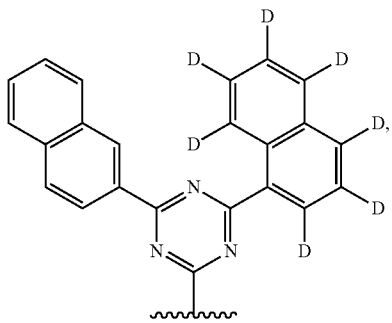
E-38 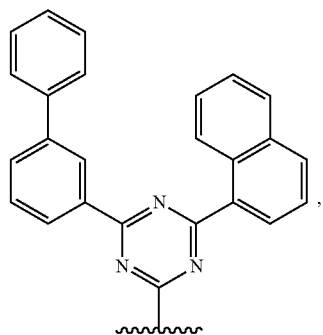
E-39 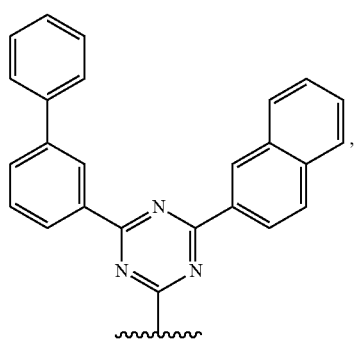
E-40 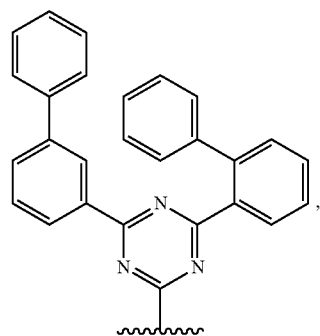

-continued
E-41
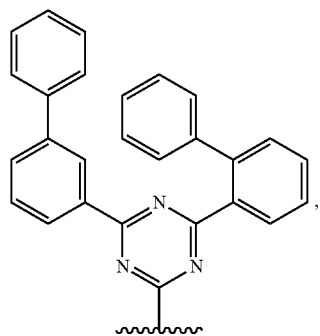
E-42
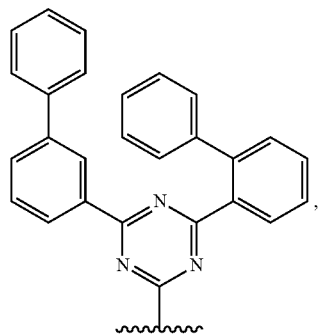
E-43
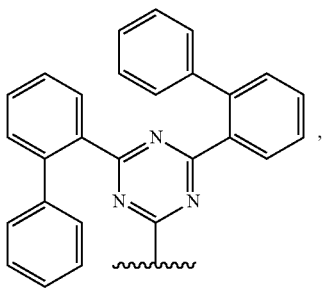
E-44
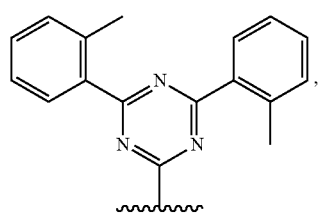
E-45
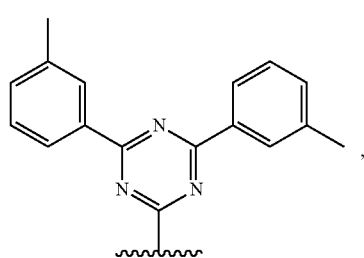
-continued
E-46
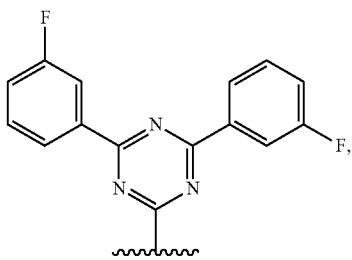
E-47
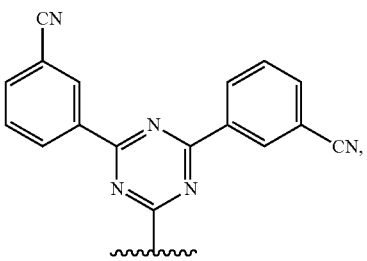
E-48
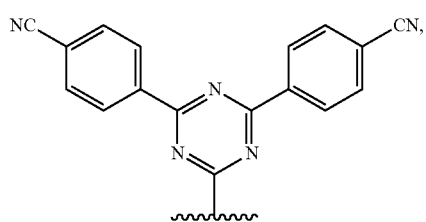
E-49
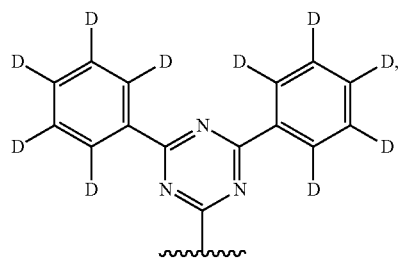
E-50
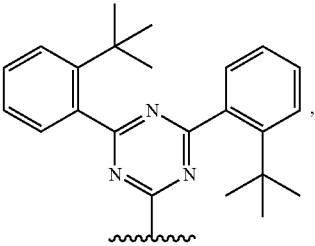
E-51
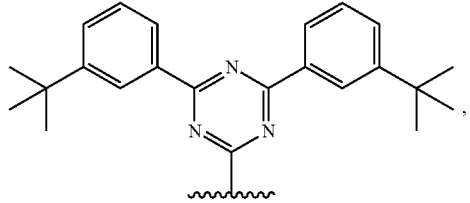

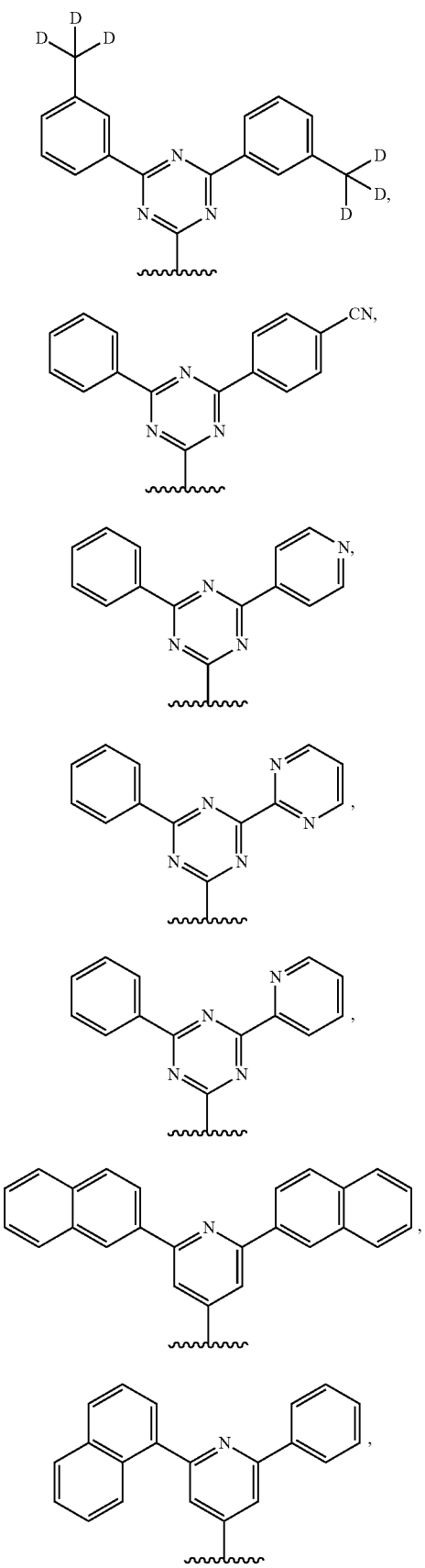
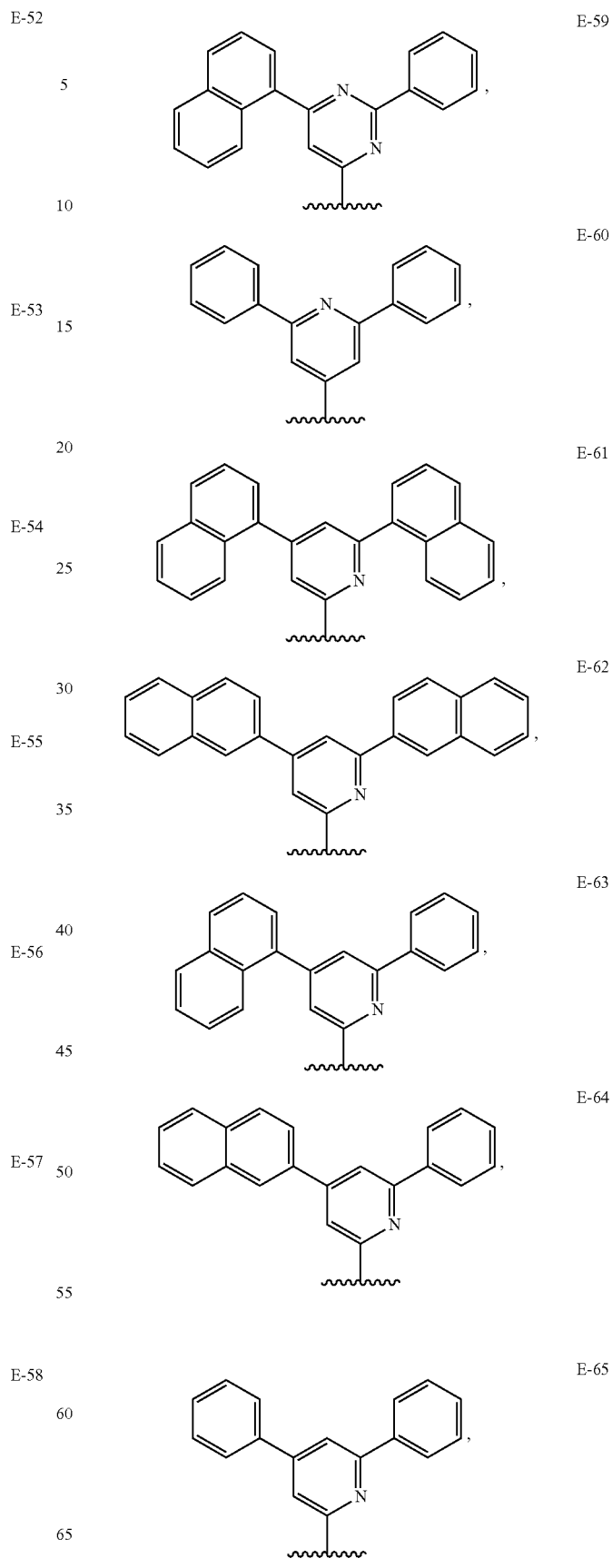

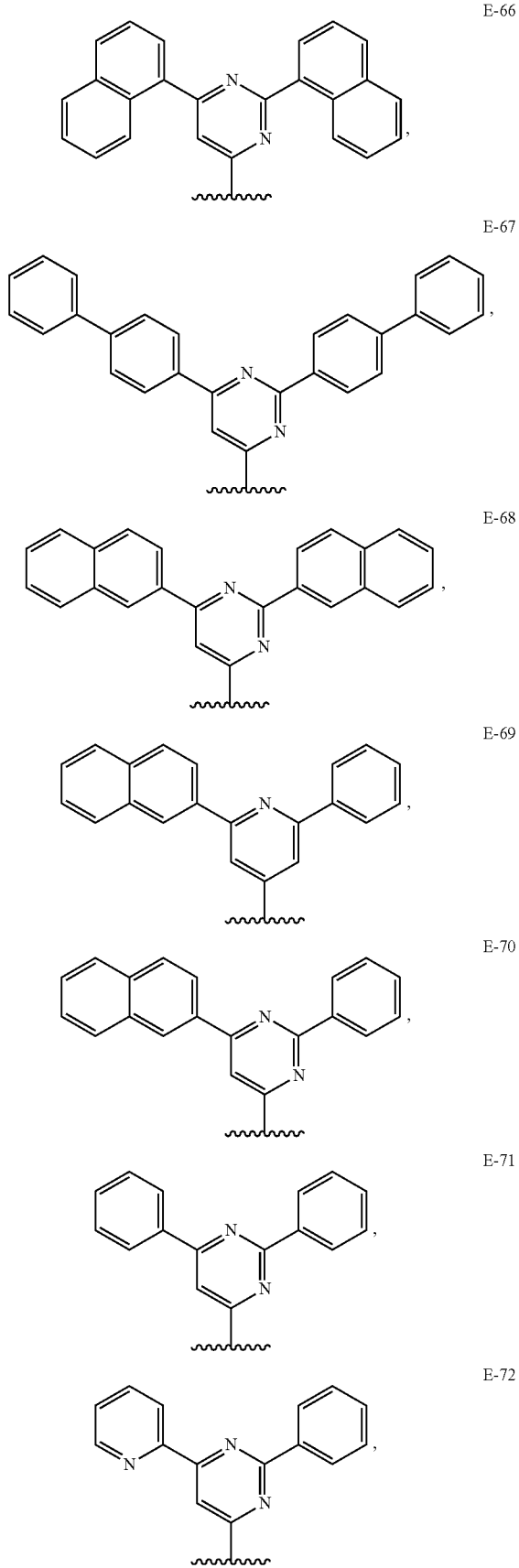

E-78
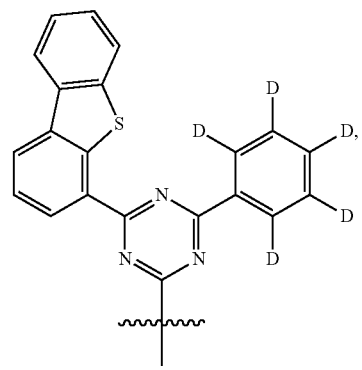

E-79
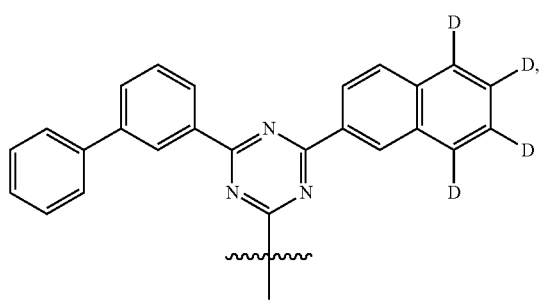

E-80
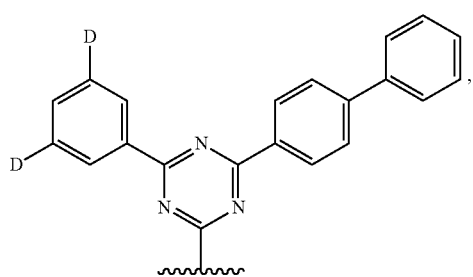

E-81
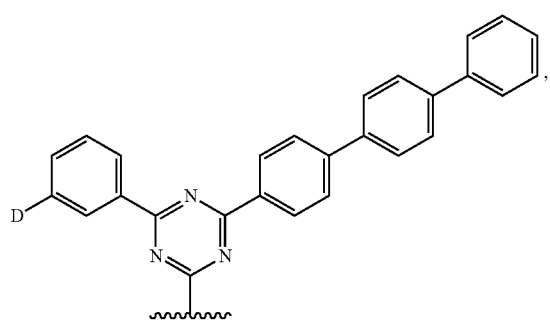

E-82
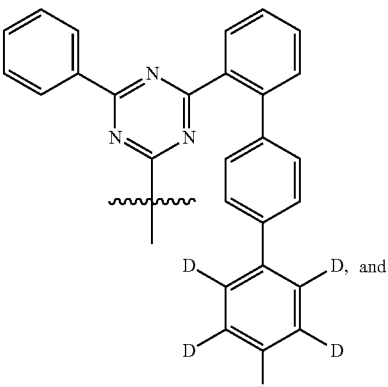

E-83
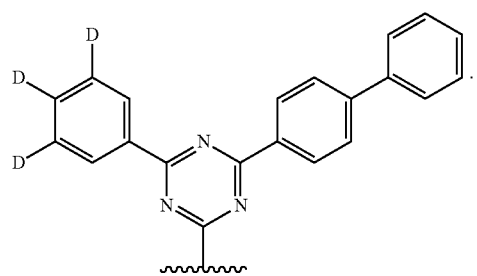

According to an embodiment of the present disclosure, wherein, the L has a structure represented by Formula 3:

Formula 3
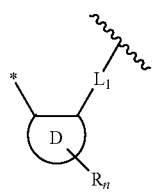

wherein the ring D is, at each occurrence identically or differently, selected from an aromatic ring having 6 to 18 carbon atoms or a heteroaromatic ring having 3 to 18 carbon atoms; $L_1$ is selected from a single bond, substituted or unsubstituted arylene having 6 to 30 carbon atoms, substituted or unsubstituted heteroarylene having 3 to 30 carbon atoms, or combinations thereof; and when $L_1$ is selected from substituted arylene having 6 to 30 carbon atoms or substituted heteroarylene having 3 to 30 carbon atoms, $L_1$ has a substituent $R_m$; and $R_m$ represents, at each occurrence identically or differently, mono-substitution or multiple substitutions;

$R_n$ and $R_m$ are, at each occurrence identically or differently, selected from the group consisting of: hydrogen, deuterium, halogen, substituted or unsubstituted alkyl having 1 to 20 carbon atoms, substituted or unsubstituted arylalkyl having 7 to 30 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, an isocyano group, a hydroxyl group, a sulfanyl group, and combinations thereof, adjacent substituents $R_n$, $R_m$ can be optionally joined to form a ring.

According to an embodiment of the present disclosure, wherein, in the Formula 3, the ring D is, at each occurrence identically or differently, selected from an aromatic ring having 6 to 12 carbon atoms or a heteroaromatic ring having 3 to 12 carbon atoms.

According to an embodiment of the present disclosure, wherein, in the Formula 3, $L_1$ is selected from a single bond, substituted or unsubstituted arylene having 6 to 12 carbon atoms, substituted or unsubstituted heteroarylene having 3 to 12 carbon atoms, or combinations thereof.

According to an embodiment of the present disclosure, wherein, in the Formula 3, the ring D is, at each occurrence identically or differently, selected from a benzene ring, a naphthalene ring, a phenanthrene ring, a fluorene ring, a triphenylene ring, a carbazole ring, a dibenzofuran ring, a dibenzothiophene ring, a pyridine ring, and combinations thereof, $L_1$ is selected from a single bond, substituted or unsubstituted phenylene, or substituted or unsubstituted naphthylene;

$R_n$ and $R_m$ are, at each occurrence identically or differently, selected from the group consisting of: hydrogen, deuterium, halogen, substituted or unsubstituted alkyl having 1 to 20 carbon atoms, substituted or unsubstituted arylalkyl having 7 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, a hydroxyl group, a sulfanyl group, and combinations thereof.

According to an embodiment of the present disclosure, wherein, in the Formula 3, $L_1$ is selected from a single bond.

According to an embodiment of the present disclosure, wherein, the L is selected from the group consisting of the following structures:

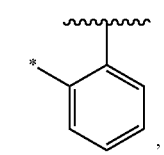

L-1

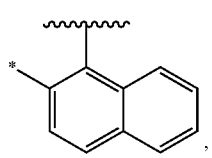

L-2

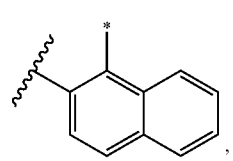

L-3

-continued

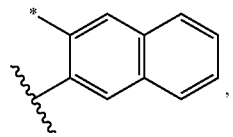

L-4

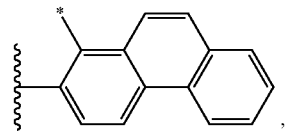

L-5

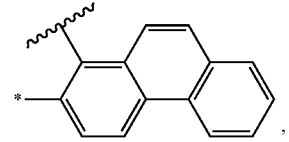

L-6

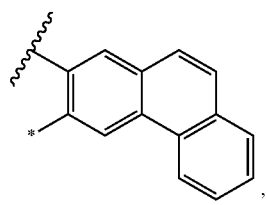

L-7

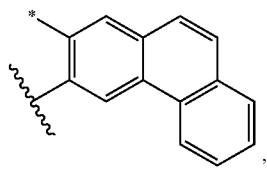

L-8

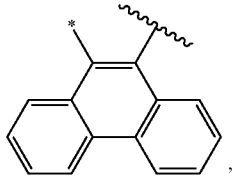

L-9

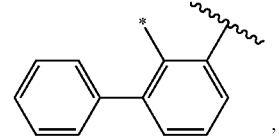

L-10

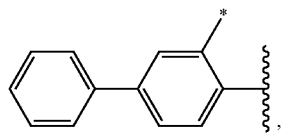

L-11

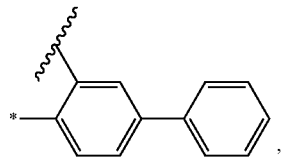

L-12

L-13 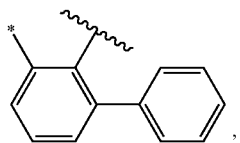
L-14 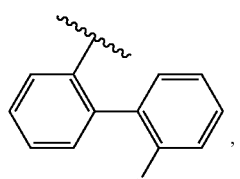
L-15 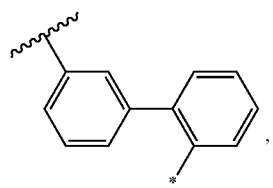
L-16 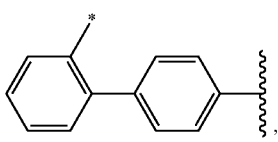
L-17 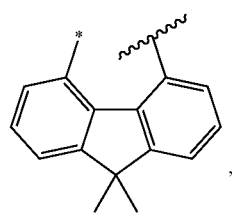
L-18 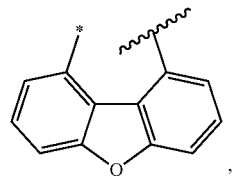
L-19 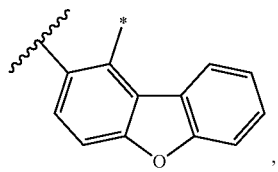
L-20 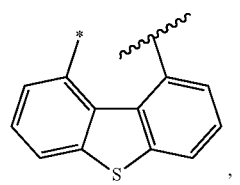
L-21 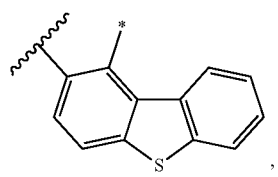
L-22 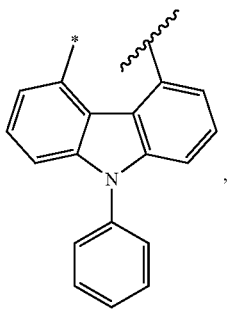
L-23 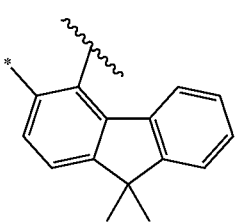
L-24 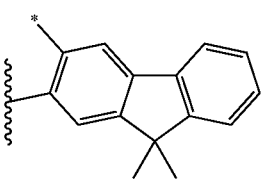
L-25 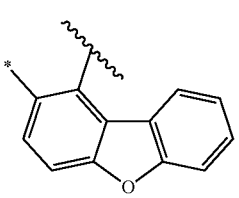
L-26 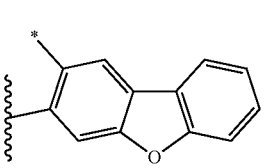
L-27 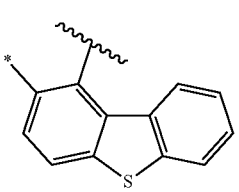
L-28 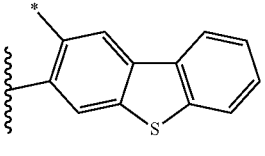

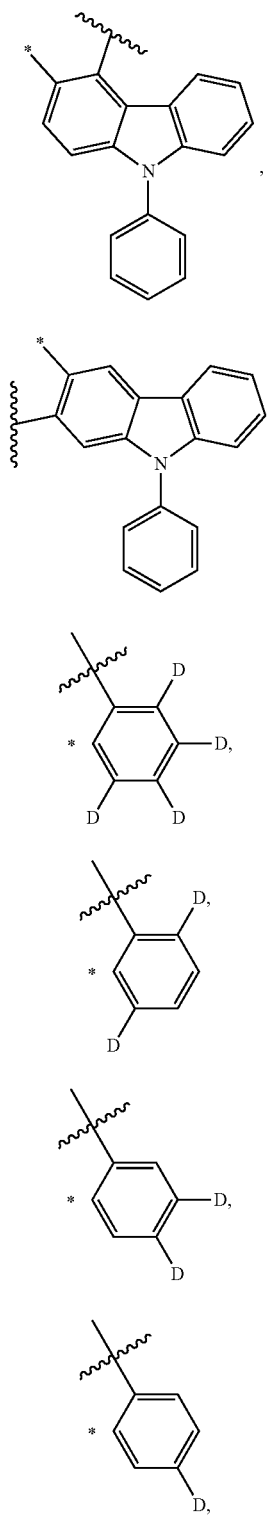

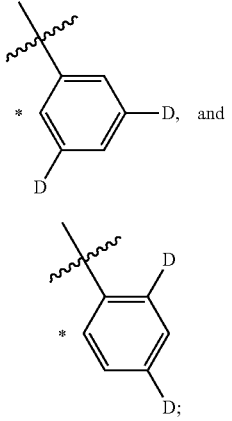

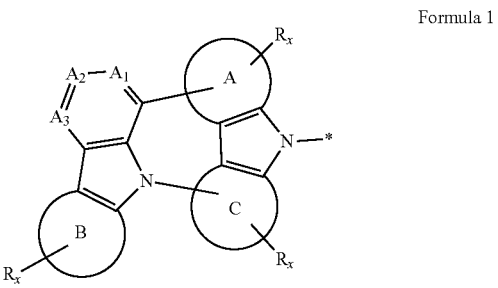

wherein in the structures of the L-1 to L-37, "*" represents the position the structures are connected to the structure H represented by Formula 1, and "〰" represents the position where the structures are connected to the structure E represented by Formula 2.

According to an embodiment of the present disclosure, wherein, hydrogens in the structures of the L-1 to L-37 can be partially or completely substituted with deuterium.

According to an embodiment of the present disclosure, wherein, the compound is selected from the group consisting of Compound 1 to Compound 1000, and the specific structures of Compound 1 to Compound 1000 are referred to claim 12.

According to an embodiment of the present disclosure, wherein, hydrogens in the Compound 1 to Compound 1000 can be partially or completely substituted by deuterium.

According to an embodiment of the present disclosure, disclosed is an electroluminescent device including:
an anode,
a cathode, and
an organic layer disposed between the anode and the cathode, wherein the organic layer comprises a compound having a structure of H-L-E; wherein H has a structure represented by Formula 1:

Formula 1 in Formula 1, $A_1$, $A_2$, and $A_3$ are, at each occurrence identically or differently, selected from N or CR, and the ring A, the ring B, and the ring C are, at each occurrence identically or differently, selected from a carbocyclic ring having 5 to 18 carbon atoms or a heterocyclic ring having 3 to 18 carbon atoms;

$R_x$ represents, at each occurrence identically or differently, mono-substitution, multiple substitutions, or non-substitution;

E has a structure represented by Formula 2:

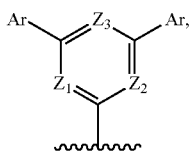

Formula 2

Ar is, at each occurrence identically or differently, selected from substituted or unsubstituted aryl having 6 to 30 carbon atoms or substituted or unsubstituted heteroaryl having 3 to 30 carbon atoms;

$Z_1$ to $Z_3$ are each independently selected from N or $CR_z$, and at least one of $Z_1$ to $Z_3$ is N;

L has a structure represented by Formula 3:

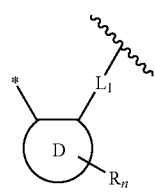

Formula 3 wherein the ring D is, at each occurrence identically or differently, selected from a carbocyclic ring having 5 to 18 carbon atoms or a heterocyclic ring having 3 to 18 carbon atoms;

$R_n$ represents, at each occurrence identically or differently, mono-substitution, multiple substitutions, or non-substitution;

wherein $L_1$ is selected from a single bond, substituted or unsubstituted arylene having 6 to 30 carbon atoms, substituted or unsubstituted heteroarylene having 3 to 30 carbon atoms, or combinations thereof; and when $L_1$ is selected from substituted arylene having 6 to 30 carbon atoms or substituted heteroarylene having 3 to 30 carbon atoms, $L_1$ has a substituent $R_m$; and $R_m$ represents, at each occurrence identically or differently, mono-substitution or multiple substitutions;

wherein R, $R_x$, $R_z$, $R_n$, and $R_m$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents R, $R_x$ can be optionally joined to form a ring;

adjacent substituents $R_n$, $R_m$ can be optionally joined to form a ring.

According to an embodiment of the present disclosure, wherein, in the electroluminescent device, the organic layer is an emissive layer, and the compound is a host material.

According to an embodiment of the present disclosure, wherein, in the electroluminescent device, the emissive layer further includes at least one phosphorescent material.

According to an embodiment of the present disclosure, wherein, in the electroluminescent device, the phosphorescent material is a metal complex, and the metal complex has a general formula of $M(L_a)_m(L_b)_n(L_c)_q$;

M is selected from a metal with a relative atomic mass greater than 40;

$L_a$, $L_b$, and $L_c$ are a first ligand, a second ligand, and a third ligand coordinated to the metal M, respectively; $L_a$, $L_b$, and $L_c$ can be optionally joined to form a multidentate ligand; for example, any two of $L_a$, $L_b$, and $L_c$ may be joined to form a tetradentate ligand; in another example, $L_a$, $L_b$, and $L_c$ may be joined to each other to form a hexadentate ligand; or in another example, none of $L_a$, $L_b$, and $L_c$ are joined to form a multidentate ligand;

$L_a$, $L_b$, and $L_c$ can be the same or different; m is 1, 2, or 3; n is 0, 1, or 2; q is 0 or 1; the sum of m, n, and q equals to the oxidation state of M; when m is greater than or equal to 2, the plurality of $L_a$ can be the same or different; and when n is equal to 2, two $L_b$ can be the same or different;

$L_a$ has a structure represented by Formula 4:

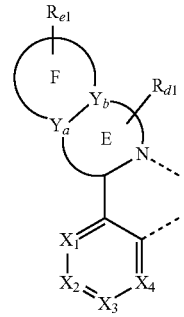

Formula 4 wherein, the ring E is a five-membered heteroaromatic ring or a six-membered heteroaromatic ring;

the ring F is selected from a five-membered unsaturated carbocyclic ring, a benzene ring, a five-membered heteroaromatic ring, or a six-membered heteroaromatic ring;

the ring E and the ring F are fused via $Y_a$ and $Y_b$;

$Y_a$ and $Y_b$ are, at each occurrence identically or differently, selected from C or N;

$R_{d1}$ and $R_{e1}$ represent, at each occurrence identically or differently, mono-substitution, multiple substitutions, or non-substitution;

$X_1$ to $X_4$ are, at each occurrence identically or differently, selected from $CR_{xx}$ or N;

$R_{d1}$, $R_{e1}$, and $R_{xx}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents $R_{d1}$, $R_{e1}$, $R_x$ can be optionally joined to form a ring;

$L_b$ and $L_c$ are each independently selected from any one of the following structures:

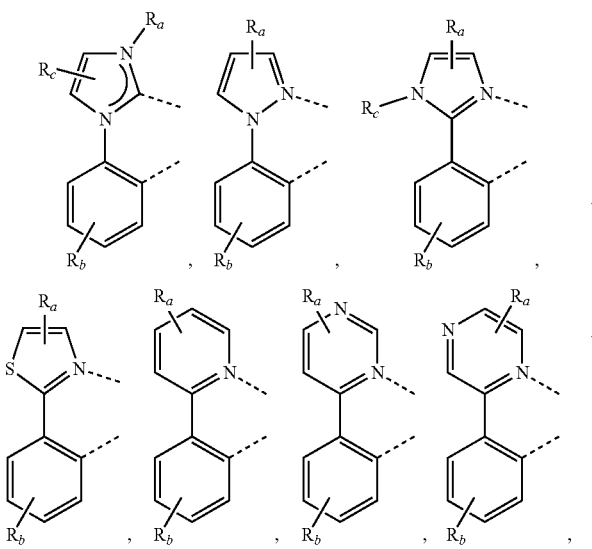

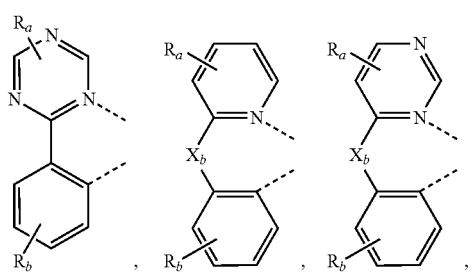

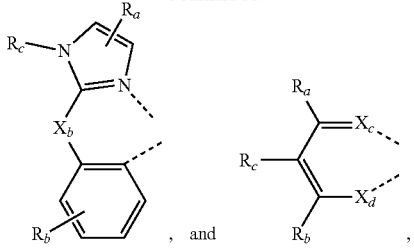

wherein, $R_a$, $R_b$, and $R_c$ represent, at each occurrence identically or differently, mono-substitution, multiple substitutions, or non-substitution;

$X_b$ is, at each occurrence identically or differently, selected from the group consisting of: O, S, Se, $NR_{N1}$, and $CR_{C1}R_{C2}$;

$X_c$ and $X_d$ are, at each occurrence identically or differently, selected from the group consisting of: O, S, Se, and $NR_{N2}$;

$R_a$, $R_b$, $R_c$, $R_{N1}$, $R_{N2}$, $R_{C1}$, and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

in structures of the ligands $L_b$ and $L_c$, adjacent substituents $R_a$, $R_b$, $R_c$, $R_{N1}$, $R_{N2}$, $R_{C1}$, and $R_{C2}$ can be optionally joined to form a ring.

In the present disclosure, the expression that adjacent substituents $R_{d1}$, $R_{e1}$, $R_x$ can be optionally joined to form a ring is intended to mean that when there are substituents $R_{d1}$, substituents $R_{e1}$, and substituents $R_{xx}$, any one or more of groups of adjacent substituents, for example, adjacent substituents $R_{d1}$, adjacent substituents $R_{e1}$, adjacent substituents $R_{xx}$ adjacent substituents $R_{d1}$ and $R_{e1}$, adjacent substituents $R_{d1}$ and $R_{xx}$ and adjacent substituents $R_{e1}$ and $R_{xx}$, can be joined to form a ring. Obviously, in the presence of substituents $R_{d1}$, substituents $R_{e1}$, and substituents $R_{xx}$ it is possible that none of these groups of substituents are joined to form a ring.

In the present embodiment, the expression that adjacent substituents $R_a$, $R_b$, $R_c$, $R_{N1}$, $R_{N2}$, $R_{C1}$, and $R_{C2}$ can be optionally joined to form a ring is intended to mean that any one or more of groups of adjacent substituents, for example, two substituents $R_a$, two substituents $R_b$, two substituents Re, substituents $R_a$ and $R_b$, substituents $R_a$ and Re, substituents $R_b$ and Re, substituents $R_a$ and $R_{N1}$, substituents $R_b$ and $R_{N1}$, substituents $R_a$ and $R_{C1}$, substituents $R_a$ and $R_{C2}$, substituents $R_b$ and $R_{C1}$, substituents $R_b$ and $R_{C2}$, substituents $R_a$ and $R_{N2}$, substituents $R_b$ and $R_{N2}$, and substituents $R_{C1}$ and $R_{C2}$, may be joined to form a ring. Obviously, it is possible that none of these groups of substituents are joined to form a ring.

According to an embodiment of the present disclosure, in the device, wherein the $L_a$ has a structure represented by any one of Formula 4-1 to Formula 4-5:

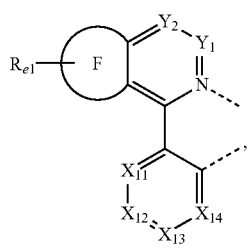

Formula 4-1

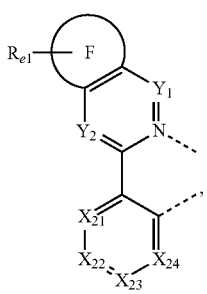

Formula 4-2

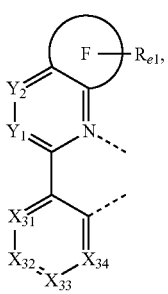

Formula 4-3

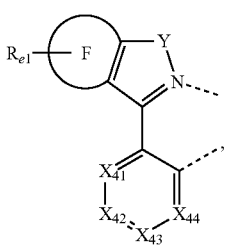

Formula 4-4

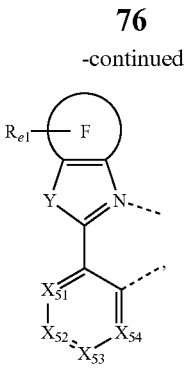

Formula 4-5 the ring F is selected from an unsaturated ring having 5 to 10 ring atoms; preferably, the ring F is selected from a 5-membered unsaturated carbocyclic ring, a benzene ring, or a 5-6-membered heteroaromatic ring;

$R_{e1}$ represents, at each occurrence identically or differently, mono-substitution, multiple substitutions, or non-substitution;

$X_{11}$ to $X_{14}$ are, at each occurrence identically or differently, selected from $CR_{x1}$ or N; $X_{21}$ to $X_{24}$ are, at each occurrence identically or differently, selected from $CR_{x2}$ or N; $X_{31}$ to $X_{34}$ are, at each occurrence identically or differently, selected from $CR_{x3}$ or N; $X_{41}$ to $X_{44}$ are, at each occurrence identically or differently, selected from $CR_{x4}$ or N; and $X_{51}$ to $X_{54}$ are, at each occurrence identically or differently, selected from $CR_{x5}$ or N;

$Y_1$ and $Y_2$ are, at each occurrence identically or differently, selected from $CR_{d1}$ or N;

Y is, at each occurrence identically or differently, selected from the group consisting of O, S, Se, $NR_d$, $CR_dR_d$, and $SiR_dR_d$; when there are two $R_d$ presented at the same time, the two R may be the same or different; and preferably, Y is, at each occurrence identically or differently, selected from O or S;

$R_{x1}$, $R_{x2}$, $R_{x3}$, $R_{x4}$, $R_{x5}$, $R_d$, $R_{d1}$, and $R_{e1}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof, adjacent substituents $R_{x1}$, $R_{x2}$, $R_{x4}$, $R_{x5}$, $R_d$, $R_{d1}$, and $R_{e1}$ can be optionally joined to form a ring;

when $R_{x3}$ is, at each occurrence identically or differently, selected from the group consisting of: substituted or unsubstituted alkyl having 1 to 20 carbon atoms, substituted or unsubstituted cycloalkyl having 3 to 20 ring carbon atoms, substituted or unsubstituted arylalkyl having 7 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and substituted or unsubstituted amino having 0 to 20 carbon atoms, adjacent substituents $R_{x3}$ can be optionally joined to form a ring.

In the present disclosure, the expression that adjacent substituents $R_{x1}$, $R_z$, $R_{x4}$, $R_{x5}$, $R_d$, $R_{d1}$, and $R_{e1}$ can be optionally joined to form a ring is intended to mean that when there are substituents $R_{x1}$, substituents $R_{x2}$, substituents $R_{x4}$, substituents $R_{x5}$, substituents $R_d$, substituents $R_{d1}$, and substituents $R_{e1}$, any one or more of groups of adjacent substituents, for example, adjacent substituents $R_{x1}$, adjacent substituents $R_{x2}$, adjacent substituents $R_{x4}$, adjacent substituents $R_{x5}$, adjacent substituents $R_d$, substituents $R_{x1}$ and $R_{e1}$, substituents $R_{x2}$ and $R_{d1}$, substituents $R_{x2}$ and $R_{e1}$, adjacent substituents $R_{x4}$ and $R_{e1}$, substituents $R_{x5}$ and $R_d$, and substituents $R_{d1}$ and $R_{e1}$, can be joined to form a ring. Obviously, it is possible that none of these groups of substituents are joined to form a ring.

In the present disclosure, the expression that adjacent substituents $R_{x3}$ can optionally be joined to form a ring when $R_{x3}$ is selected form the group of adjacent substituents is intended to indicate that only when there are a plurality of substituents $R_{x3}$ and the plurality of substituents $R_{x3}$ are selected from the group of substituents consisting of alkyl, cycloalkyl, arylalkyl, alkenyl, aryl, heteroaryl, alkylsilyl, arylsilyl, and amino, can adjacent substituents $R_{x3}$ be joined to form a ring, while when the substituent $R_{x3}$ is selected from a substituent other than substituents in the above-mentioned group of adjacent substituents, adjacent substituents $R_{x3}$ cannot be joined to form a ring. Obviously, when the substituent $R_{x3}$ is selected from the above-mentioned group of adjacent substituents, it is possible that adjacent substituents $R_{x3}$ are not joined to form a ring.

According to an embodiment of the present disclosure, in the device, the $L_a$ has a structure represented by any one of Formula 4-6 to Formula 4-13:

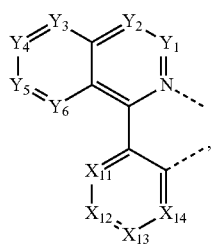

Formula 4-6

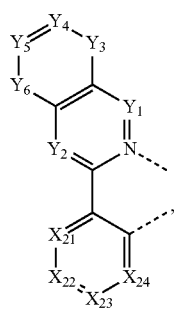

Formula 4-7

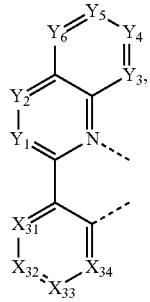

Formula 4-8

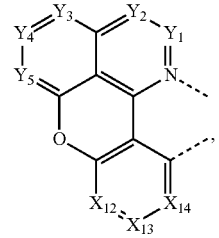

Formula 4-9

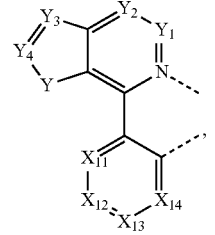

Formula 4-10

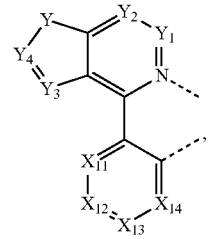

Formula 4-11

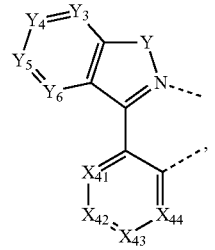

Formula 4-12

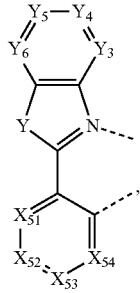

Formula 4-13

$X_{11}$ to $X_{14}$ are, at each occurrence identically or differently, selected from $CR_{x3}$ or N; $X_{21}$ to $X_{24}$ are, at each occurrence identically or differently, selected from $CR_{x3}$ or N; $X_{41}$ to $X_{44}$ are, at each occurrence identically or differently, selected from $CR_{x5}$ or N;

$Y_1$ and $Y_2$ are, at each occurrence identically or differently, selected from $CR_{d1}$ or N;

$Y_3$, $Y_4$, $Y_5$ and $Y_6$ are, at each occurrence identically or differently, selected from $CR_{e1}$ or N;

Y is, at each occurrence identically or differently, selected from the group consisting of O, S, Se, $NR_d$, $CR_dR_d$, and $SiR_dR_d$; when there are two $R_d$ presented at the same time, the two $R_d$ may be the same or different; for example, when Y is selected from $CR_dR_d$, the two $R_d$ may be the same or different; in another example, when Y is selected from $SiR_dR_d$, the two $R_d$ may be the same or different;

preferably, Y is, at each occurrence identically or differently, selected from O or S;

$R_{x1}$, $R_{x2}$, $R_{x3}$, $R_{x4}$, $R_{x5}$, $R_d$, $R_{d1}$, and $R_{e1}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof, adjacent substituents $R_{x1}$, $R_{x2}$, $R_{x4}$, $R_{x5}$, $R_d$, $R_{d1}$, and $R_{e1}$ can be optionally joined to form a ring;

when $R_{x3}$ is, at each occurrence identically or differently, selected from the group consisting of: substituted or unsubstituted alkyl having 1 to 20 carbon atoms, substituted or unsubstituted cycloalkyl having 3 to 20 ring carbon atoms, substituted or unsubstituted arylalkyl having 7 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and substituted or unsubstituted amino having 0 to 20 carbon atoms, adjacent substituents $R_{x3}$ can be optionally joined to form a ring.

According to an embodiment of the present disclosure, in the device, wherein, in Formula 4-6 to Formula 4-13, $Y_1$ and/or $Y_2$ are/is selected from $CR_{d1}$; at least one or two of $Y_3$ to $Y_6$ are selected from $CR_{e1}$; and the $R_{d1}$ and $R_{e1}$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

According to an embodiment of the present disclosure, in the device, wherein, in Formula 4-6 to Formula 4-13, $Y_4$ and/or $Y_5$ are/is each independently selected from $CR_{e1}$; and the $R_{e1}$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

According to an embodiment of the present disclosure, in the device, wherein, in Formula 4-6 to Formula 4-13, at least one or two of $X_{11}$ to $X_{14}$ are selected from $CR_{x1}$, at least one or two of $X_{21}$ to $X_{24}$ are selected from $CR_{x2}$, at least one or two of $X_{31}$ to $X_{34}$ are selected from $CR_{x3}$, at least one or two of $X_{41}$ to $X_{44}$ are selected from $CR_{x4}$, and at least one or two of $X_{51}$ to $X_{54}$ are selected from $CR_{x5}$; and the $R_{x1}$, $R_{x2}$, $R_{x3}$, $R_{x4}$, and $R_{x5}$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

According to an embodiment of the present disclosure, in the device, in Formula 4-6 to Formula 4-13, $X_{12}$ and/or $X_{14}$ are selected from $CR_{x1}$, $X_{22}$ and/or $X_{24}$ are selected from $CR_{x2}$, $X_{32}$ and/or $X_{34}$ are selected from $CR_{x3}$, $X_{42}$ and/or $X_{44}$ are selected from $CR_{x4}$, and $X_{52}$ and/or $X_{54}$ are selected from $CR_{x5}$; and the $R_{x1}$, $R_{x2}$, $R_{x3}$, $R_{x4}$, and $R_{x5}$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

According to an embodiment of the present disclosure, in the device, in Formula 4-6 to Formula 4-13, $X_{12}$ and/or $X_{14}$ are/is selected from $CR_{x1}$, $X_{22}$ and/or $X_{24}$ are/is selected from $CR_{x2}$, $X_{32}$ and/or $X_{34}$ are/is selected from $CR_{x3}$, $X_{42}$ and/or $X_{44}$ are/is selected from $CR_{x4}$, and $X_{52}$ and/or $X_{54}$ are/is selected from $CR_{x5}$; and the $R_{x1}$, $R_{x2}$, $R_{x3}$, $R_{x4}$, and $R_{x5}$ are, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof.

According to an embodiment of the present disclosure, in the device, in Formula 4-6 to Formula 4-13, $X_{11}$ to $X_{14}$ are, at each occurrence identically or differently, selected from $CR_{x1}$; $X_{21}$ to $X_{24}$ are, at each occurrence identically or differently, selected from $CR_{x2}$; $X_{31}$ to $X_{34}$ are, at each occurrence identically or differently, selected from $CR_{x3}$; $X_{41}$ to $X_{44}$ are, at each occurrence identically or differently, selected from $CR_{x4}$; $X_{51}$ to $X_{54}$ are, at each occurrence identically or differently, selected from $CR_{x5}$; $Y_1$ and $Y_2$ are, at each occurrence identically or differently, selected from $CR_{d1}$; $Y_3$, $Y_4$, $Y_5$ and $Y_6$ are, at each occurrence identically or differently, selected from $CR_{e1}$; and $R_{x1}$, $R_{x2}$, $R_{x3}$, $R_{x4}$, $R_{x5}$, $R_{d1}$, and $R_{e1}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

According to an embodiment of the present disclosure, in the device, in Formula 4-6 to Formula 4-13, $X_{11}$ to $X_{14}$ are, at each occurrence identically or differently, selected from $CR_{x1}$; $X_{21}$ to $X_{24}$ are, at each occurrence identically or differently, selected from $CR_{x2}$; $X_{31}$ to $X_{34}$ are, at each occurrence identically or differently, selected from $CR_{x3}$; $X_{41}$ to $X_{44}$ are, at each occurrence identically or differently, selected from $CR_{x4}$; $X_{51}$ to $X_{54}$ are, at each occurrence identically or differently, selected from $CR_{x5}$; $Y_1$ is, at each occurrence identically or differently, selected from $CR_{d1}$; $Y_2$ is, at each occurrence identically or differently, selected from N; $Y_3$, $Y_4$, $Y_5$ and $Y_6$ are, at each occurrence identically or differently, selected from $CR_{e1}$; and $R_{x1}$, $R_{x2}$, $R_{x3}$, $R_{x4}$, $R_{x5}$, $R_{d1}$, and $R_{e1}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

According to an embodiment of the present disclosure, in the device, wherein the ligand $L_b$ has the following structure:

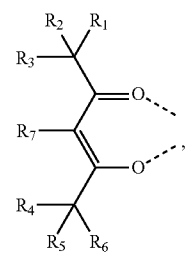

wherein $R_1$ to $R_7$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

According to an embodiment of the present disclosure, in the device, wherein the ligand $L_b$ has the following structure:

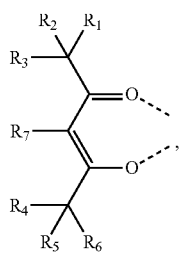

wherein at least one of $R_1$ to $R_3$ is selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof, and/or at least one of $R_4$ to $R_6$ is selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof.

According to an embodiment of the present disclosure, in the device, wherein the ligand $L_b$ has the following structure:

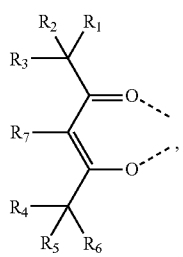

wherein at least two of $R_1$ to $R_3$ are, at each occurrence identically or differently, selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof; and/or at least two of $R_4$ to $R_6$ are, at each occurrence identically or differently, selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof.

According to an embodiment of the present disclosure, in the device, wherein the ligand $L_b$ has the following structure:

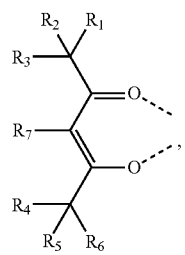

wherein at least two of $R_1$ to $R_3$ are, at each occurrence identically or differently, selected from substituted or unsubstituted alkyl having 2 to 20 carbon atoms, substituted or unsubstituted cycloalkyl having 3 to 20 ring carbon atoms, substituted or unsubstituted heteroalkyl having 2 to 20 carbon atoms, or combinations thereof; and/or at least two of $R_4$ to $R_6$ are, at each occurrence identically or differently, selected from substituted or unsubstituted alkyl having 2 to 20 carbon atoms, substituted or unsubstituted cycloalkyl having 3 to 20 ring carbon atoms, substituted or unsubstituted heteroalkyl having 2 to 20 carbon atoms, or combinations thereof.

According to an embodiment of the present disclosure, in the device, wherein the phosphorescent material is an Ir complex, a Pt complex or an Os complex.

According to an embodiment of the present disclosure, in the device, wherein the phosphorescent material is an Ir complex and has a structure represented by any one of: $Ir(L_a)(L_b)(L_c)$, $Ir(L_a)_2(L_b)$, $Ir(L_a)_2(L_c)$, or $Ir(L_a)(L_c)_2$.

According to another embodiment of the present disclosure, a compound formulation is further disclosed, which comprises the compound having a structure of H-L-E. The specific structure of the compound is shown in any one of the embodiments described above.

According to another embodiment of the present disclosure, a display assembly is further disclosed, which comprises the organic electroluminescent device whose organic layer includes the compound having a structure of H-L-E.

Combination with Other Materials

The materials described in the present disclosure for a particular layer in an organic light emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, compounds disclosed herein may be used in combination with a wide variety of hosts, transporting layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this present disclosure.

Material Synthesis Example

The method for preparing the compound of the present disclosure is not limited herein. Typically, the following compounds are used as examples without limitations, and synthesis routes and preparation methods thereof are described below.

Synthesis Example 1: Synthesis of Compound 1

Step 1: Synthesis of Intermediate 1

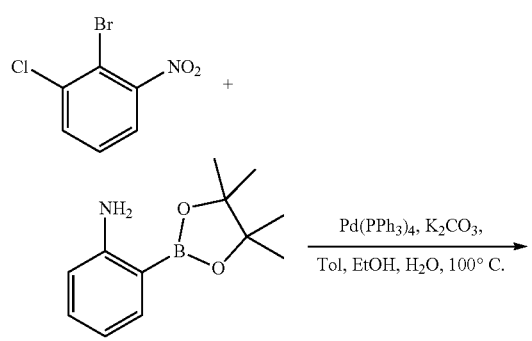

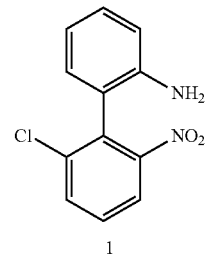

Under nitrogen protection, 2-bromo-3-chloronitrobenzene (100 g, 425.5 mmol), 2-aminophenylboronic acid pinacol ester (102 g, 468.1 mmol), tetrakis(triphenylphosphine) palladium (4.9 g, 4.25 mmol), potassium carbonate (115 g, 852 mmol), toluene (1000 mL), water (200 mL), and ethanol (200 mL) were added to a three-necked flask and reacted at 100° C. for 48 hours. After the reaction was completed, the reaction solution was cooled to room temperature, concentrated to remove the solvents, and added with distilled water. The mixture was extracted with ethyl acetate. The organic phases were washed with water, dried over anhydrous magnesium sulfate, concentrated to remove the solvents, and purified by column chromatography (PE/EA=4:1) to obtain Intermediate 1 as a yellow oil (90 g, with a yield of 85%).

Step 2: Synthesis of Intermediate 2

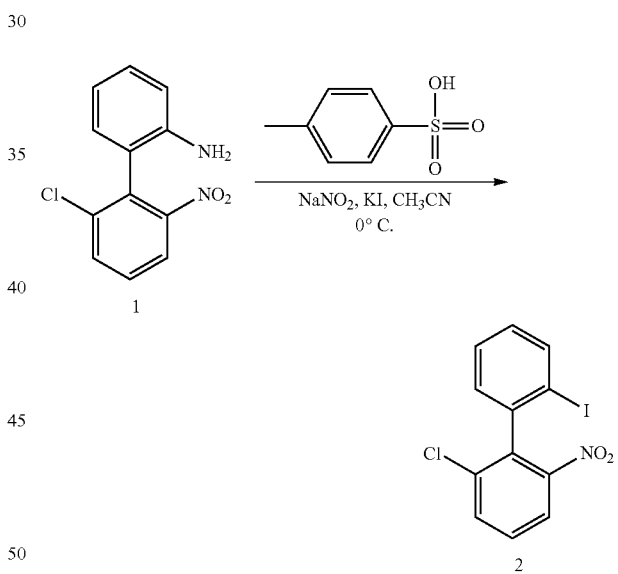

Intermediate 1 (90 g, 363 mmol) and acetonitrile (1000 mL) were respectively put into a three-necked flask. p-Toluenesulfonic acid (193.2 g, 1088 mmol) was added in portions at 0° C. and stirred for 30 minutes. At this temperature, an aqueous solution of the mixture of sodium nitrite (69 g, 726 mmol) and potassium iodide (150.6 g, 907 mmol) was slowly added dropwise. After the dropwise addition was completed, the mixture was slowly warmed to room temperature and reacted for 12 hours. After the reaction was completed, a saturated aqueous solution of sodium thiosulfate was added dropwise to quench the reaction. The reaction solution was concentrated and diluted with water. The mixed solution was extracted three times with ethyl acetate. The organic phases were dried over anhydrous sodium sulfate and concentrated to remove the solvents, and the mixture was isolated by column chromatography (PE/DCM=10/1) to obtain Intermediate 2 as a yellow solid (85 g, with a yield of 65%).

Step 3: Synthesis of Intermediate 4

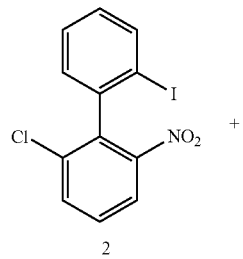

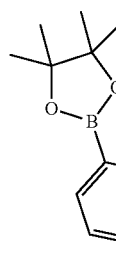

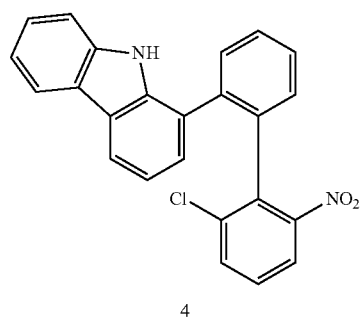

Under nitrogen protection, Intermediate 2 (20 g, 55.7 mmol), Intermediate 3 (24.5 g, 83.6 mmol), tetrakis(triphenylphosphine)palladium (1.9 g, 1.67 mmol), potassium carbonate (15.4 g, 111.4 mmol), tetrahydrofuran (500 mL), water (100 mL), and ethanol (100 mL) were added to a three-necked flask and reacted at 70° C. for 48 hours. After the reaction was completed, the reaction solution was cooled to room temperature, concentrated to remove the solvents, and added with distilled water. The mixture was extracted with ethyl acetate. The organic phases were washed with water, dried over anhydrous magnesium sulfate, concentrated to remove the solvents, and purified by column chromatography (PE/EA=4:1) to obtain Intermediate 4 as a yellow solid (12 g, with a yield of 55%).

Step 4: Synthesis of Intermediate 5

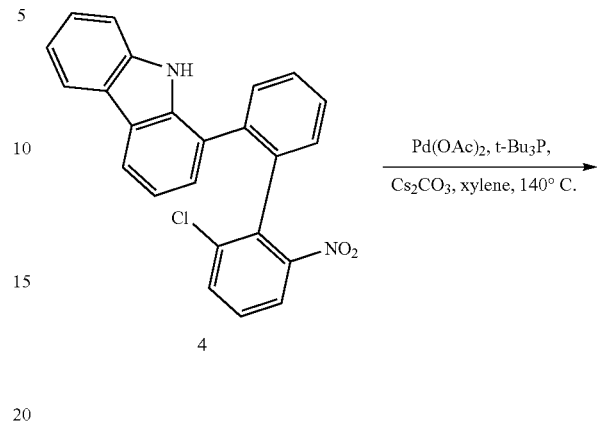

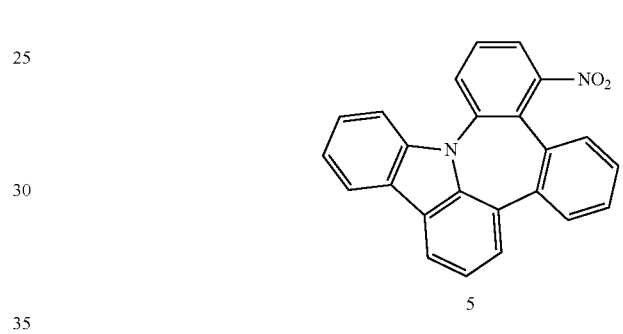

Under nitrogen protection, Intermediate 4 (12 g, 30.15 mmol), palladium acetate (338 mg, 1.5 mmol), tri-t-butylphosphine (606 mg, 3.0 mmol), cesium carbonate (20 g, 60.3 mmol), and xylene (230 mL) were added to a three-necked flask and reacted at 140° C. for 10 hours. After the reaction was completed, the reaction solution was cooled to room temperature, concentrated to remove the solvents, and added with distilled water. The mixture was extracted with ethyl acetate. The organic phases were washed with water, dried over anhydrous magnesium sulfate, concentrated to remove the solvents, and purified by column chromatography (PE/EA=6:1) to obtain Intermediate 5 as a yellow solid (9 g, with a yield of 80%).

Step 5: Synthesis of Intermediate 6

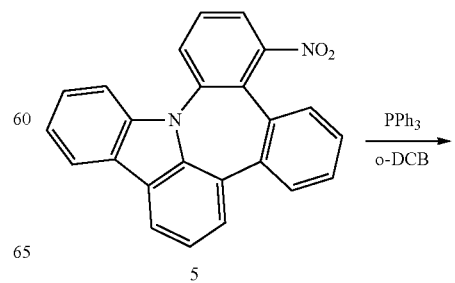

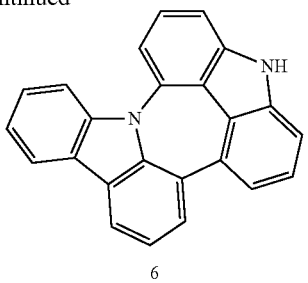

6

Under nitrogen protection, Intermediate 5 (9 g, 24.9 mmol), triphenylphosphine (19.6 g, 74.7 mmol) and o-dichlorobenzene (o-DCB) (100 mL) were added to a three-necked flask and reacted at 200° C. for 12 hours. After the reaction was completed, the reaction solution was concentrated to remove the solvents, and the crude product was isolated by column chromatography to obtain Intermediate 6 as a yellow solid (7 g, with a yield of 85%).

Step 6: Synthesis of Intermediate 7

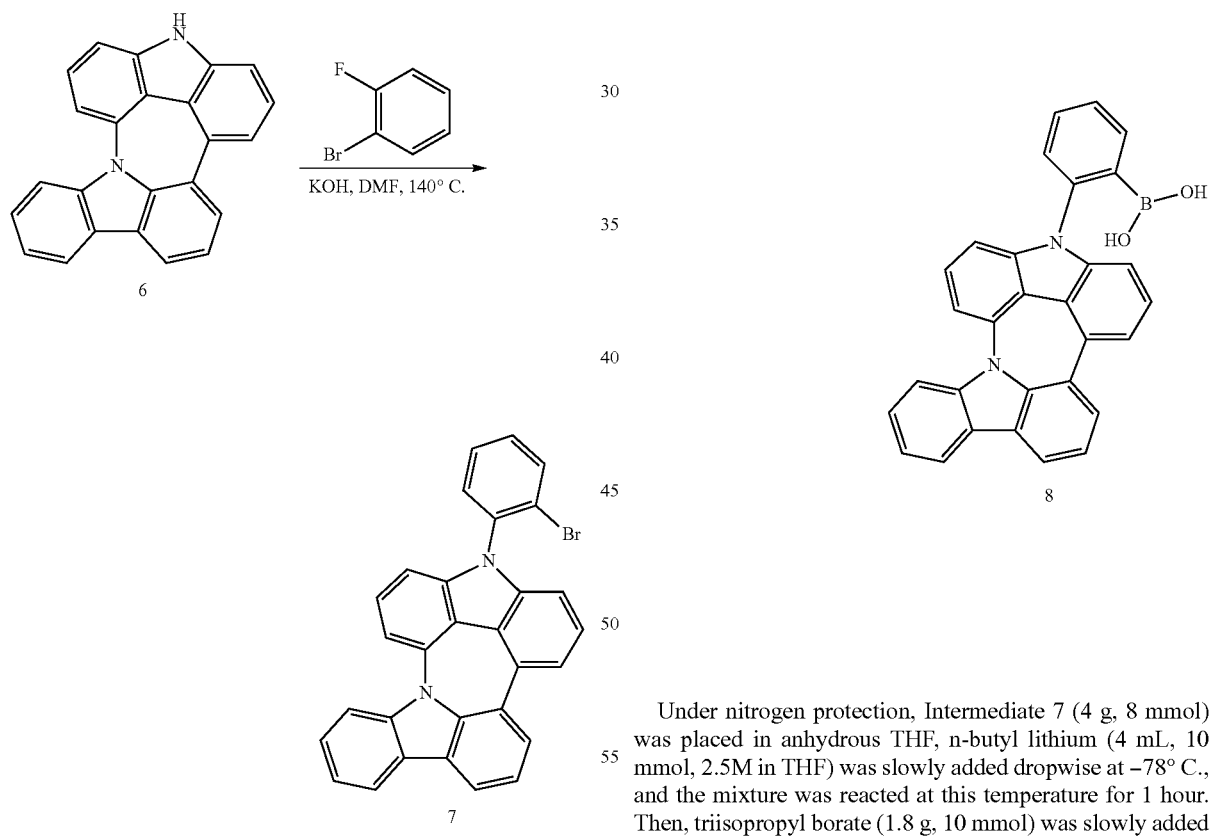

Under nitrogen protection, Intermediate 6 (4 g, 12.12 mmol), o-bromofluorobenzene (2.5 g, 14.5 mmol), potassium hydroxide (1.3 g, 24.24 mmol), and DMF (100 mL) were added to a three-necked flask and reacted at 140° C. for 24 hours. After the reaction was completed, the reaction solution was cooled to room temperature and added with distilled water. The mixture was extracted with ethyl acetate. The organic phases were washed with water and concentrated to remove the solvents, and the crude product was purified by column chromatography (with PE/DCM=4/1) to obtain Intermediate 7 as a yellow solid (4.3 g, with a yield of 72%).

Step 7: Synthesis of Intermediate 8

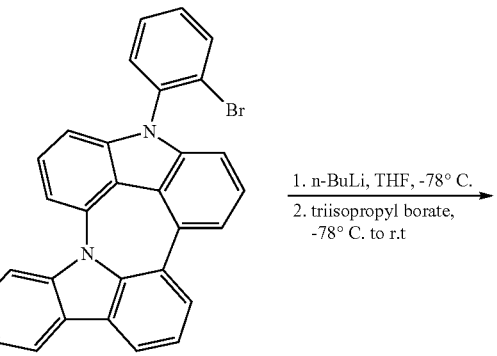

Under nitrogen protection, Intermediate 7 (4 g, 8 mmol) was placed in anhydrous THF, n-butyl lithium (4 mL, 10 mmol, 2.5M in THF) was slowly added dropwise at −78° C., and the mixture was reacted at this temperature for 1 hour. Then, triisopropyl borate (1.8 g, 10 mmol) was slowly added dropwise into the reaction system, and the reaction was continued for 1 hour and then slowly heated to room temperature. After the reaction was completed, the reaction solution was quenched with dilute hydrochloric acid and concentrated to remove the solvents. The crude product was extracted three times with DCM. The organic phases were washed with water and concentrated to remove the solvents, and the crude product was recrystallized from PE to obtain Intermediate 8 as a yellow solid (3 g, with a yield of 83%).

Step 8: Synthesis of Compound 1

Synthesis Example 2: Synthesis of Compound 9

Step 1: Synthesis of Intermediate 9

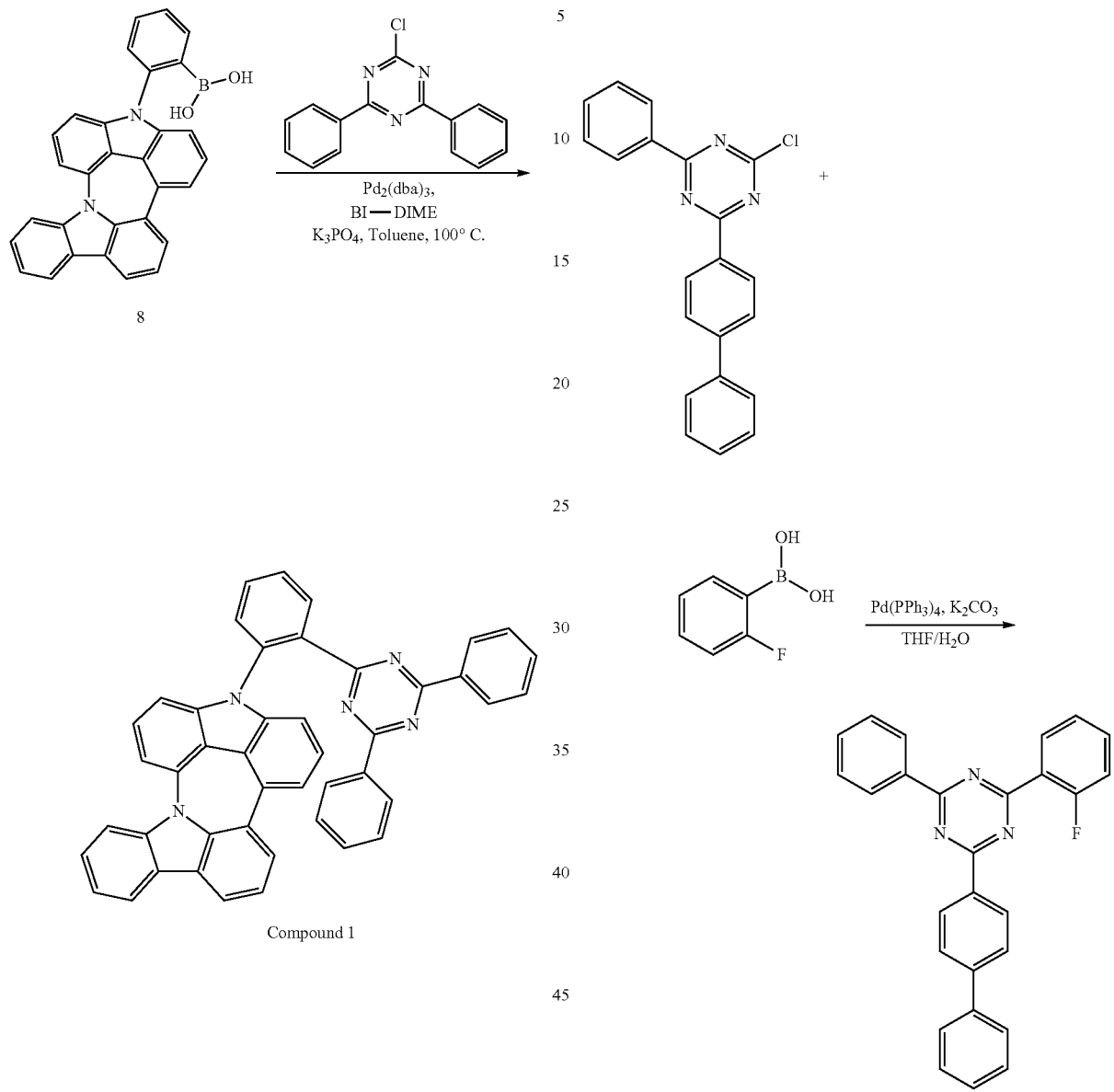

Under nitrogen protection, Intermediate 8 (3 g, 6.6 mmol), 2-chloro-4,6-diphenyl-1,3,5-triazine (2.1 g, 8 mmol), tris(dibenzylideneacetone)dipalladium (30 mg, 0.03 mmol), 3-(tert-butyl)-4-(2,6-dimethoxyphenyl)-2,3-dihydrobenzo[d][1,3]oxaphosphole (BI-DIME, 27 mg, 0.06 mmol), potassium phosphate (2.6 g, 13.2 mmol), and toluene (150 ml) were added to a three-necked flask and reacted at 110° C. for 10 hours. After the reaction was completed, the reaction solution was cooled to room temperature, concentrated to remove the solvents, and added with distilled water. The mixture was extracted with ethyl acetate. The organic phases were washed with water and concentrated to remove the solvents, and the crude product was purified by column chromatography (with PE/DCM=3/1) to obtain Compound 1 as a yellow solid (2.8 g, with a yield of 70%). The product was confirmed as the target product with a molecular weight of 637.2.

Under nitrogen protection, 2-chloro-4-(biphenyl-4-yl)-6-phenyl-1,3,5-triazine (3 g, 8.7 mmol), 2-fluorophenylboronic acid (1.23 g, 8.7 mmol), tetrakis(triphenylphosphine)palladium (200 mg, 0.17 mmol), potassium carbonate (2.42 g, 17.5 mmol), tetrahydrofuran (140 mL), and water (10 mL) were added to a three-necked flask and reacted at 85° C. overnight. After the reaction was completed, the reaction solution was cooled to room temperature, concentrated to remove the solvents, and added with distilled water. The mixture was extracted with ethyl acetate. The organic phases were washed with water, dried over anhydrous magnesium sulfate, concentrated to remove the solvents, and washed with ethanol to obtain white Intermediate 9 (3 g, with a yield of 85%).

Step 2: Synthesis of Compound 9

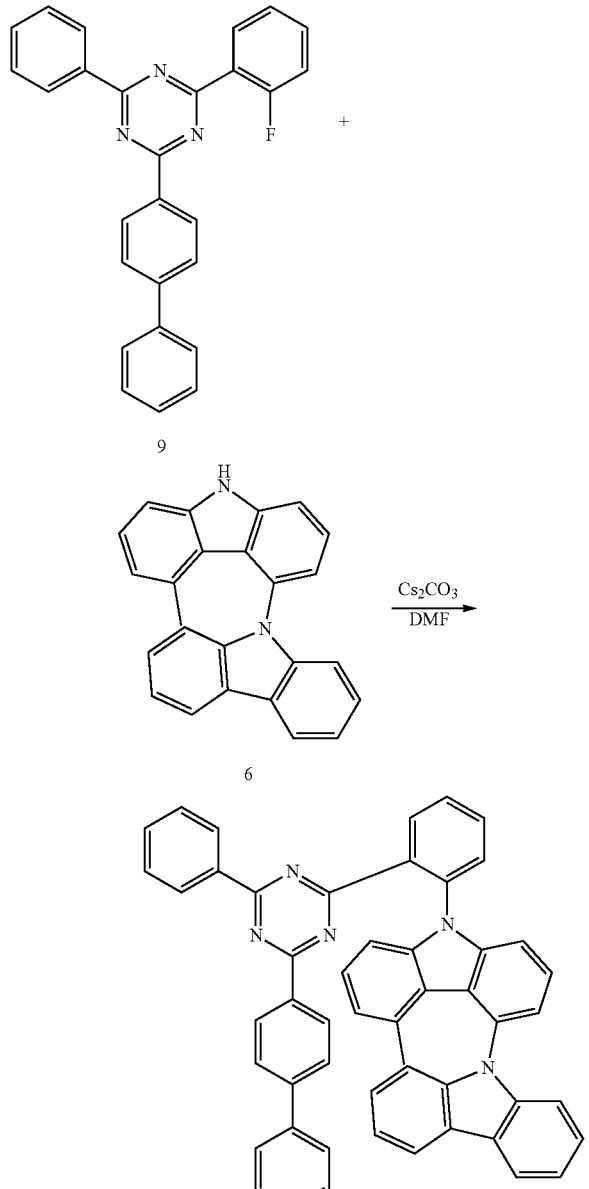

Compound 9

Under nitrogen protection, Intermediate 9 (610 mg, 1.5 mmol), Intermediate 6 (500 mg, 1.5 mmol), cesium carbonate (987 mg, 3 mmol), and DMF (15 mL) were added to a three-necked flask and reacted at 140° C. for 6 hours. After the reaction was completed, the reaction solution was cooled to room temperature and added with distilled water. The mixture was extracted with ethyl acetate. The organic phases were washed with water, dried over anhydrous magnesium sulfate, and concentrated to remove the solvents, and the crude product was purified by column chromatography (with PE/DCM=4/1) to obtain Compound 9 as a yellow solid (500 mg, with a yield of 46%). The product was confirmed as the target product with a molecular weight of 713.3.

Synthesis Example 3: Synthesis of Compound 373

Step 1: Synthesis of Intermediate 10

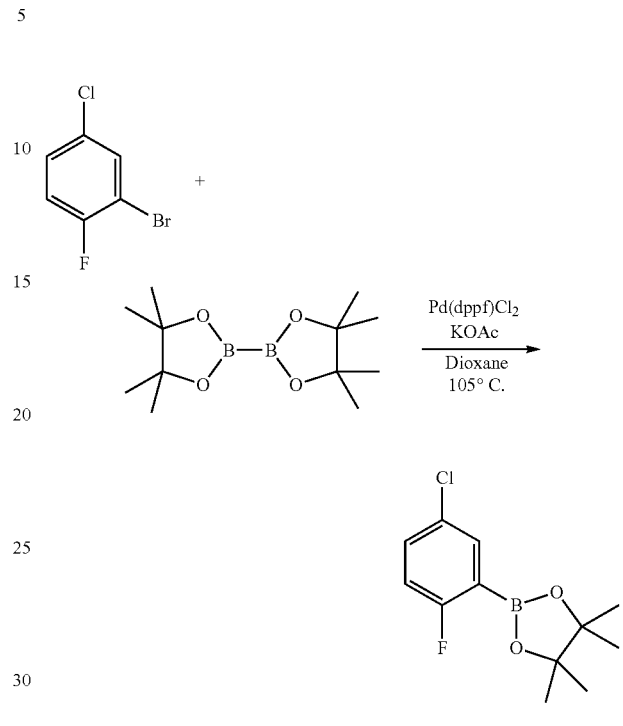

Under nitrogen protection, 2-fluoro-5-chlorobromobenzene (5.0 g, 23.9 mmol), bis(pinacolato)diboron (6.1 g, 23.9 mmol), [1,1'-bis(diphenylphosphino)ferrocene]palladium dichloride (Pd(dppf)Cl$_2$, 878 mg, 1.2 mmol), and potassium acetate (4.7 g, 47.8 mmol) were added to a dry 500 mL three-necked flask, and 100 mL of 1,4-dioxane was added. The mixture was reacted at 105° C. for 24 hours. After the reaction was completed, the reaction solution was cooled to room temperature, concentrated to remove the solvents, and added with distilled water. The mixture was extracted with ethyl acetate. The organic phases were washed with water, dried over anhydrous magnesium sulfate, concentrated to remove the solvents, and purified by column chromatography (PE/EA=10:1) to obtain Intermediate 10 as a yellow oil (5.4 g, with a yield of 88%).

Step 2: Synthesis of Intermediate 11

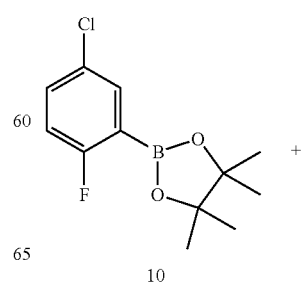

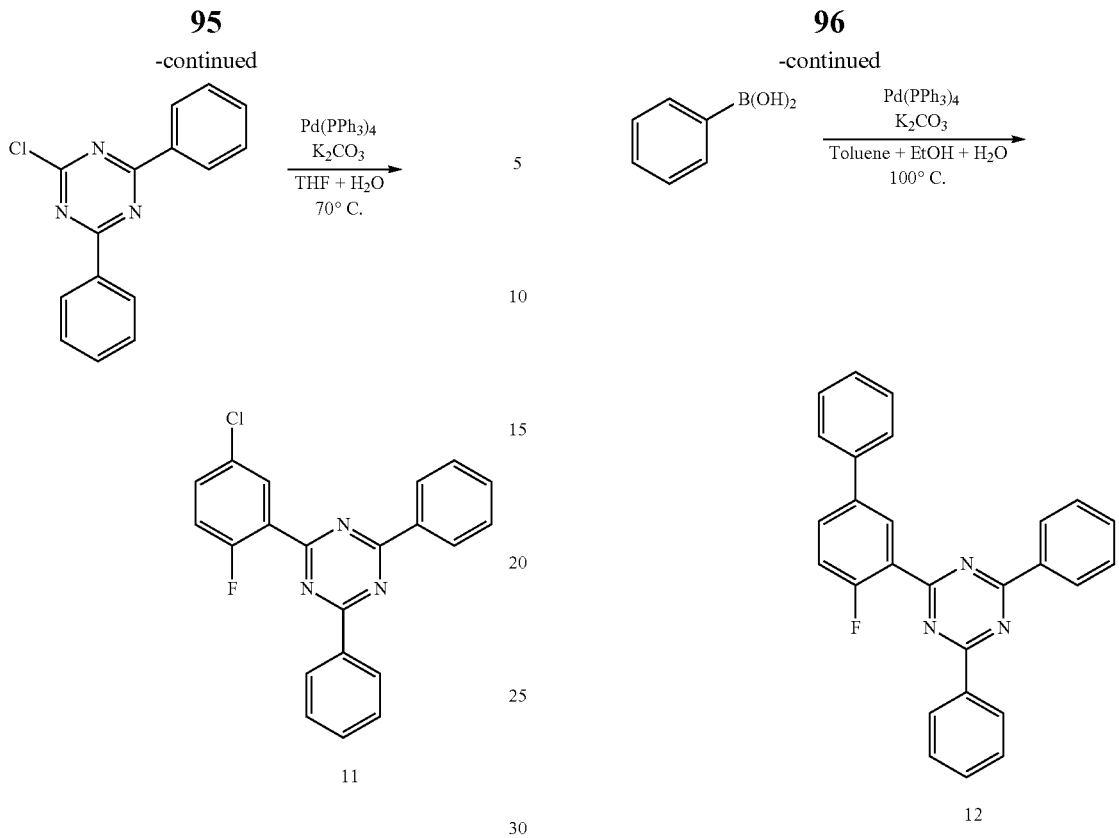

Under nitrogen protection, Intermediate 10 (5.4 g, 21.1 mmol), 2-chloro-4,6-diphenyl-1,3,5-triazine (6.8 g, 25.3 mmol), tetrakis(triphenylphosphine)palladium (1155 mg, 1.0 mmol), and potassium carbonate (5.8 g, 42.2 mmol) were added to a dry 500 mL three-necked flask, and tetrahydrofuran (70 mL) and water (30 mL) were added. The mixture was reacted at 70° C. for 18 hours. After the reaction was completed, the reaction solution was cooled to room temperature, concentrated to remove the solvents, and added with distilled water. The mixture was extracted with ethyl acetate. The organic phases were washed with water, dried over anhydrous magnesium sulfate, concentrated to remove the solvents, and purified by column chromatography (PE/EA=5:1) to obtain Intermediate 11 as a white solid (6.0 g, with a yield of 79%).

Step 3: Synthesis of Intermediate 12

Under nitrogen protection, Intermediate 11 (6.0 g, 16.6 mmol), phenylboronic acid (3.0 g, 24.9 mmol), tetrakis(triphenylphosphine)palladium (950 mg, 0.8 mmol), and potassium carbonate (4.6 g, 38.2 mmol) were added to a dry 500 mL three-necked flask, a mixed solvent of toluene (120 mL), water (30 mL), and ethanol (30 mL) were added, and the mixture was reacted at 100° C. for 18 hours. After the reaction was complete, the reaction solution was cooled to room temperature, concentrated to remove the solvents, and added with distilled water. The mixture was extracted with ethyl acetate. The organic phases were washed with water, dried over anhydrous magnesium sulfate, concentrated to remove the solvent, and purified by column chromatography (PE/EA=4:1) to obtain Intermediate 12 as a white solid (4.6 g, with a yield of 69%).

Step 4: Synthesis of Compound 373

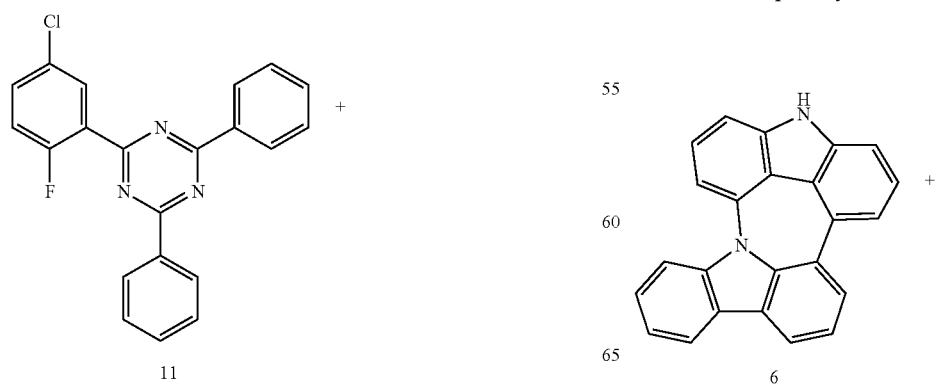

Synthesis Example 4: Synthesis of Compound 8

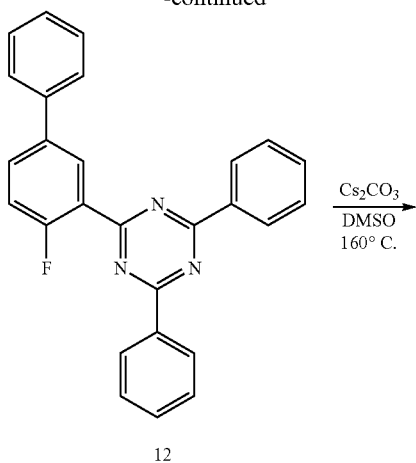

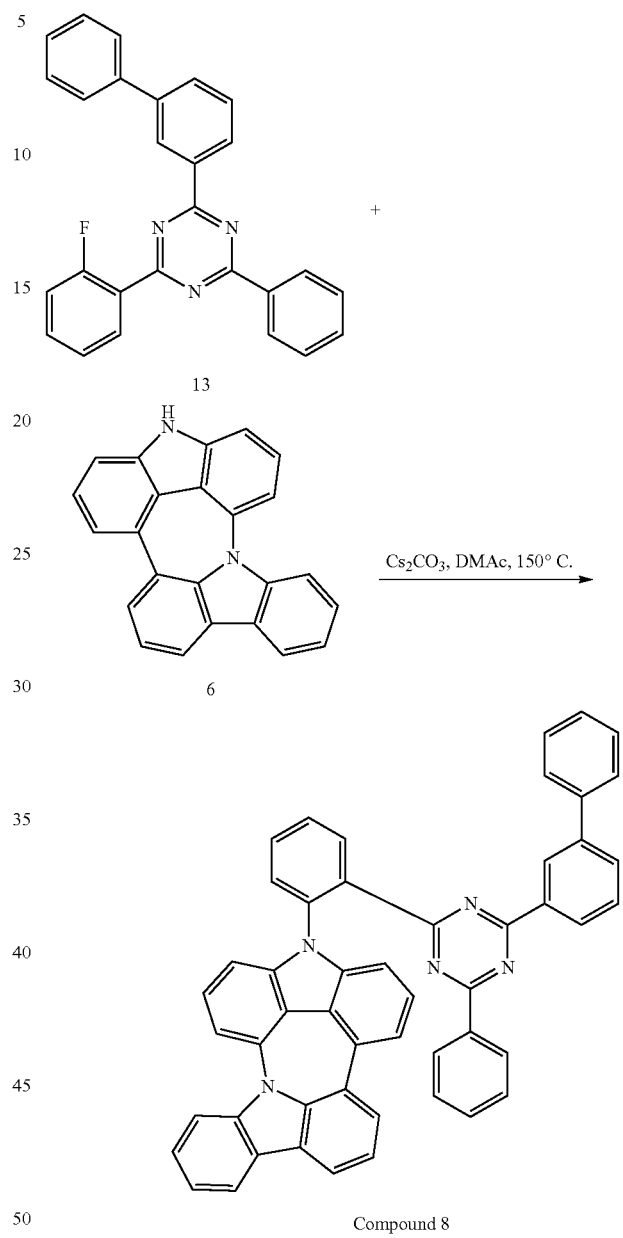

Under nitrogen protection, Intermediate 6 (2.0 g, 6.1 mmol), Intermediate 12 (2.9 g, 7.32 mmol), and cesium carbonate (4.0 g, 12.2 mmol) were added to a dry 250 mL three-necked flask, dimethyl sulfoxide (50 mL) was added, and the mixture was reacted at 160° C. for 24 hours. After the reaction was completed, the reaction solution was cooled to room temperature and added with distilled water. The mixture was extracted with ethyl acetate. The organic phases were washed with water and concentrated to remove the solvents, and the crude product was purified by column chromatography (with PE/DCM=4/1) to obtain Compound 373 as a yellow solid (3.0 g, with a yield of 69%). The product was confirmed as the target product with a molecular weight of 713.3.

Under nitrogen protection, Intermediate 13 (2.015 g, 5 mmol), Intermediate 6 (1.5 g, 4.54 mmol), cesium carbonate (2.96 g, 9.1 mmol), and DMAc (50 mL) were added to a 100 mL three-necked flask and reacted at 150° C. for 2 hours. After the reaction was completed, the reaction solution was cooled to room temperature and added with distilled water. The mixture was extracted with ethyl acetate. The organic phases were washed with water and concentrated to remove the solvents to obtain a crude product. The crude product was purified by column chromatography (eluent: PE/EA=25/1, v/v) to obtain Compound 8 as a yellow solid (2.7 g, with a yield of 83.3%). The product was confirmed as the target product with a molecular weight of 713.3.

Synthesis Example 5: Synthesis of Compound 15

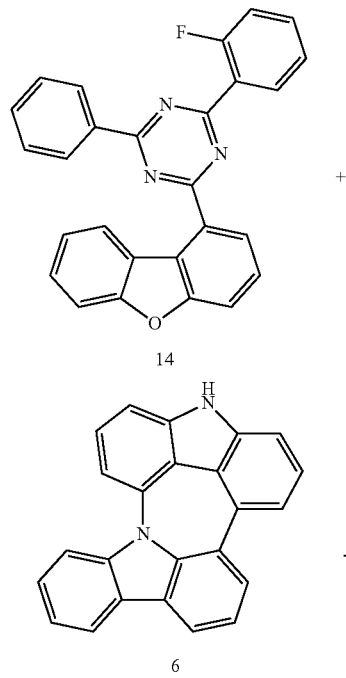

Synthesis Example 6: Synthesis of Compound 3

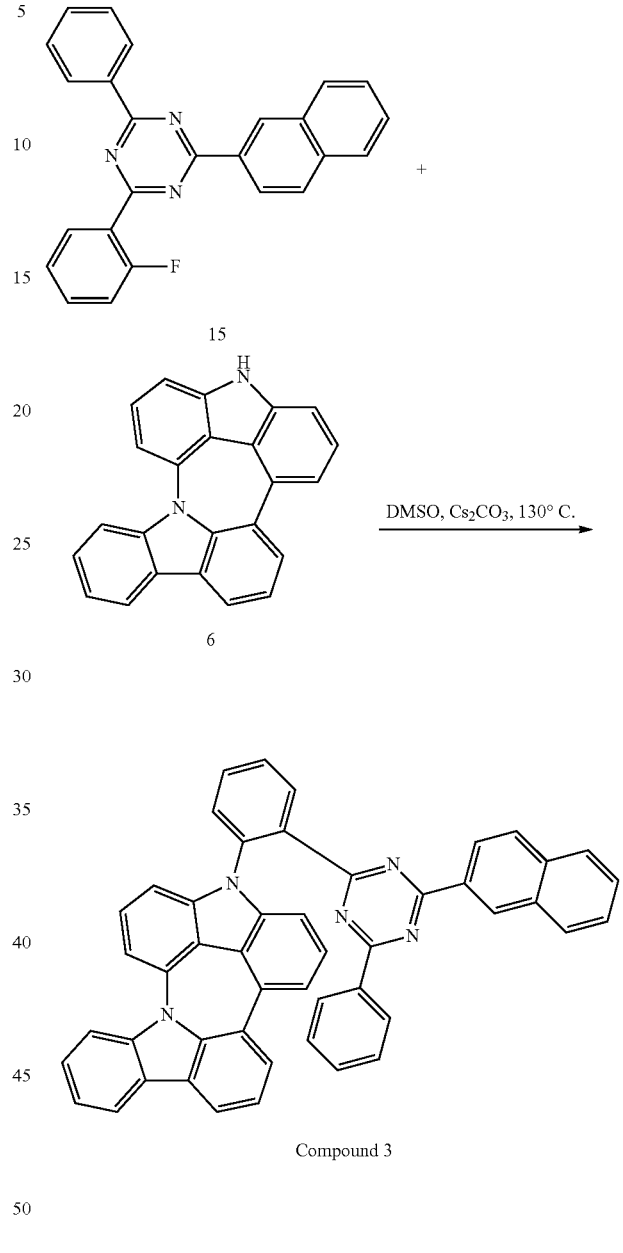

Under nitrogen protection, Intermediate 14 (1.6 g, 3.7 mmol), Intermediate 6 (1.1 g, 3.33 mmol), cesium carbonate (2.2 g, 6.66 mmol), and DMAc (20 mL) were added to a three-necked flask and reacted at 130° C. for 16 hours. After the reaction was completed, the reaction solution was cooled to room temperature and added with distilled water. The mixture was extracted with ethyl acetate. The organic phases were washed with water and concentrated to remove the solvents to obtain a crude product. The crude product was purified by column chromatography (eluent: PE/DCM=4/1, v/v) to obtain Compound 15 as a yellow solid (1 g, with a yield of 45%). The product was confirmed as the target product with a molecular weight of 727.2.

Under nitrogen protection, Intermediate 15 (3.4 g, 9.09 mmol), Intermediate 6 (2 g, 6.06 mmol), cesium carbonate (4.0 g, 12.31 mmol), and DMSO (30 mL) were added to a three-necked flask and reacted at 130° C. for 16 hours. After the reaction was completed, the reaction solution was cooled to room temperature and added with distilled water. The mixture was extracted with ethyl acetate. The organic phases were washed with water and concentrated to remove the solvents to obtain a crude product. The crude product was purified by column chromatography (eluent: PE/DCM=4/1, v/v) to obtain Compound 3 as a yellow solid (3.0 g, with a yield of 73%). The product was confirmed as the target product with a molecular weight of 687.2.

Synthesis Example 7: Synthesis of Compound 2

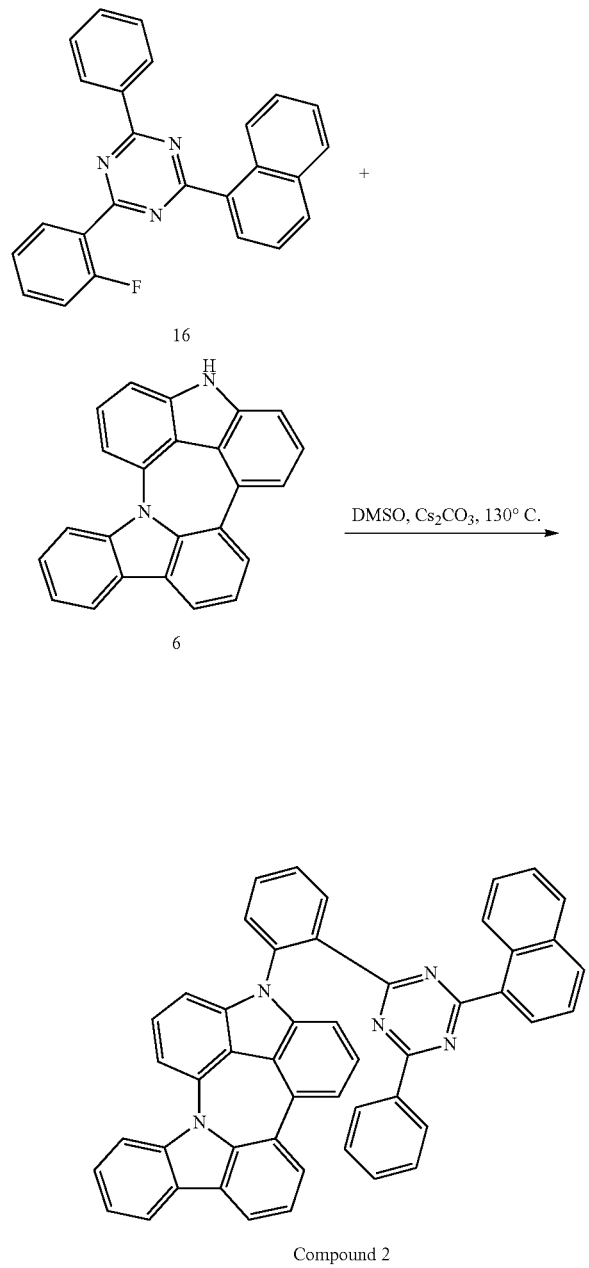

Compound 2

Under nitrogen protection, Intermediate 16 (3.4 g, 9.09 mmol), Intermediate 6 (2 g, 6.06 mmol), cesium carbonate (4.0 g, 12.31 mmol), and DMSO (30 mL) were added to a three-necked flask and reacted at 130° C. for 16 hours. After the reaction was completed, the reaction solution was cooled to room temperature and added with distilled water. The mixture was extracted with ethyl acetate. The organic phases were washed with water and concentrated to remove the solvents to obtain a crude product. The crude product was purified by column chromatography (eluent: PE/DCM=4/1, v/v) to obtain Compound 2 as a yellow solid (2.4 g, with a yield of 58%). The product was confirmed as the target product with a molecular weight of 687.2.

Synthesis Example 8: Synthesis of Compound 7

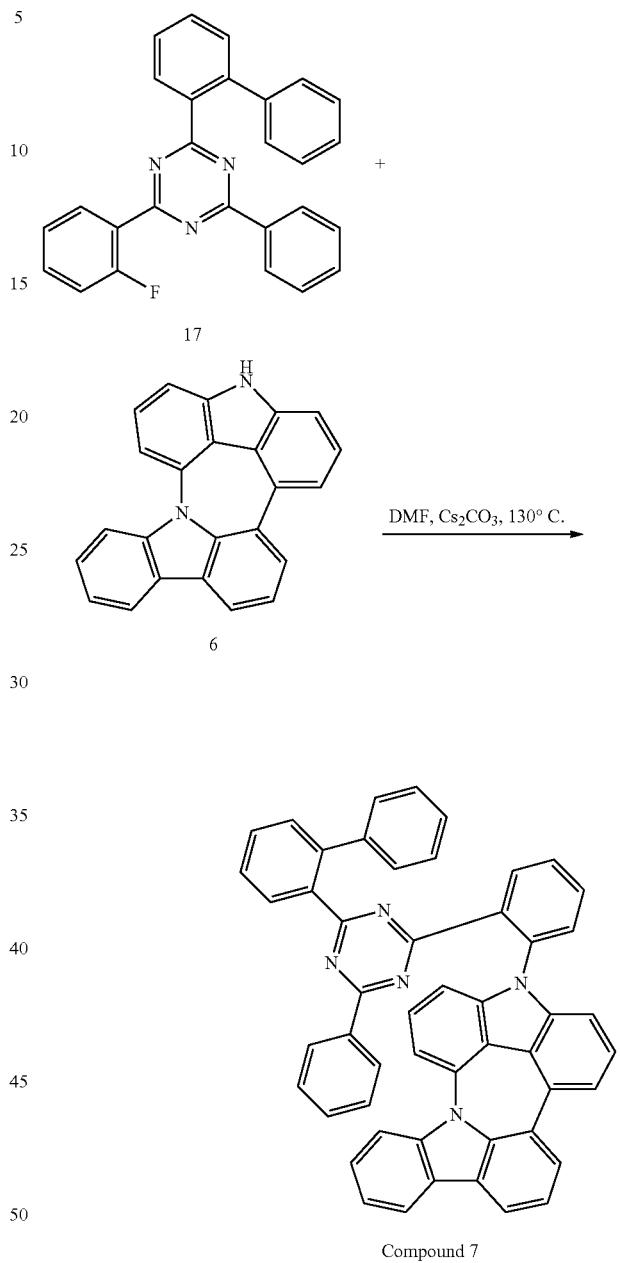

Compound 7

Under nitrogen protection, Intermediate 17 (2.015 g, 5 mmol), Intermediate 6 (1.5 g, 4.54 mmol), cesium carbonate (2.96 g, 9.1 mmol), and DMF (50 mL) were added to a 100 mL three-necked flask and reacted at 130° C. for 16 hours. After the reaction was completed, the reaction solution was cooled to room temperature and added with distilled water. The mixture was extracted with ethyl acetate. The organic phases were washed with water and concentrated to remove the solvents to obtain a crude product. The crude product was purified by column chromatography (eluent: PE/DCM=4/1, v/v) to obtain Compound 7 as a yellow solid (2 g, with a yield of 61.7%). The product was confirmed as the target product with a molecular weight of 713.3.

Synthesis Example 9: Synthesis of Compound 23

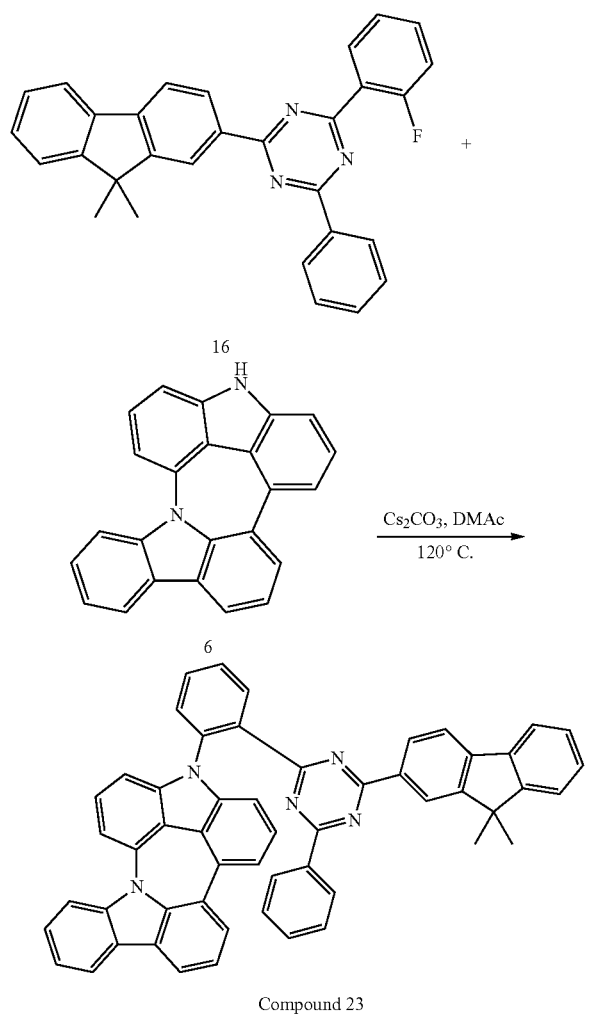

Compound 23

Under nitrogen protection, Intermediate 6 (2 g, 6.06 mmol), Intermediate 18 (2.9 g, 6.66 mmol), cesium carbonate (3.9 g, 12.12 mmol), and DMAc (50 mL) were added to a three-necked flask and reacted at 120° C. for 16 hours. After the reaction was completed, the reaction solution was cooled to room temperature, concentrated to remove the solvents, and added with distilled water. The mixture was extracted with ethyl acetate. The organic phases were washed with water and concentrated to remove the solvents to obtain a crude product. The crude product was purified by column chromatography (with PE/DCM=3/1, v/v) to obtain Compound 23 as a yellow solid (3 g, with a yield of 66%). The product was confirmed as the target product with a molecular weight of 753.3.

Those skilled in the art will appreciate that the above preparation methods are merely illustrative. Those skilled in the art can obtain other compound structures of the present disclosure through the modifications of the above-mentioned preparation methods.

Device Example 1

First, a glass substrate having an Indium Tin Oxide (ITO) anode having a thickness of 120 nm was cleaned and then treated with UV ozone and oxygen plasma. After the treatment, the substrate was dried in a nitrogen-filled glovebox to remove moisture and then mounted on a substrate holder and placed in a vacuum chamber. Organic layers specified below were sequentially deposited through vacuum thermal evaporation on the ITO anode at a rate of 0.01 to 5 Angstroms per second (Å/s) at a vacuum degree of about $10^{-8}$ torr. Compound HI was used as a hole injection layer (HIL) with a thickness of 100 Angstroms (Å). Compound HT was used as a hole transporting layer (HTL) with a thickness of 400 Å. Compound EB was used as an electron blocking layer (EBL) with a thickness of 50 Å. Then, Compound 1 of the present disclosure as a host and Compound RD as a dopant were co-deposited as an emissive layer (EML) with a thickness of 400 Å. Compound HB was used as a hole blocking layer (HBL) with a thickness of 50 Å. On the hole blocking layer, Compound ET and 8-hydroxyquinolinolato-lithium (Liq) were co-deposited as an electron transporting layer (ETL) with a thickness of 350 Å. Finally, 8-hydroxyquinolinolato-lithium (Liq) with a thickness of 10 Å was deposited as an electron injection layer (EIL), and aluminum was deposited as a cathode with a thickness of 1200 Å. The device was transferred back to the glovebox and encapsulated with a glass lid to complete the device.

Device Example 2

The implementation mode in Device Example 2 was the same as that in Device Example 1, except that Compound 9 of the present disclosure replaced Compound 1 of the present disclosure and was used as the host in the emissive layer (EML).

Device Example 3

The implementation mode in Device Example 3 was the same as that in Device Example 1, except that Compound 15 of the present disclosure replaced Compound 1 of the present disclosure and was used as the host in the emissive layer (EML).

Device Example 4

The implementation mode in Device Example 4 was the same as that in Device Example 1, except that Compound 3 of the present disclosure replaced Compound 1 of the present disclosure and was used as the host in the emissive layer (EML).

Device Example 5

The implementation mode in Device Example 5 was the same as that in Device Example 1, except that Compound 2 of the present disclosure replaced Compound 1 of the present disclosure and was used as the host in the emissive layer (EML).

Device Example 6

The implementation mode in Device Example 6 was the same as that in Device Example 1, except that Compound 8 of the present disclosure replaced Compound 1 of the present disclosure and was used as the host in the emissive layer (EML).

Device Example 7

The implementation mode in Device Example 7 was the same as that in Device Example 1, except that Compound 7 of the present disclosure replaced Compound 1 of the present disclosure and was used as the host in the emissive layer (EML).

Device Comparative Example 1

The implementation mode in Device Comparative Example 1 was the same as that in Device Example 1, except that Compound A replaced Compound 1 of the present disclosure and was used as the host in the emissive layer (EDL).

Device Comparative Example 2

The implementation mode in Device Comparative Example 2 was the same as that in Device Example 1, except that Compound B replaced Compound 1 of the present disclosure and was used as the host in the emissive layer (EML).

Detailed structures and thicknesses of layers of the devices are shown in the following table. The layers using more than one material are obtained by doping different compounds at weight ratios as recorded in the following table.

The structures of the materials used in the device are as follows:

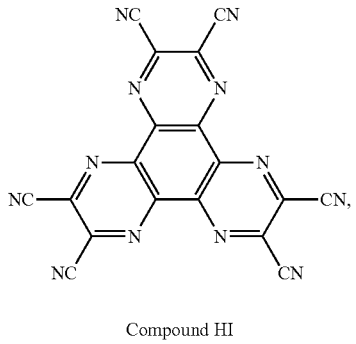

Compound HI

TABLE 1

Device structures in Device Examples and Comparative Examples

| Device ID | HIL | HTL | EBL | EML (400 Å) | | HBL | ETL |
| --- | --- | --- | --- | --- | --- | --- | --- |
| | | | | Host | Dopant | | |
| Example 1 | Compound HI (100 Å) | Compound HT (400 Å) | Compound EB (50 Å) | Compound 1 (98%) | Compound RD (2%) | Compound HB (50 Å) | Compound ET:Liq (40:60) (350 Å) |
| Example 2 | Compound HI (100 Å) | Compound HT (400 Å) | Compound EB (50 Å) | Compound 9 (98%) | Compound RD (2%) | Compound HB (50 Å) | Compound ET:Liq (40:60) (350 Å) |
| Example 3 | Compound HI (100 Å) | Compound HT (400 Å) | Compound EB (50 Å) | Compound 15 (98%) | Compound RD (2%) | Compound HB (50 Å) | Compound ET:Liq (40:60) (350 Å) |
| Example 4 | Compound HI (100 Å) | Compound HT (400 Å) | Compound EB (50 Å) | Compound 3 (98%) | Compound RD (2%) | Compound HB (50 Å) | Compound ET:Liq (40:60) (350 Å) |
| Example 5 | Compound HI (100 Å) | Compound HT (400 Å) | Compound EB (50 Å) | Compound 2 (98%) | Compound RD (2%) | Compound HB (50 Å) | Compound ET:Liq (40:60) (350 Å) |
| Example 6 | Compound HI (100 Å) | Compound HT (400 Å) | Compound EB (50 Å) | Compound 8 (98%) | Compound RD (2%) | Compound HB (50 Å) | Compound ET:Liq (40:60) (350 Å) |
| Example 7 | Compound HI (100 Å) | Compound HT (400 Å) | Compound EB (50 Å) | Compound 7 (98%) | Compound RD (2%) | Compound HB (50 Å) | Compound ET:Liq (40:60) (350 Å) |
| Comparative Example 1 | Compound HI (100 Å) | Compound HT (400 Å) | Compound EB (50 Å) | Compound A (98%) | Compound RD (2%) | Compound HB (50 Å) | Compound ET:Liq (40:60) (350 Å) |
| Comparative Example 2 | Compound HI (100 Å) | Compound HT (400 Å) | Compound EB (50 Å) | Compound B (98%) | Compound RD (2%) | Compound HB (50 Å) | Compound ET:Liq (40:60) (350 Å) |

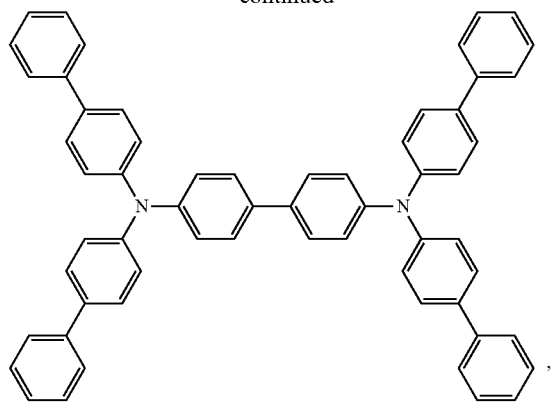
Compound HT
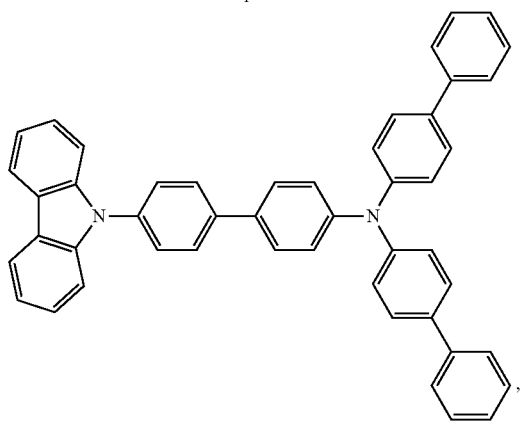
Compound EB
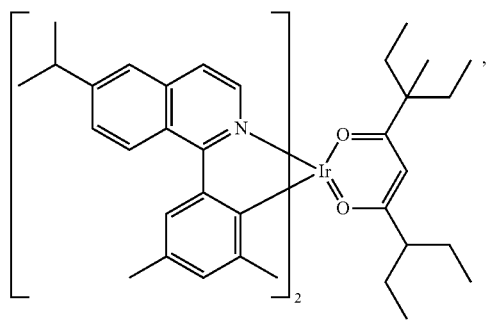
Compound RD
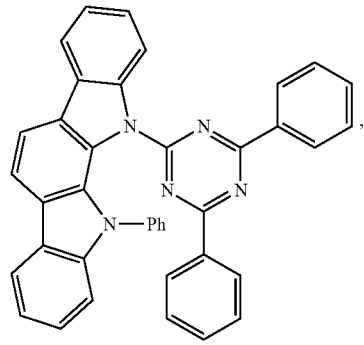
Compound HB
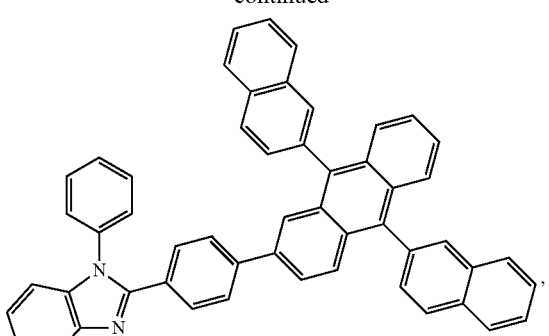
Compound ET
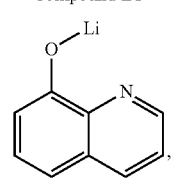
Liq
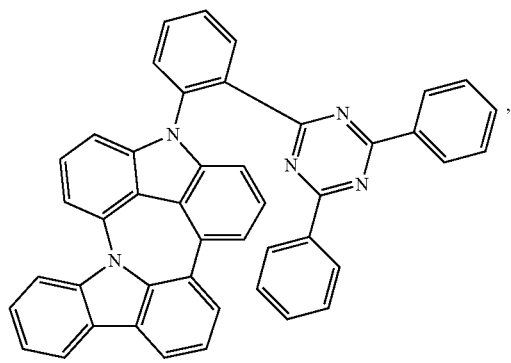
Compound 1
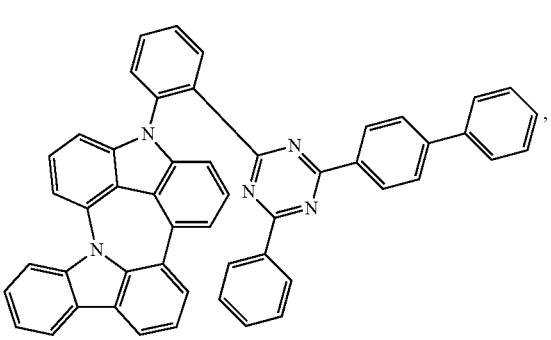
Compound 9

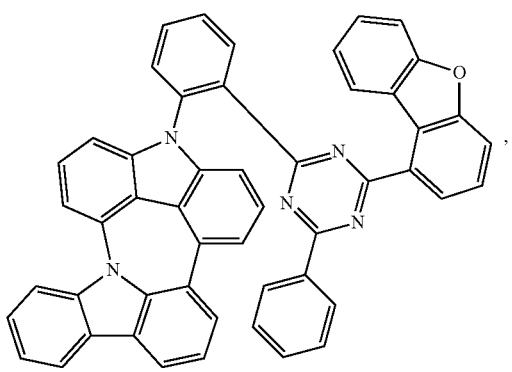
Compound 15
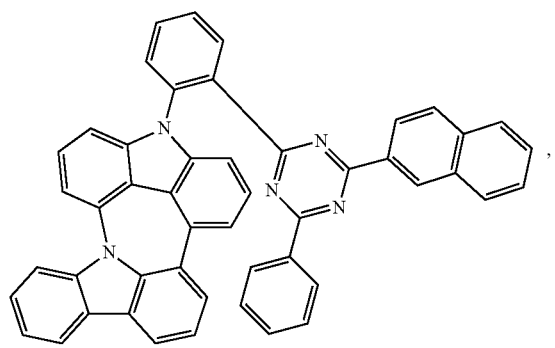
Compound 3
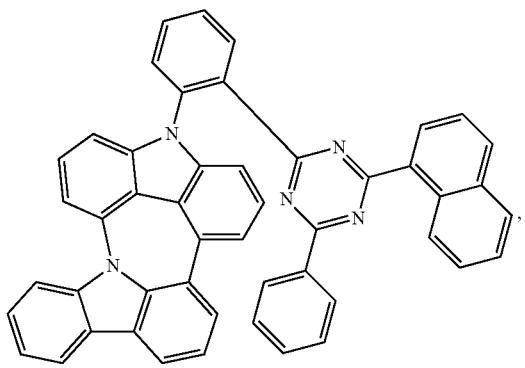
Compound 2
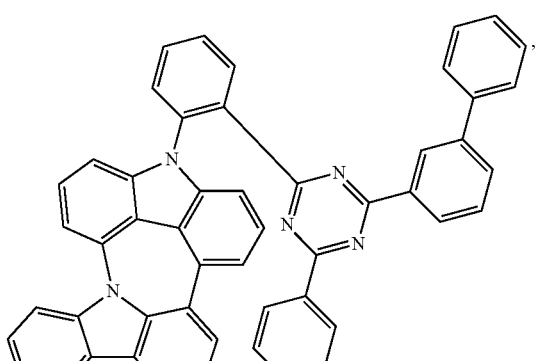
Compound 8
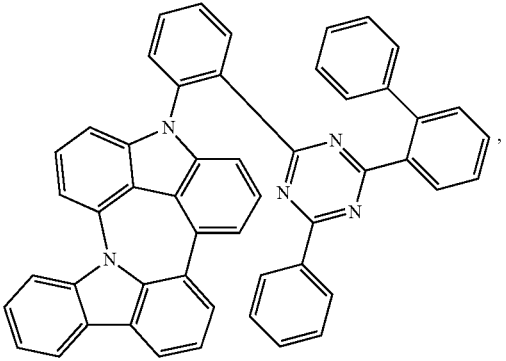
Compound 7
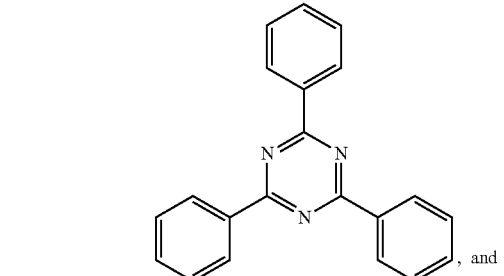
, and
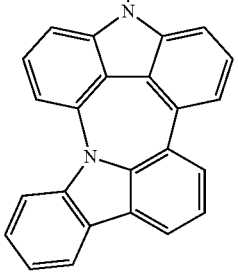
Compound A
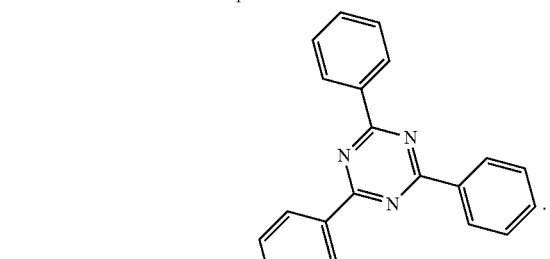
Compound B
Table 2 lists the temperatures (evaporation temperatures) required for the evaporation of Compound 1, Compound 9, Compound 15, Compound 3, Compound 2, Compound 8, Compound 7, Compound A, and Compound B at a rate of 1.96/s at a vacuum degree of about $10^{-8}$ torr.

TABLE 2

| | Evaporation temperature | | | |
|---|---|---|---|---|
| | Compound 1 | Compound 9 | Compound A | Compound B |
| Evaporation temperature (° C.) | 265 | 295 | 303 | 338 |
| | Compound 15 | Compound 3 | Compound 2 | Compound 8 |
| Evaporation temperature (° C.) | 282 | 281 | 281 | 279 |
| | Compound 7 | | | |
| Evaporation temperature (° C.) | 265 | | | |

As shown in Table 2, Compound 1 disclosed by the present disclosure unexpectedly has a much lower evaporation temperature than both Compound A and Compound B just due to the change in the position of substitution of the triazine structure unit, which indicates that the ortho-substituted phenylene connecting structure in the molecular structure of Compound 1 brings an unexpected effect of greatly reducing the evaporation temperature of Compound 1 and thus Compound 1 disclosed by the present disclosure has better thermal stability and is easier to process in the device manufacturing process, and energy consumption can be reduced more effectively. Compound 9 (although Compound 9 disclosed by the present disclosure has one more phenyl group in the triazine fragment), Compound 15, Compound 3, Compound 2, Compound 8, and Compound 7 all have higher molecular weights than Compound A and Compound B, but their evaporation temperatures are still lower than those of Compound A and Compound B.

Table 3 lists current efficiency (CE), maximum wavelength ($\lambda_{max}$), and external quantum efficiency (EQE) measured under the condition of 15 mA/cm². In order to better illustrate the comparison of data, the CE and EQE data of the device of Comparative Example 1 were set to 100%, respectively, and the CE and EQE data of the devices in Example 1, Examples 2-7, and Comparative Example 2 were all converted with respect to the corresponding data of the device of Comparative Example 1. The relevant data and conversion results are shown in Table 3.

TABLE 3

| | Device data | | |
|---|---|---|---|
| | At 15 mA/cm² | | |
| Device ID | $\lambda_{max}$ (nm) | CE | EQE |
| Example 1 | 626 | 105% | 107% |
| Example 2 | 626 | 105% | 107% |
| Example 3 | 626 | 111% | 109% |
| Example 4 | 626 | 110% | 107% |
| Example 5 | 626 | 114% | 110% |
| Example 6 | 626 | 107% | 106% |
| Example 7 | 625 | 111% | 107% |
| Comparative Example 1 | 626 | 100% | 100% |
| Comparative Example 2 | 625 | 100% | 99% |

DISCUSSION

As shown in Table 3, the maximum wavelengths of the devices of Comparative Examples and Examples remained substantially the same. EQEs of the devices of Examples 1 and 2, measured at a current density of 15 mA/cm², were increased by 7% and 8%, respectively, relative to EQEs of the devices of Comparative example 1 and Comparative example 2. CEs of the devices of Examples 1 and 2 were increased by 5% relative to CEs of the devices of Comparative Example 1 and Comparative Example 2. EQEs of the devices of Examples 3 to 7, measured at a current density of 15 mA/cm², were significantly increased by 7% to 10% relative to EQEs of the devices of Comparative Example 1 and Comparative Example 2. CEs of the devices of Examples 3 to 7 were also increased by 7% to 14% relative to CEs of the devices of Comparative Example 1 and Comparative Example 2, and the increase was more significant. The data show that the devices of Examples have more excellent luminescence efficiency than the devices of Comparative Examples. That is, compared with Compound A and Compound B in which the hole transporting unit is bonded to meta- and para-positions with triazine respectively, for the compounds according to the present disclosure formed by connecting the hole transporting unit which is based on an indole- and pyrrole-fused azamacrocyclic structure to the electron transporting unit which is based on triazine or a similar structure thereof at a specific position, since the electron transporting unit and the hole transporting unit are connected through specific position structures, the planarity of the molecules of the compounds according to the present disclosure is different from that of Compound A or Compound B, and unexpectedly, such a difference brings excellent device effect, enabling the device to obtain higher current efficiency and external quantum efficiency and thus have significant improvement in device performance. The above proves the unique advantages of the compound of the present disclosure.

It should be understood that various embodiments described herein are examples and not intended to limit the scope of the present disclosure. Therefore, it is obvious to those skilled in the art that the present disclosure as claimed may include variations of specific embodiments and preferred embodiments described herein. Many of the materials and structures described herein may be replaced with other materials and structures without departing from the spirit of the present disclosure. It should be understood that various theories as to why the present disclosure works are not intended to be limitative.

The invention claimed is:

1. A compound, having a structure of H-L-E, wherein H has a structure represented by Formula 1-a;

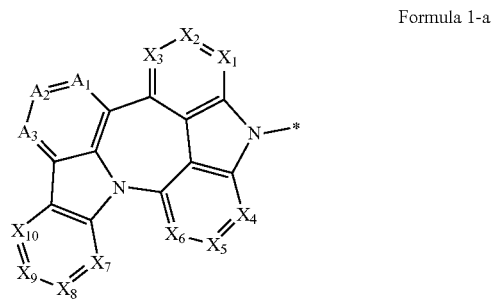

Formula 1-a in Formula 1-a, $A_1$, $A_2$, and $A_3$ are, at each occurrence identically or differently, selected from CR, and $X_1$ to $X_{10}$ are, at each occurrence identically or differently, selected from $CR_x$;

E has a structure represented by Formula 2:

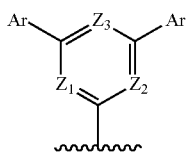

Formula 2 in Formula 2, Ar is, at each occurrence identically or differently, selected from substituted or unsubstituted aryl having 6 to 30 carbon atoms or substituted or unsubstituted heteroaryl having 3 to 30 carbon atoms;
$Z_1$ to $Z_3$ are each independently selected from N or $CR_z$, and at least one of $Z_1$ to $Z_3$ is N;
L has a structure represented by Formula 3:

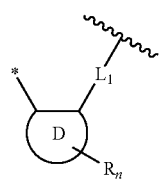

Formula 3 in Formula 3, the ring D is, at each occurrence identically or differently, selected from a carbocyclic ring having 5 to 18 carbon atoms or a heteroaromatic ring having 3 to 18 carbon atoms, wherein the heteroaromatic ring has 1 hetero-atom;
$R_n$ represents, at each occurrence identically or differently, mono-substitution, multiple substitutions, or non-substitution;
$L_1$ is selected from a single bond, substituted or unsubstituted arylene having 6 to 30 carbon atoms, substituted or unsubstituted heteroarylene having 3 to 30 carbon atoms, or combinations thereof; and when $L_1$ is selected from substituted arylene having 6 to 30 carbon atoms or substituted heteroarylene having 3 to 30 carbon atoms, $L_1$ has a substituent $R_m$; and $R_m$ represents, at each occurrence identically or differently, mono-substitution or multiple substitutions;
R, $R_x$, $R_z$, $R_n$, and $R_m$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;
adjacent substituents R, $R_x$ can be optionally joined to form a ring;
adjacent substituents $R_n$, $R_m$ can be optionally joined to form a ring.

2. The compound according to claim 1, wherein the H has a structure represented by Formula 1-a:

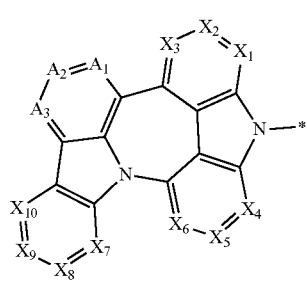

Formula 1-a $A_1$ to $A_3$ are, at each occurrence identically or differently, selected from CR, and $X_1$ to $X_{10}$ are, at each occurrence identically or differently, selected from $CR_x$;
R and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

3. The compound according to claim 1, wherein R and $R_x$ are, at each occurrence identically or differently, selected from the group consisting of: hydrogen, deuterium, halogen, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a hydroxyl group, a sulfanyl group, and combinations thereof;

adjacent substituents R, $R_x$ can be optionally joined to form a ring.

4. The compound of claim 1, wherein at least one of R and $R_x$ is selected from deuterium, substituted or unsubstituted aryl having 6 to 30 carbon atoms, or substituted or unsubstituted heteroaryl having 3 to 30 carbon atoms.

5. The compound according to claim 1, wherein at least one of groups of adjacent substituents: adjacent substituents R in $A_1$ to $A_3$, adjacent substituents $R_x$ in $X_1$ to $X_3$, adjacent substituents $R_x$ in $X_4$ to $X_6$, and adjacent substituents $R_x$ in $X_7$ to $X_{10}$ is joined to form a ring.

6. The compound according to claim 1, wherein the H is selected from the group consisting of the following structures:

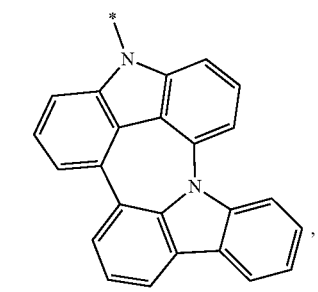
H-1

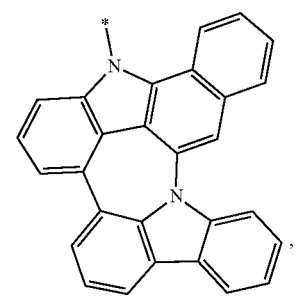
H-2

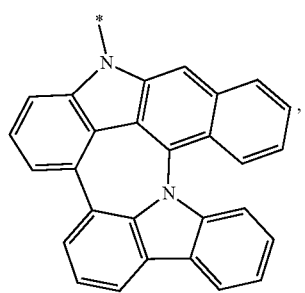
H-3

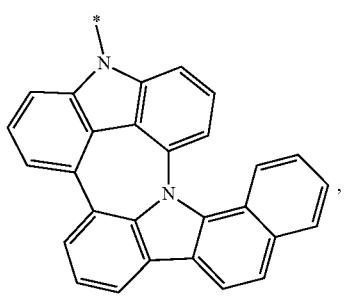
H-4

-continued

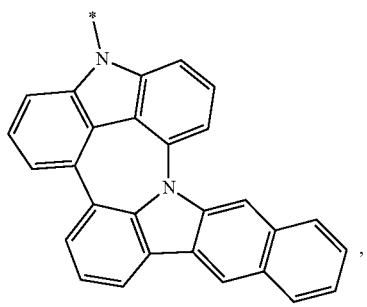
H-5

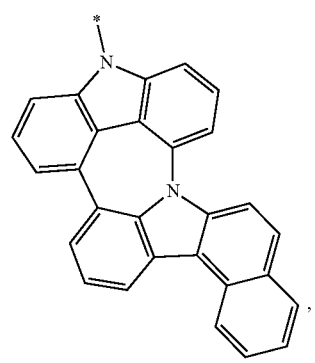
H-6

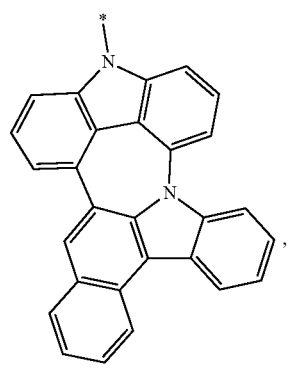
H-7

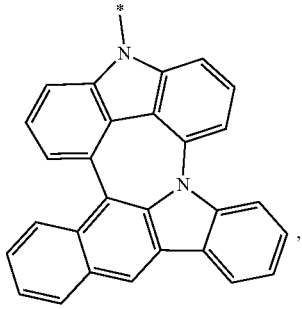
H-8

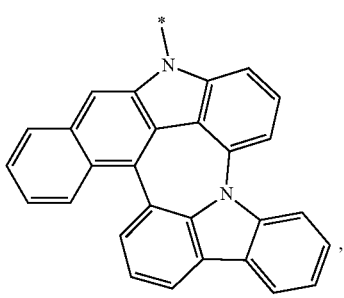
H-9

H-10
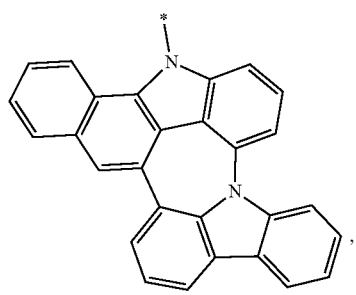
H-11
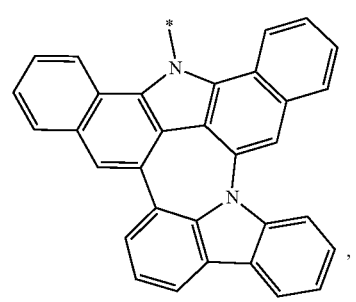
H-12
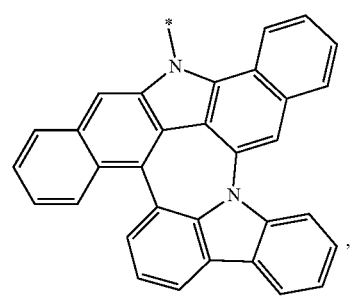
H-13
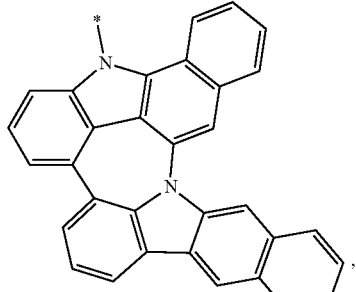
H-14
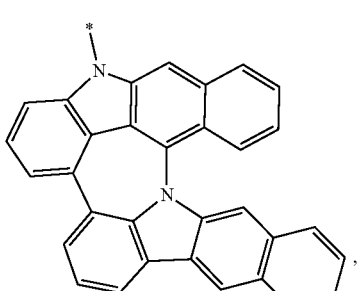
H-15
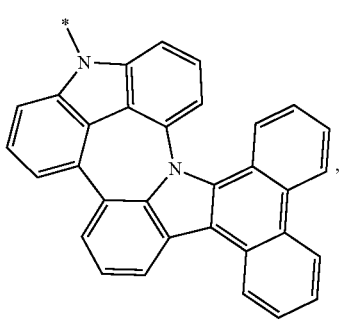
H-16
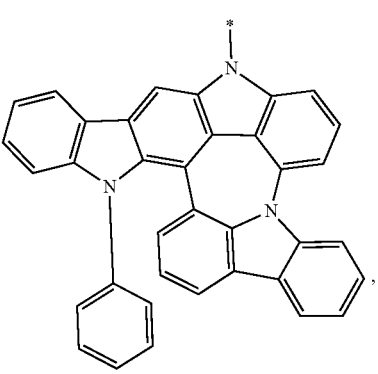
H-17
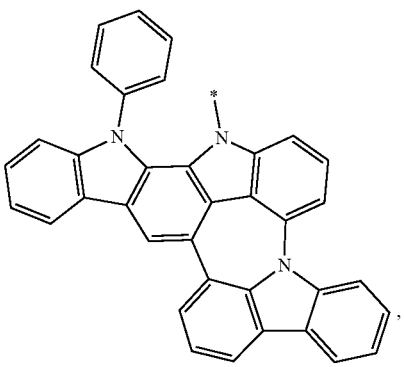
H-18
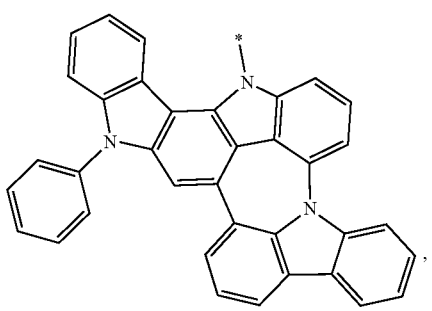

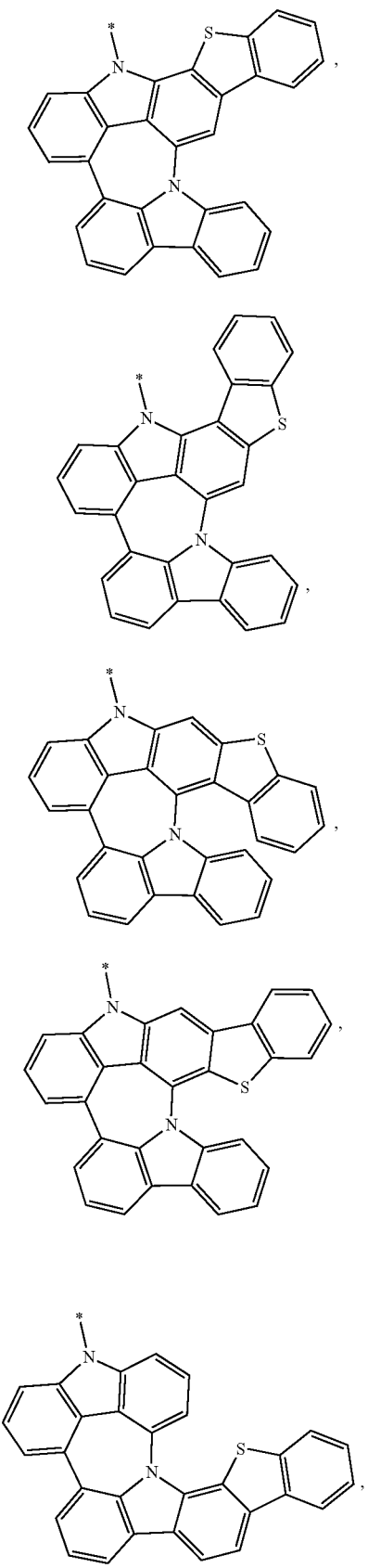
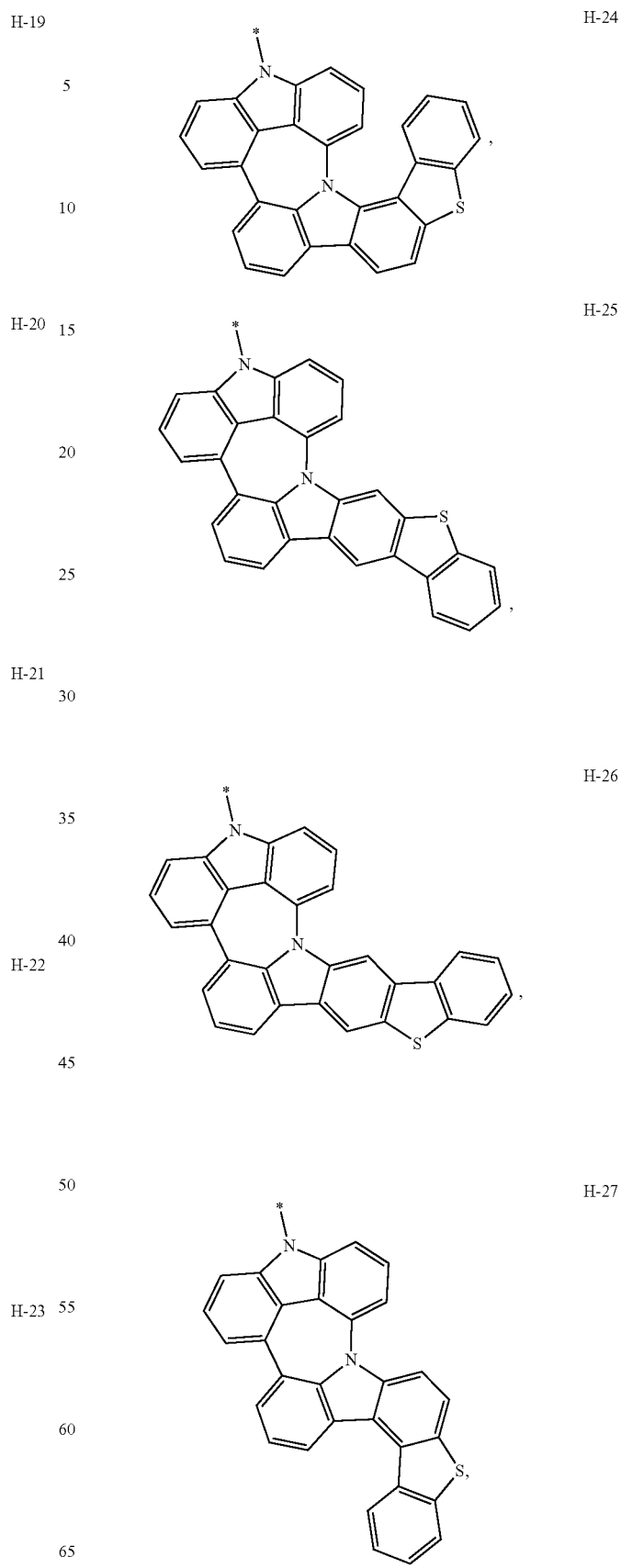

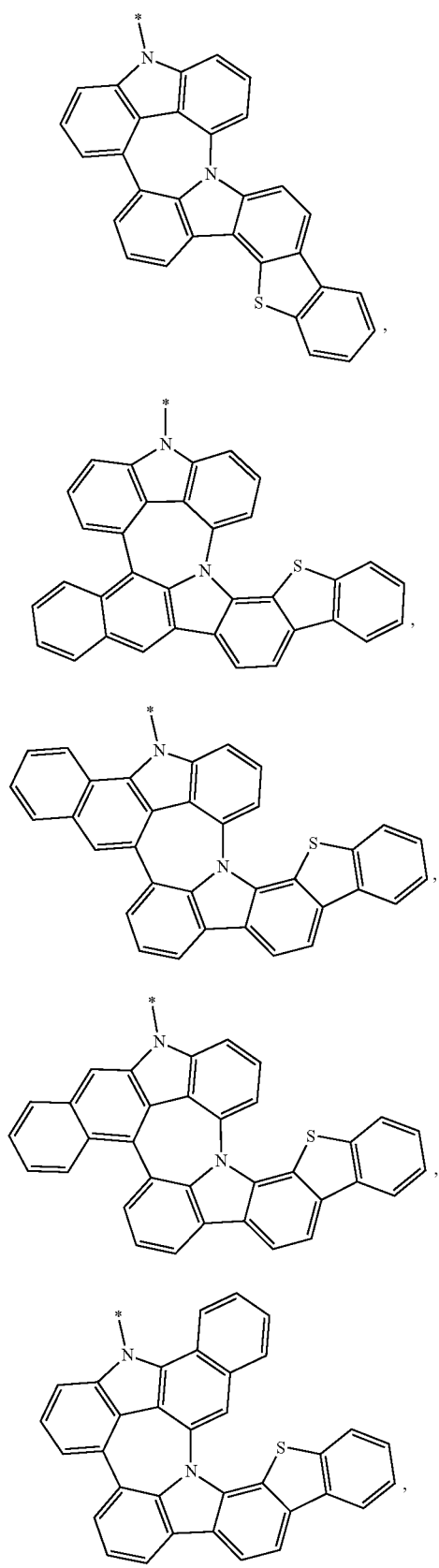
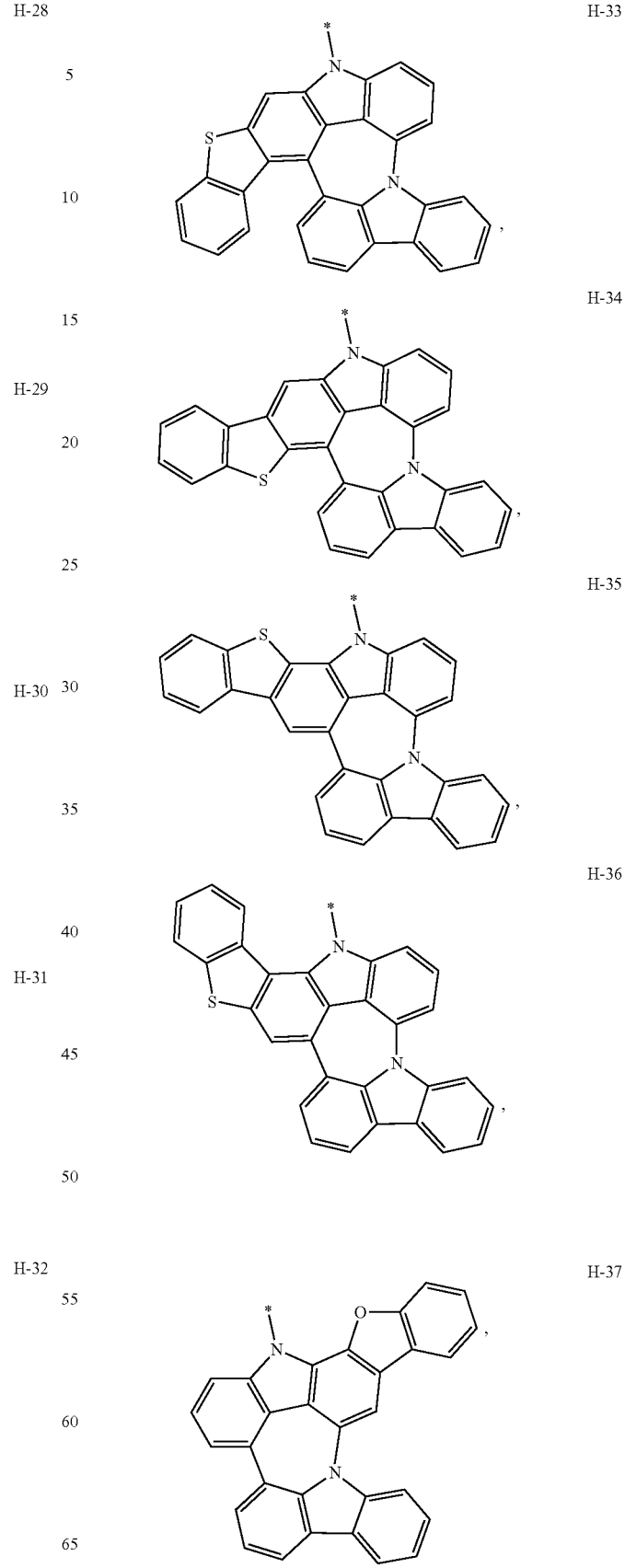

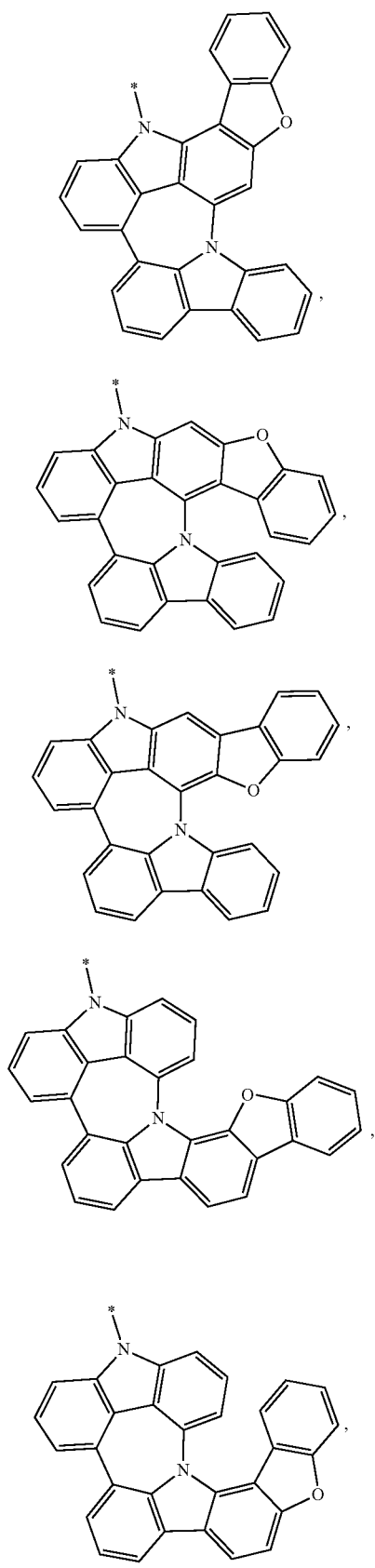
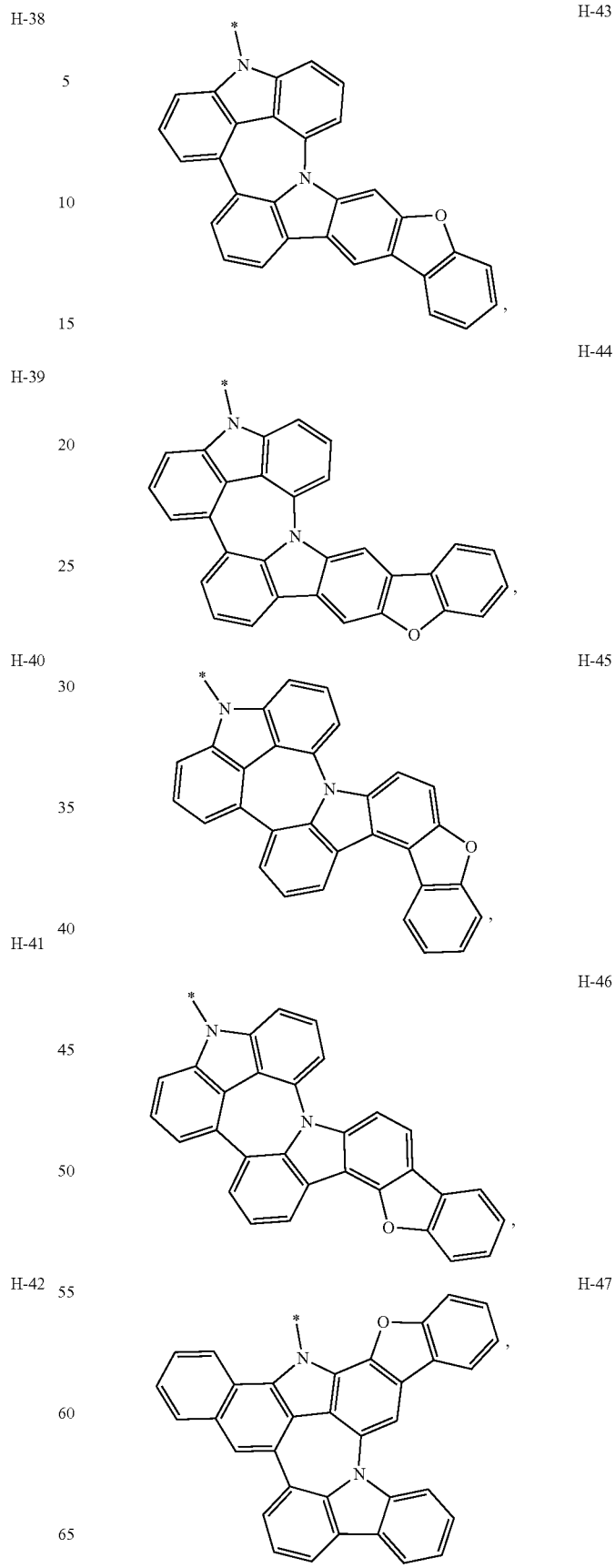

H-48
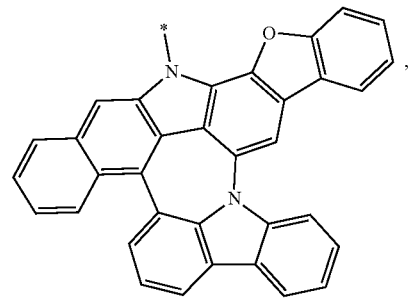
H-49
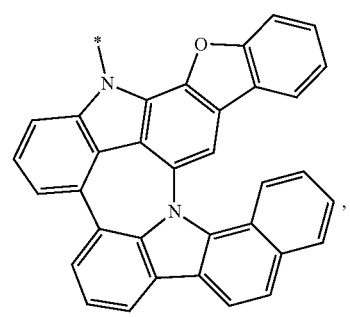
H-50
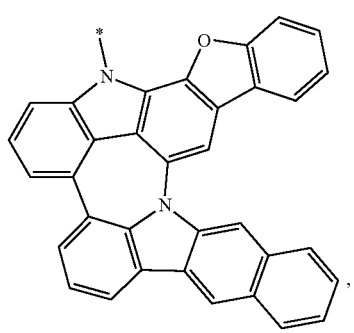
H-51
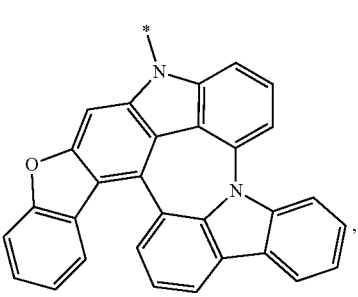
H-52
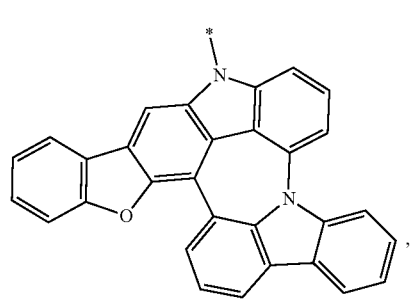
H-53
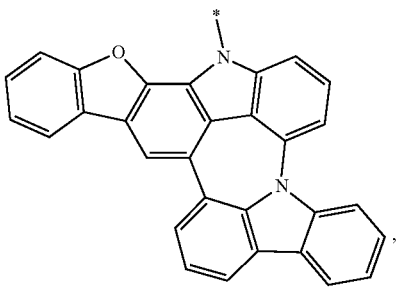
H-54
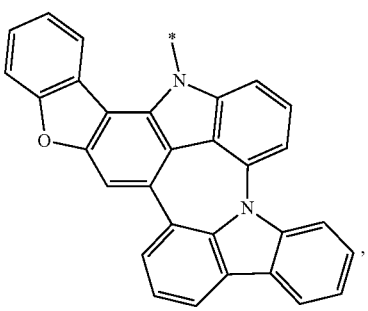
H-55
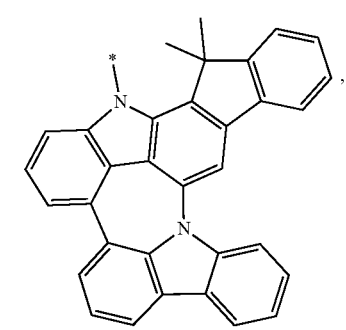
H-56
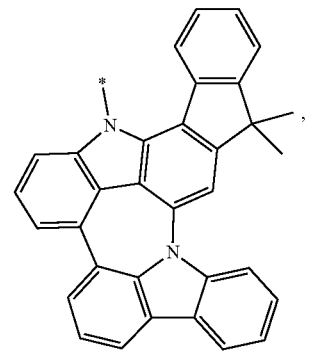
H-57
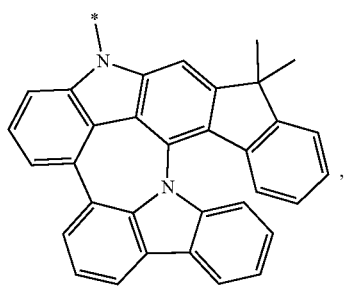

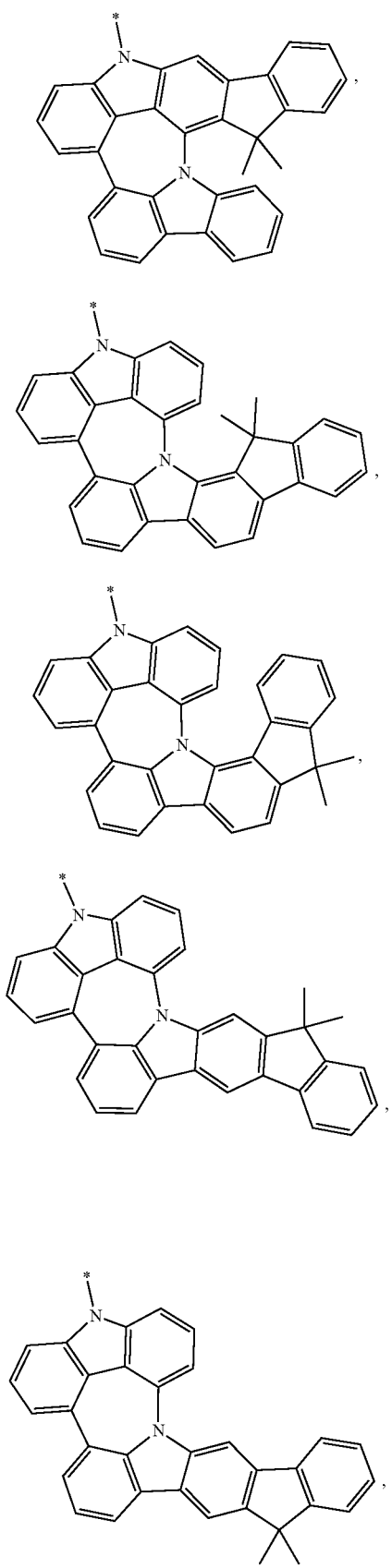
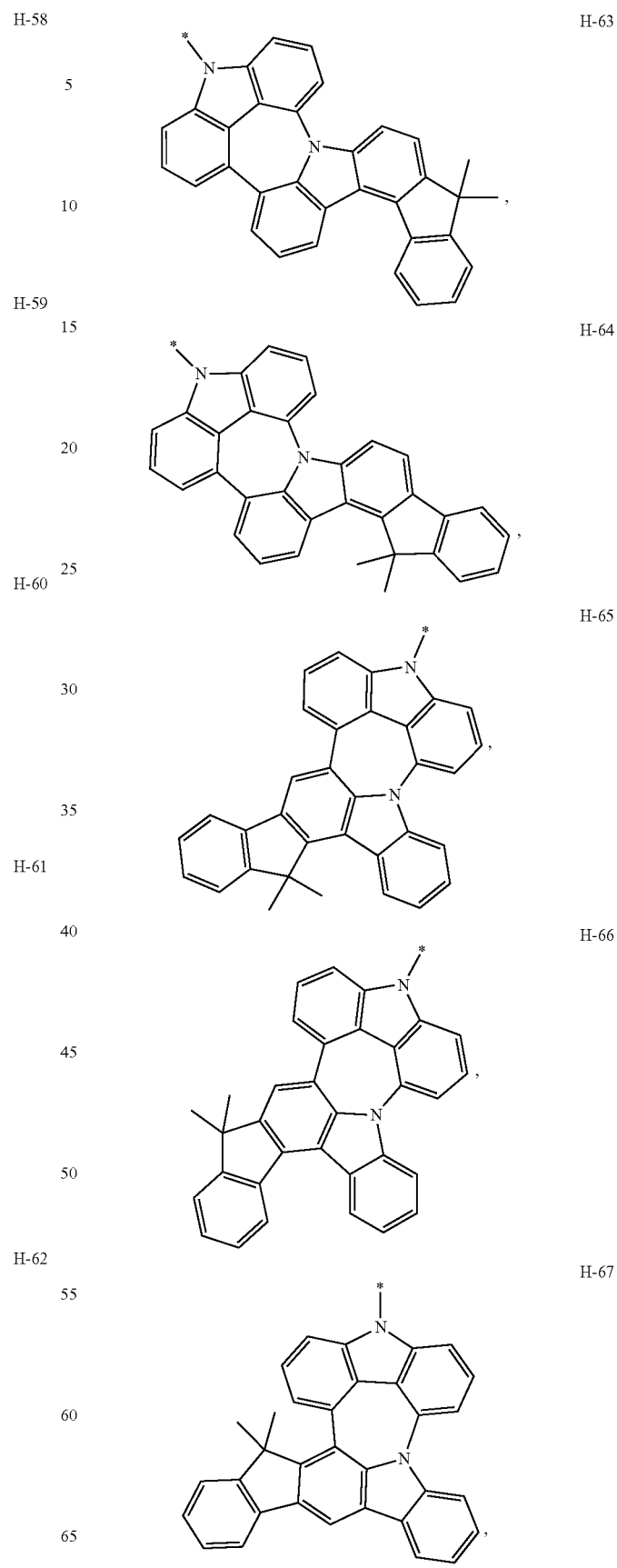

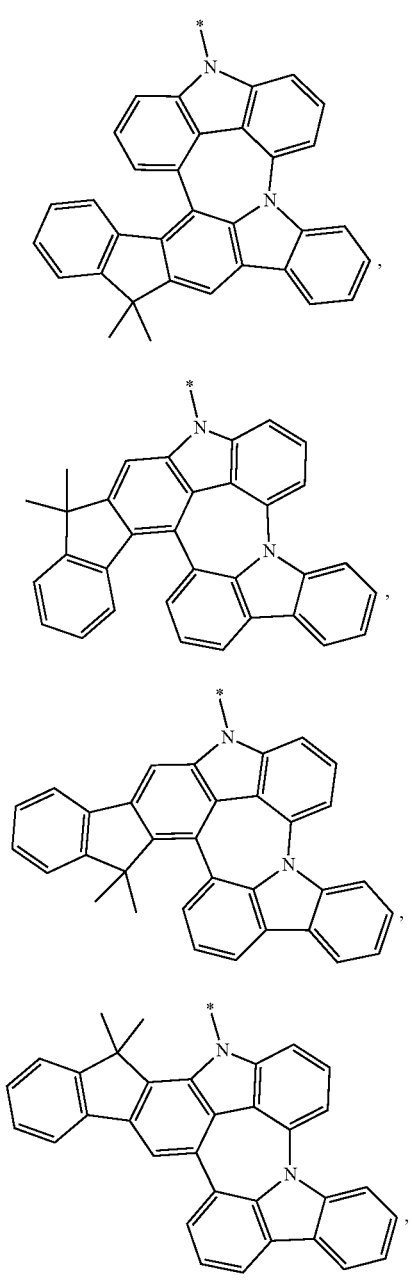
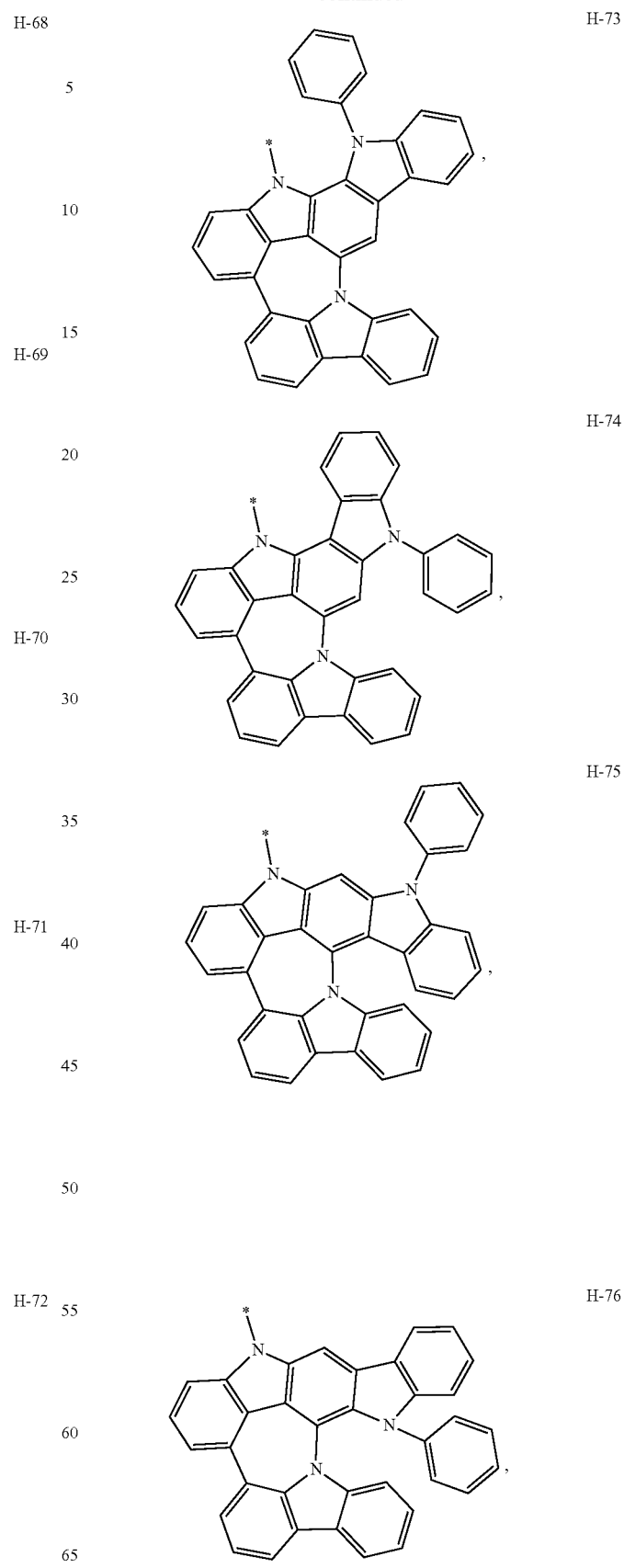

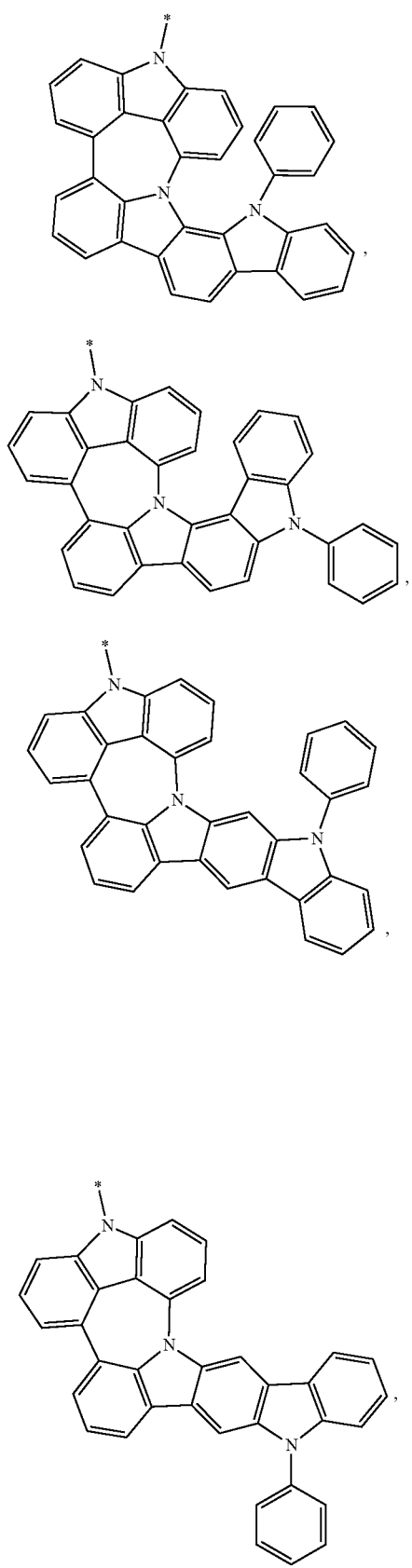
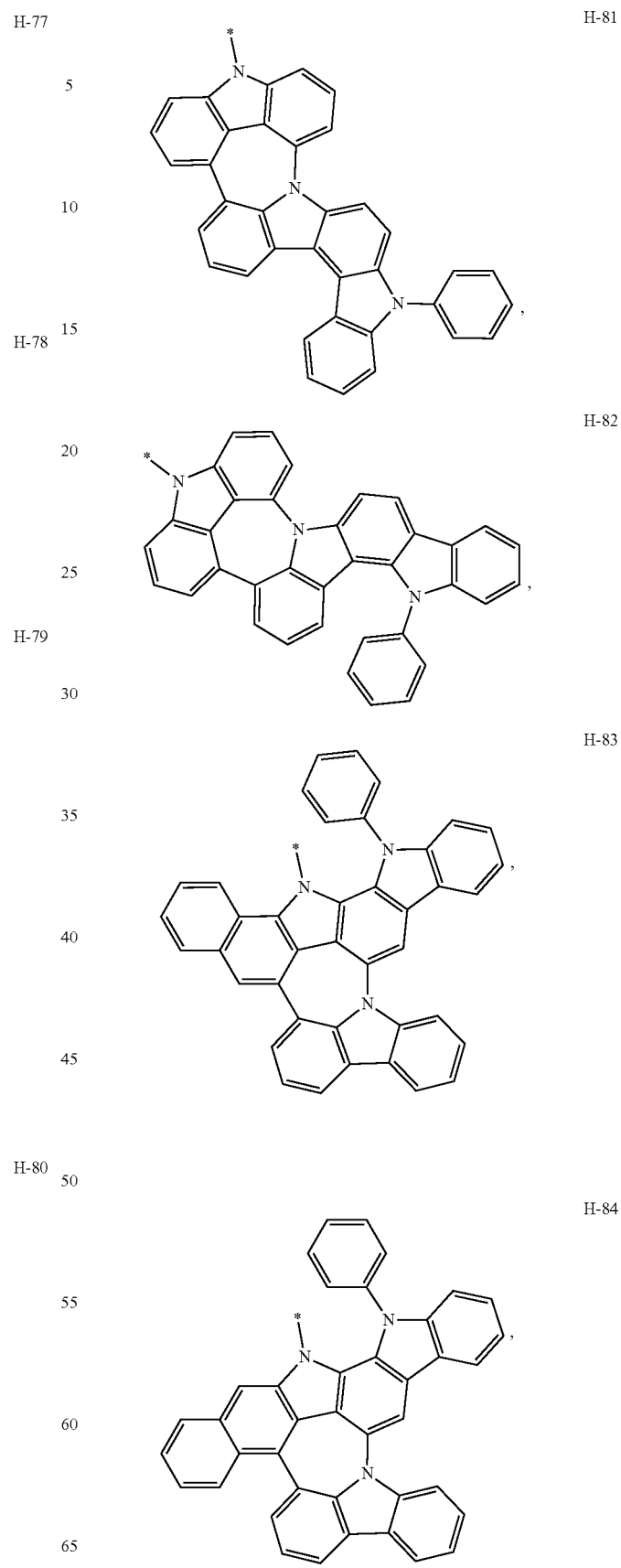

H-85
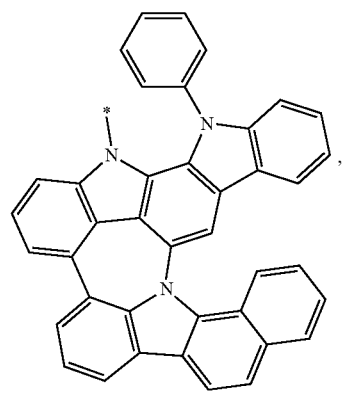
H-86
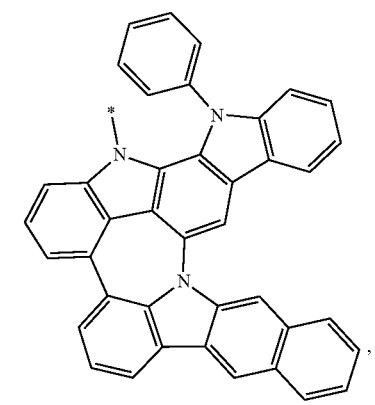
H-87
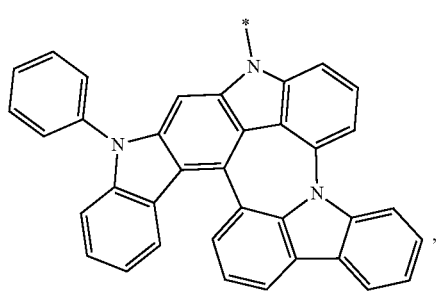
H-88
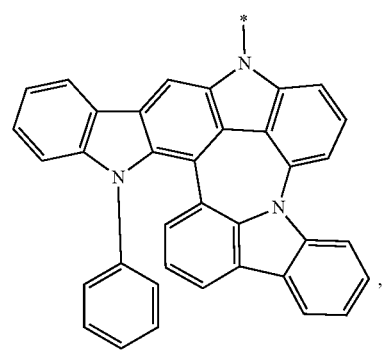
H-89
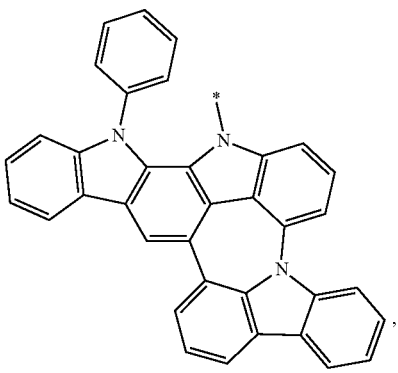
H-90
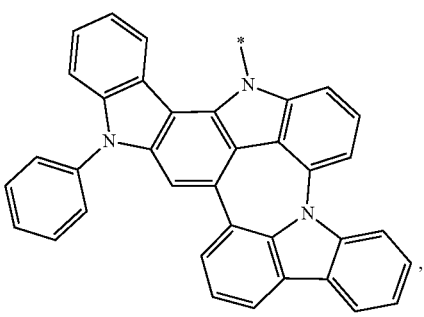
H-91
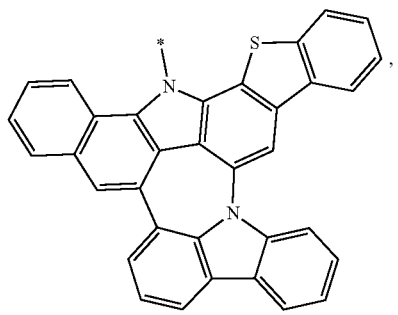
H-92
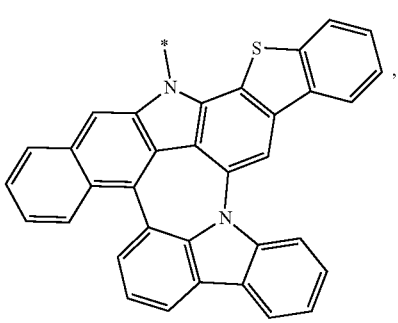

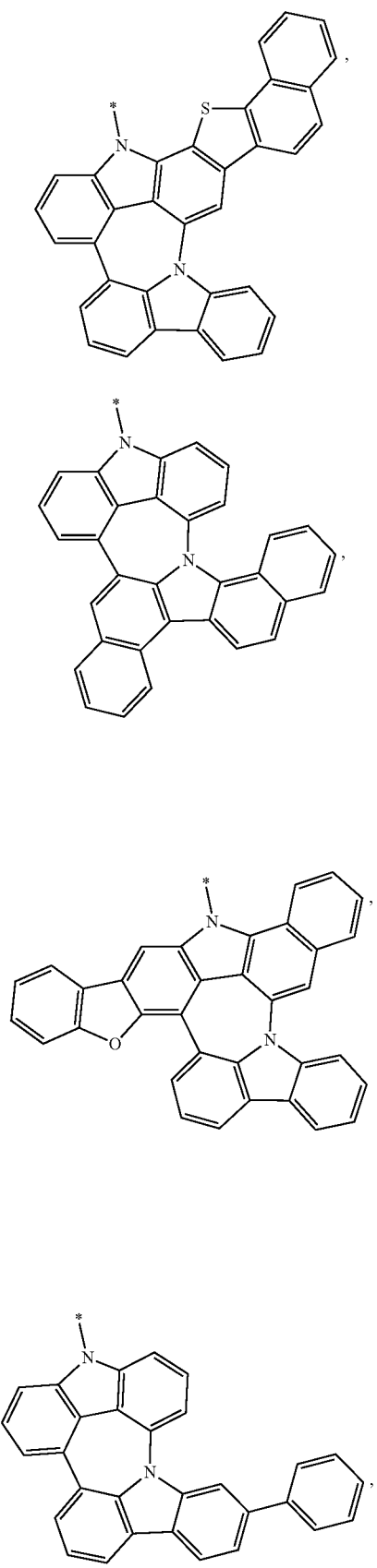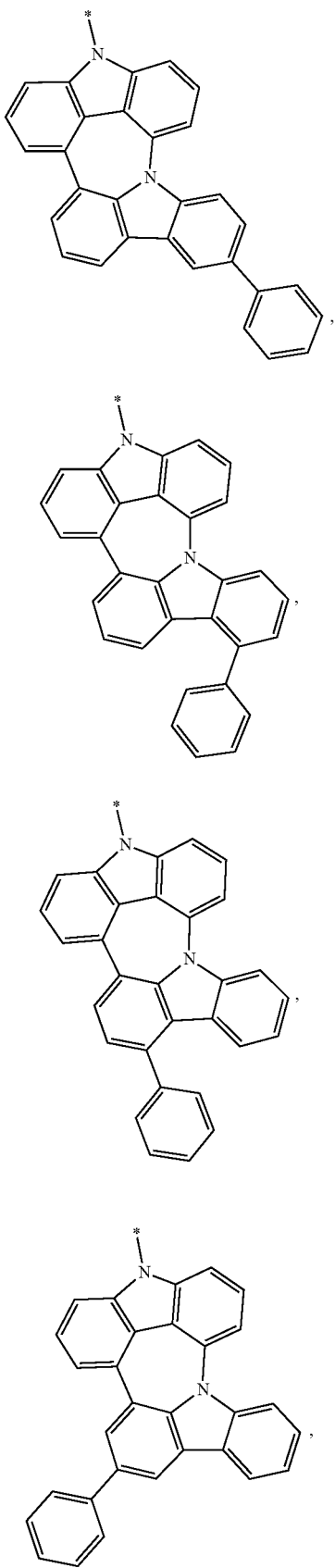

-continued
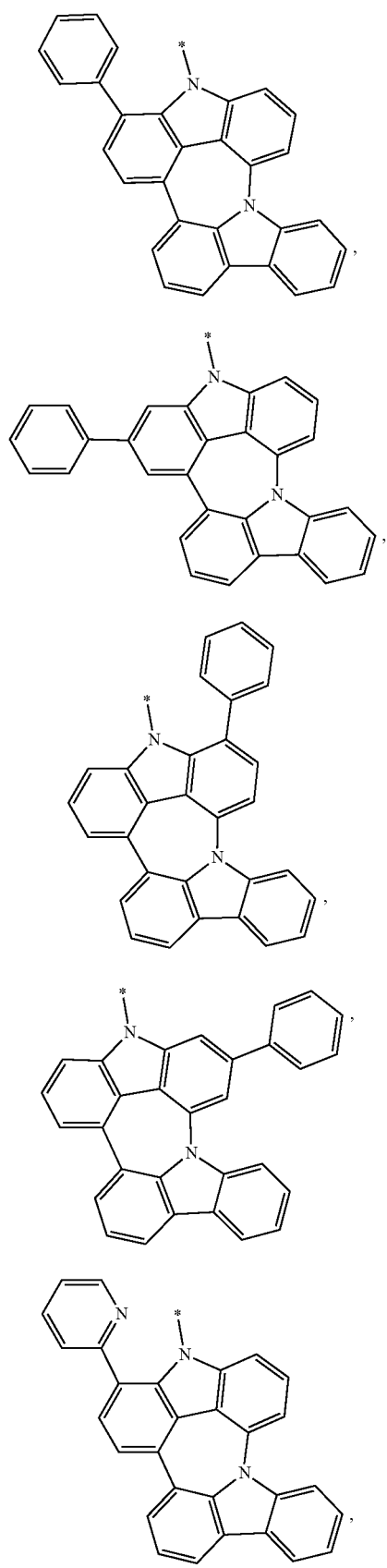
H-107
H-108
H-109
H-110
H-121
-continued
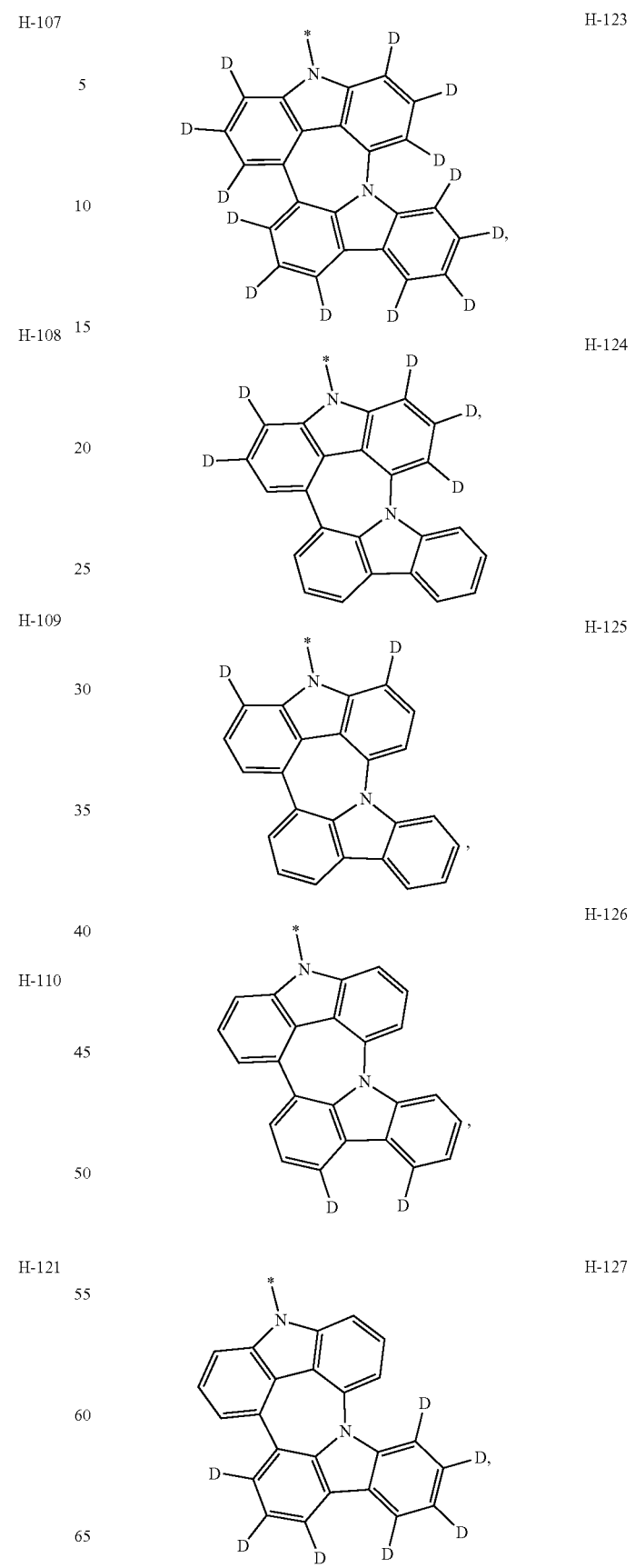
H-123
H-124
H-125
H-126
H-127

H-128 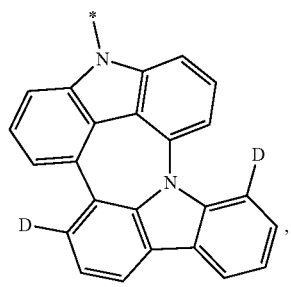
H-129 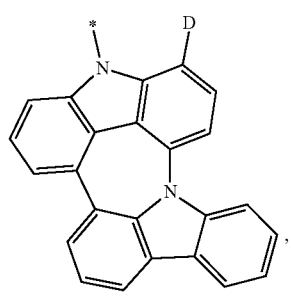
H-130 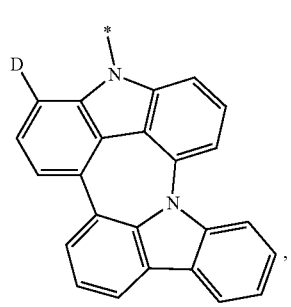
H-131 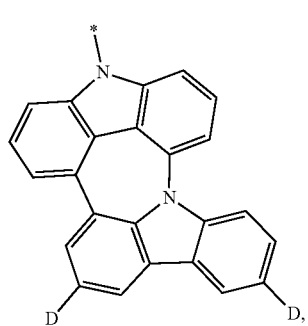
H-132 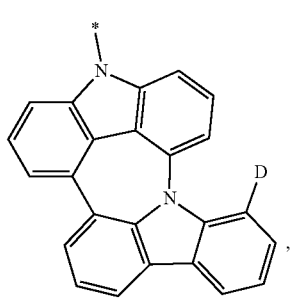
H-133 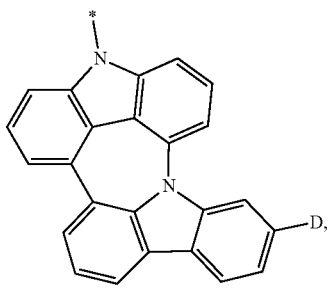
H-134 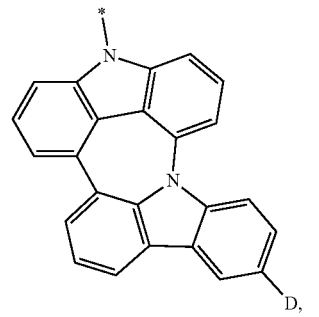
H-135 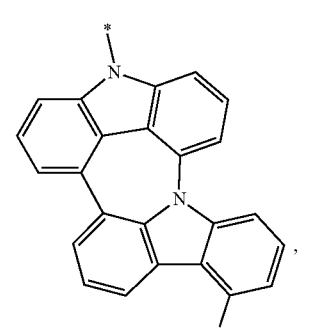
H-136 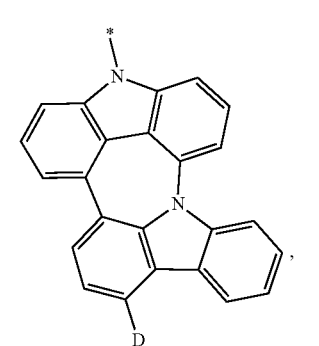
H-137 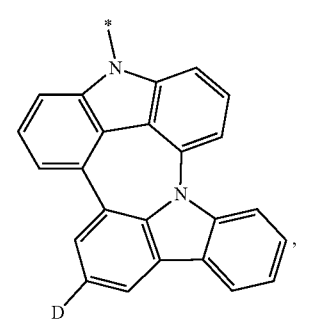

-continued

H-138

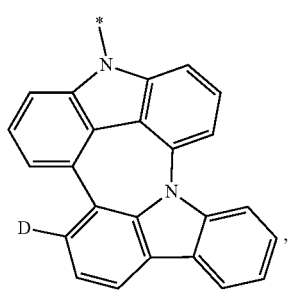
, and

H-139

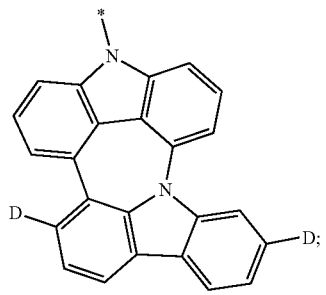
;

wherein, optionally, hydrogens in the structures of H-1 to H-95, H-102 to H-110, H-121, and H-123 to H-139 can be partially or completely substituted with deuterium.

7. The compound according to claim 1, wherein the E has a structure represented by Formula 2:

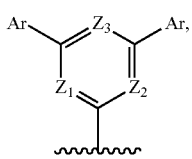

Formula 2 wherein $Z_1$ to $Z_3$ are each independently selected from N or $CR_z$, and at least two of $Z_1$ to $Z_3$ are N;

wherein $R_z$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, an isocyano group, a hydroxyl group, a sulfanyl group, and combinations thereof;

Ar is, at each occurrence identically or differently, selected from substituted or unsubstituted aryl having 6 to 18 carbon atoms or substituted or unsubstituted heteroaryl having 3 to 18 carbon atoms.

8. The compound according to claim 6, wherein the E is selected from the group consisting of the following structures:

E-1
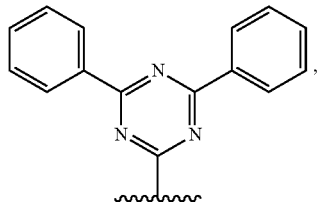
,

E-2
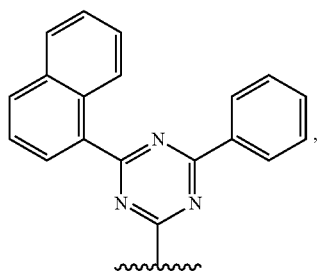
,

E-3
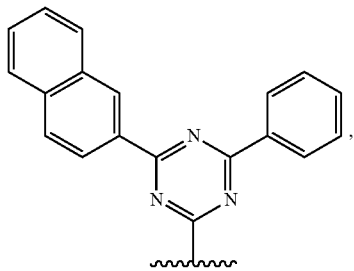
,

E-4
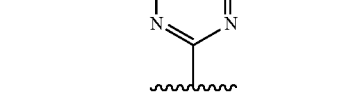
,

E-5
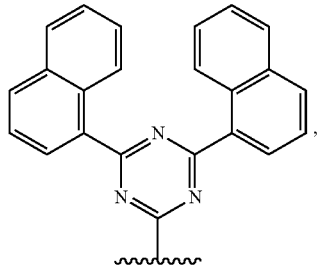
,

E-6
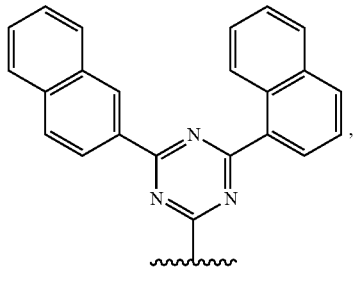
,

E-7
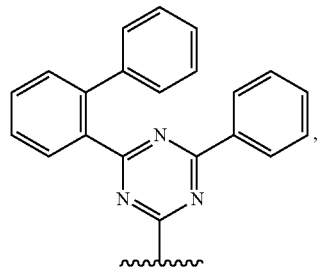
E-8
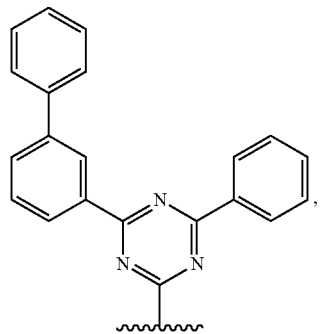
E-9
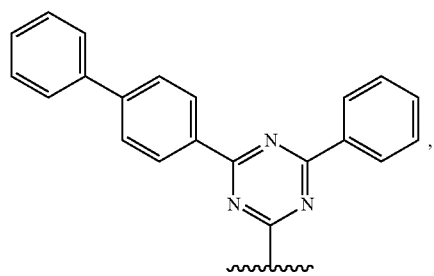
E-10
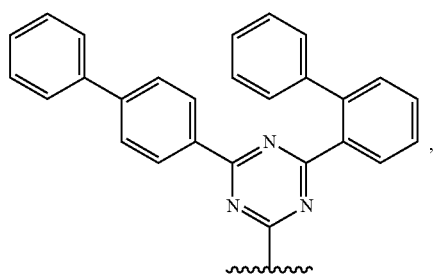
E-11
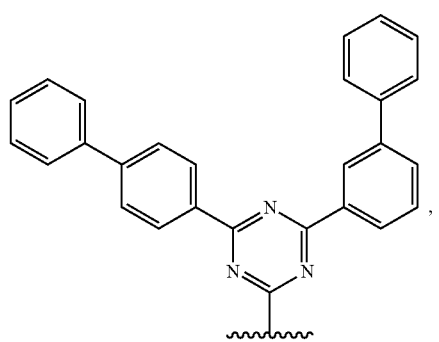
E-12
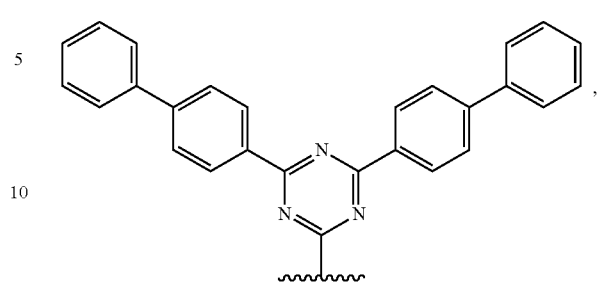
E-13
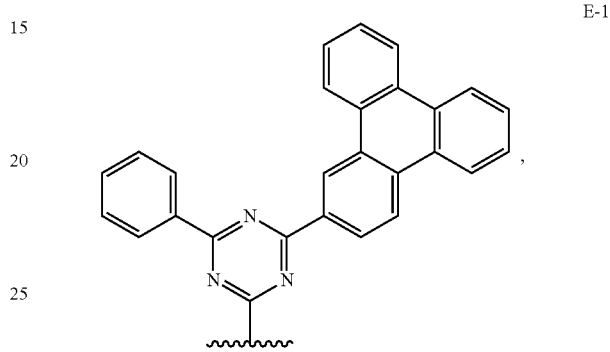
E-14
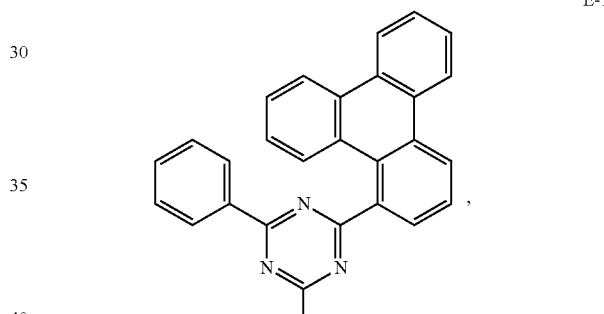
E-15
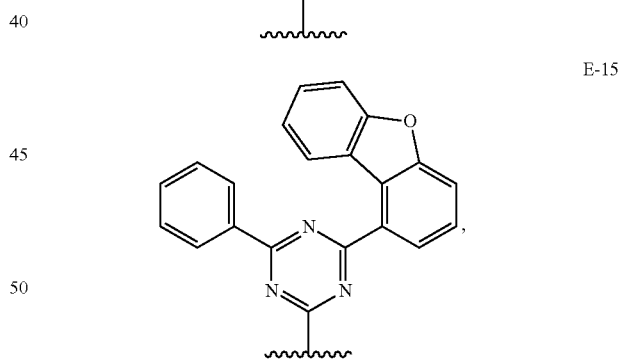
E-16
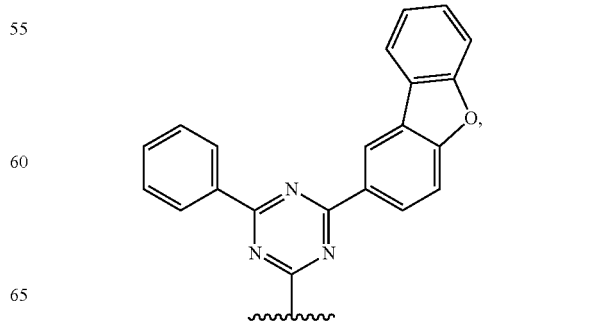

E-17
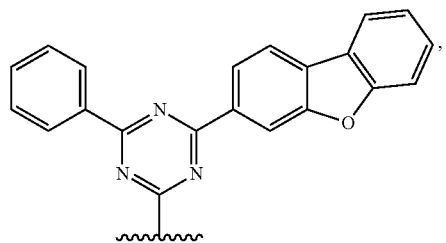
E-18
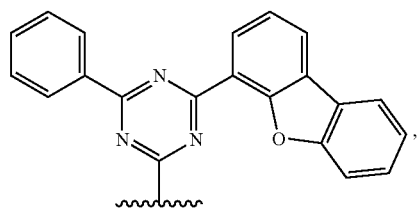
E-19
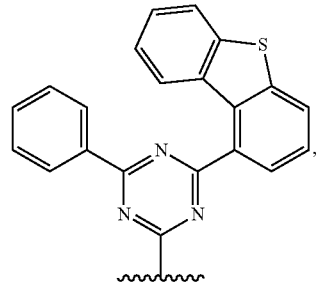
E-20
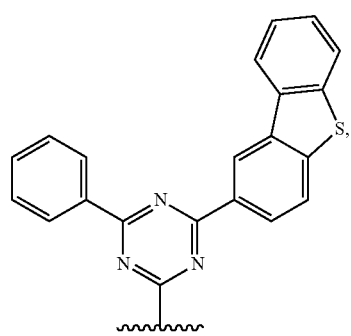
E-21
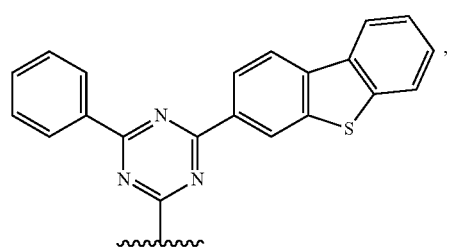
E-22
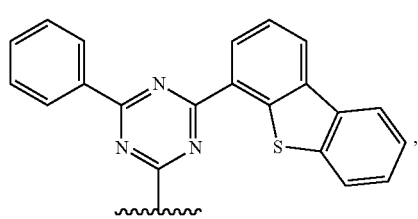
E-23
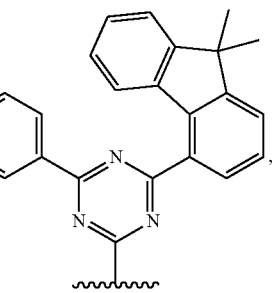
E-24
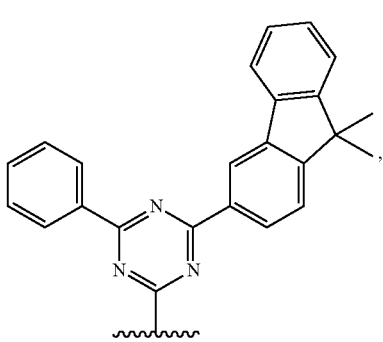
E-25
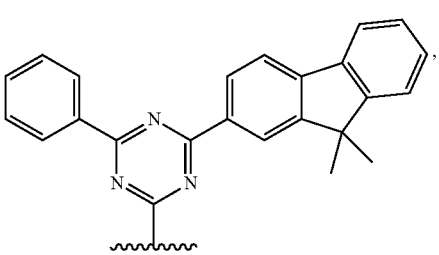
E-26
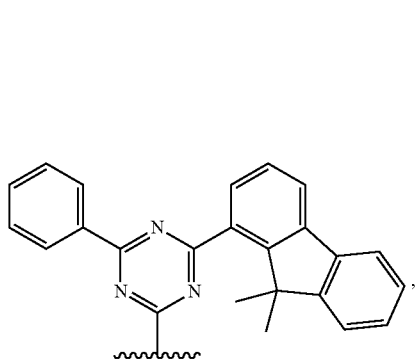
E-27
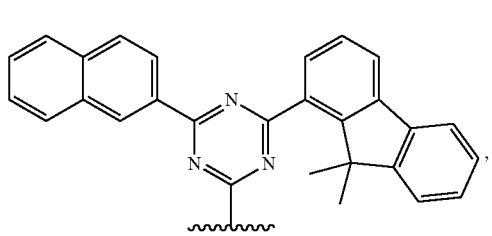

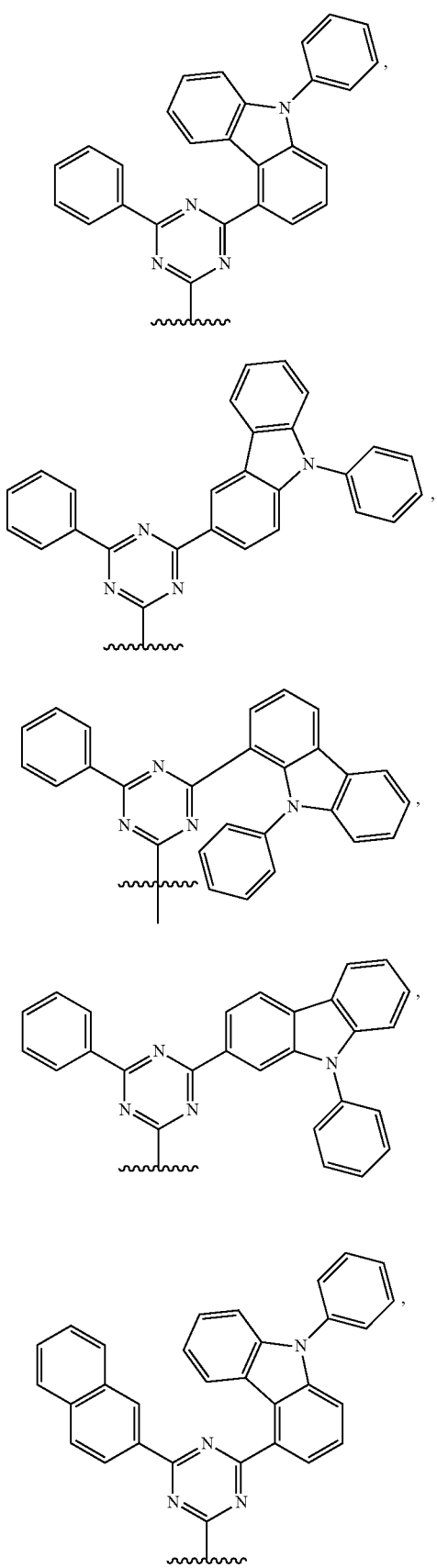
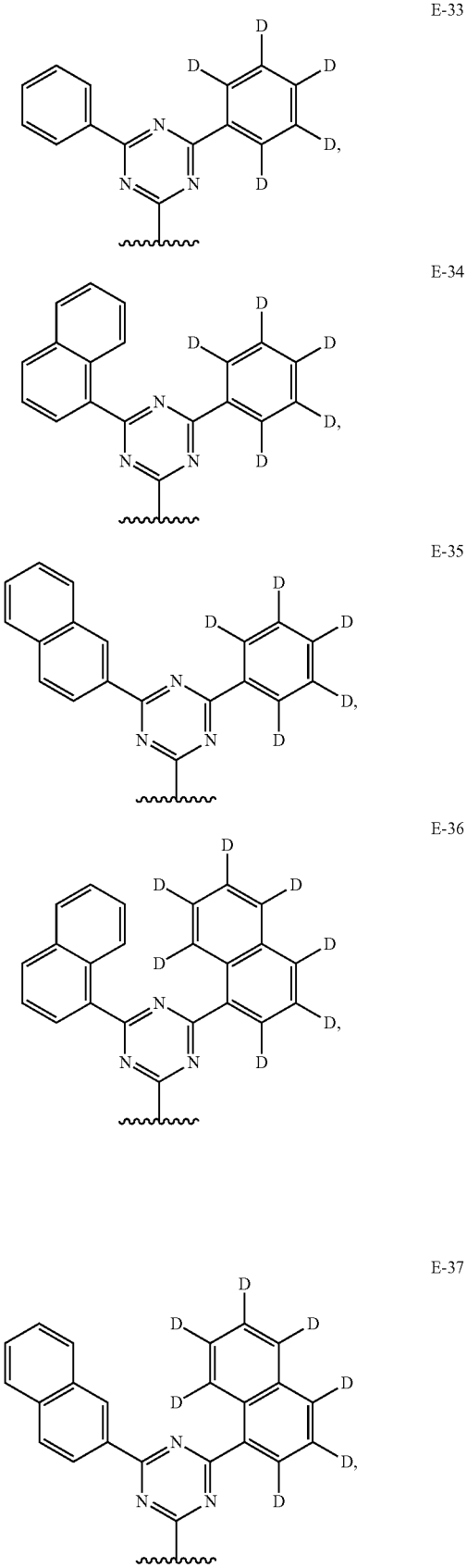

E-38
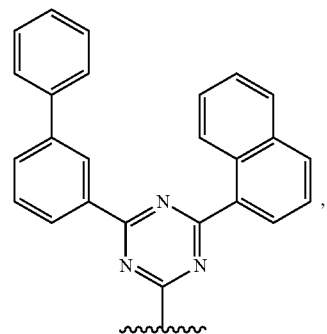
E-39
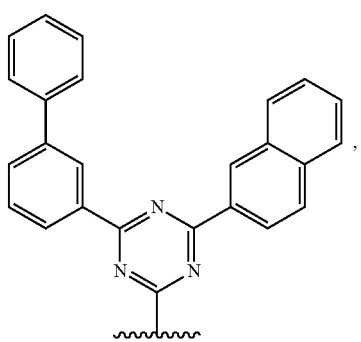
E-40
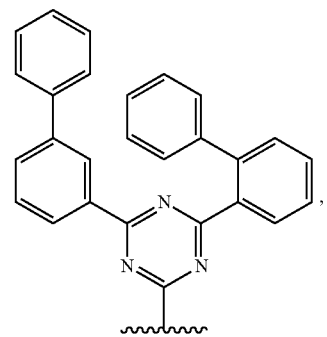
E-41
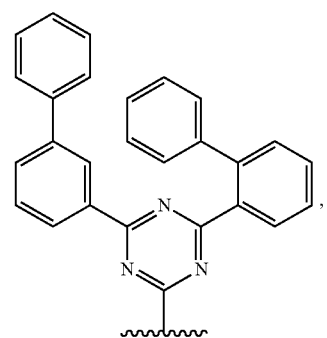
E-42
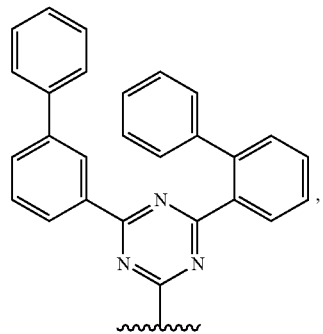
E-43
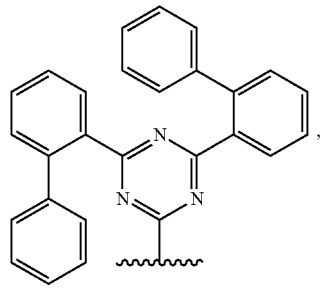
E-44
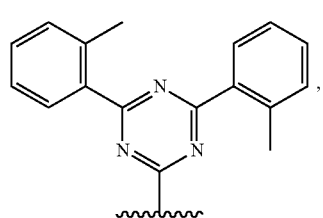
E-45
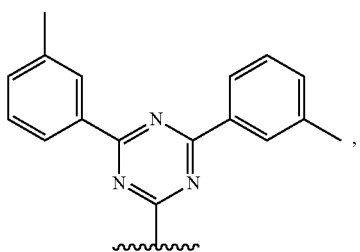
E-46
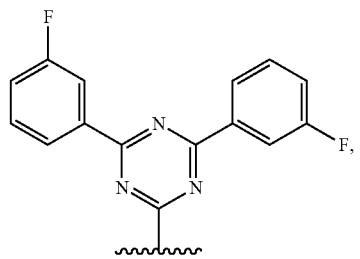
E-47
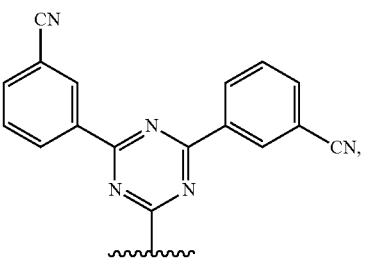

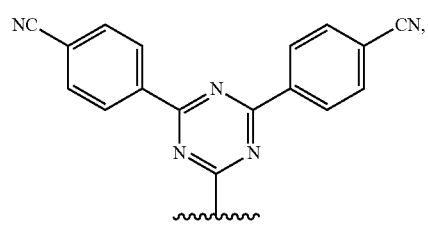 E-48
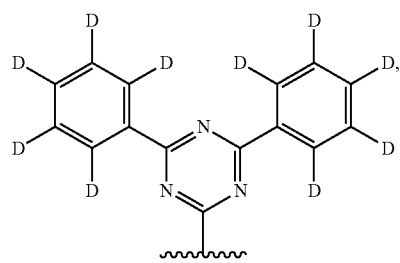 E-49
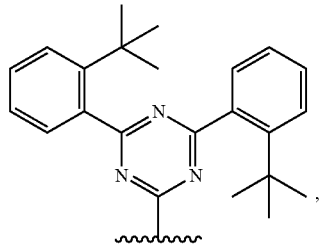 E-50
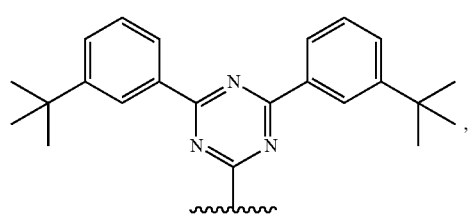 E-51
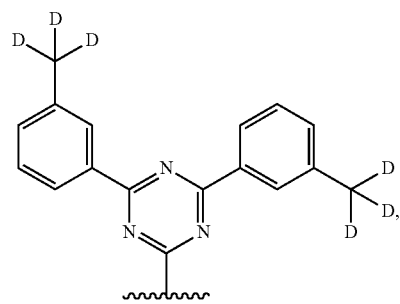 E-52
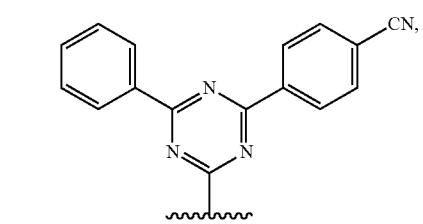 E-53
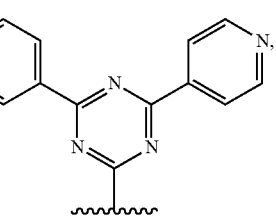 E-54
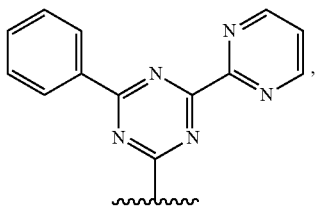 E-55
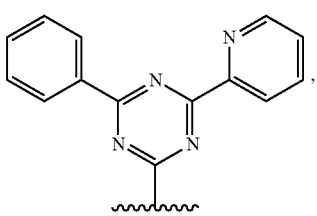 E-56
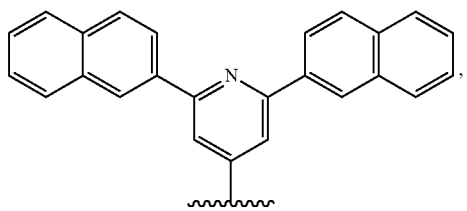 E-57
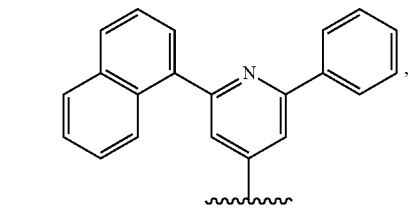 E-58
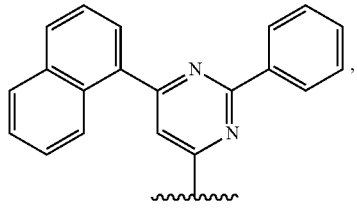 E-59
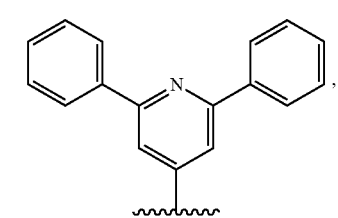 E-60

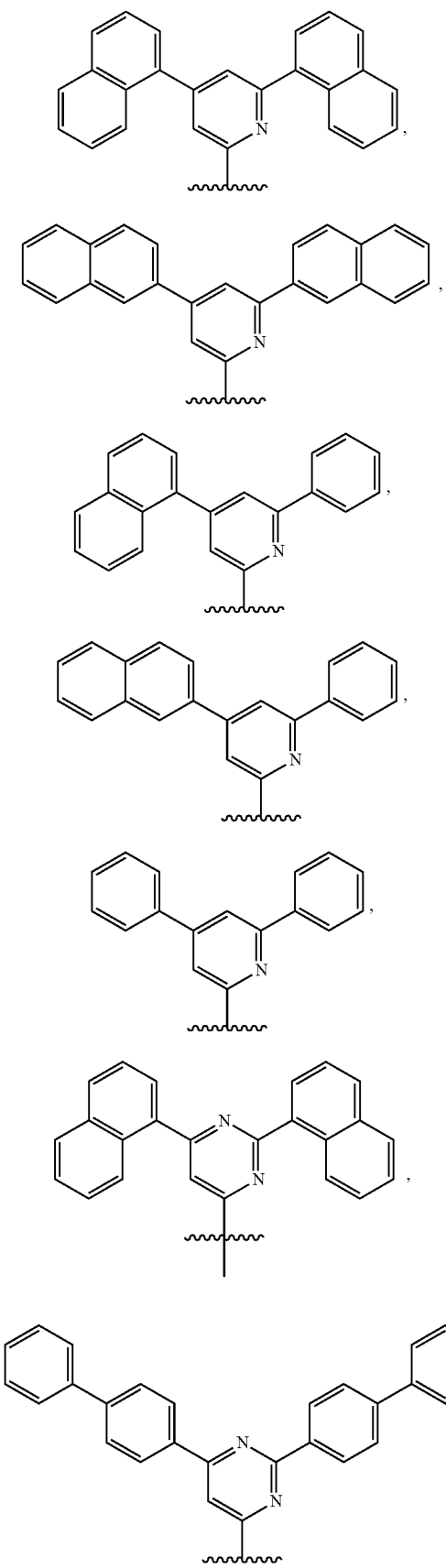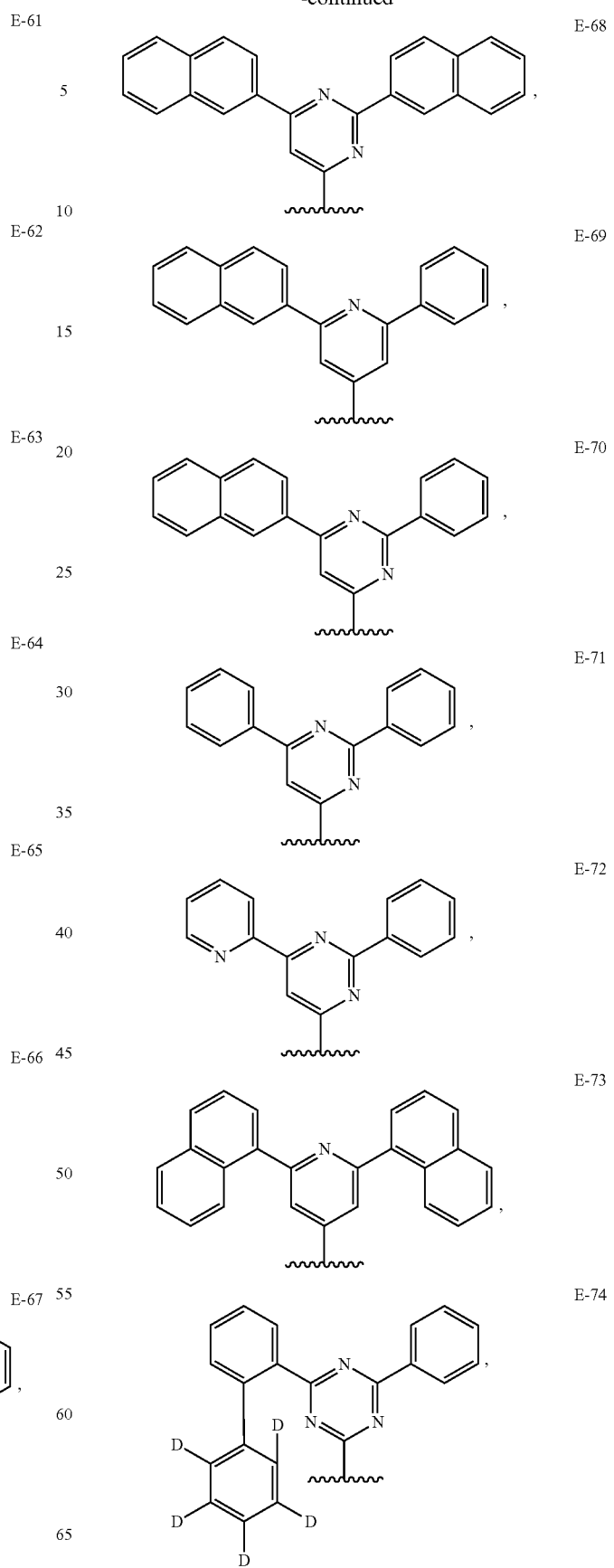

E-75
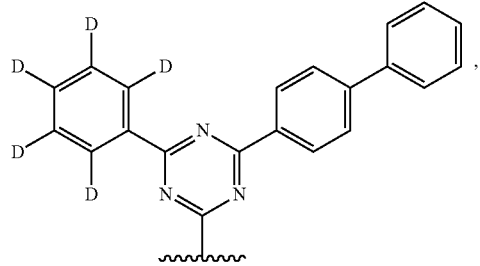
E-76
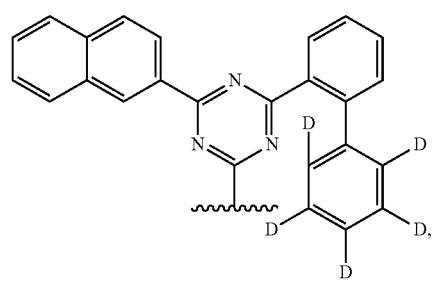
E-77
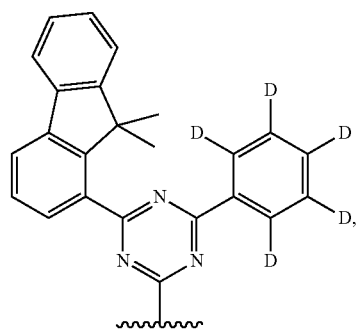
E-78
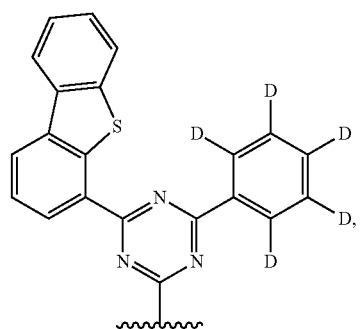
E-79
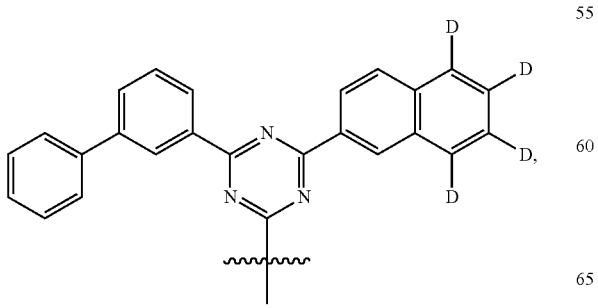
E-80
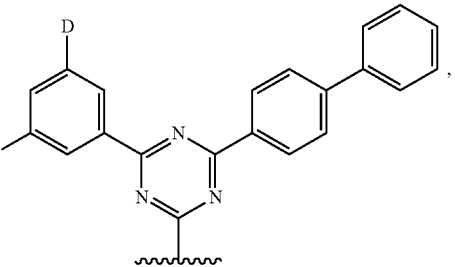
E-81
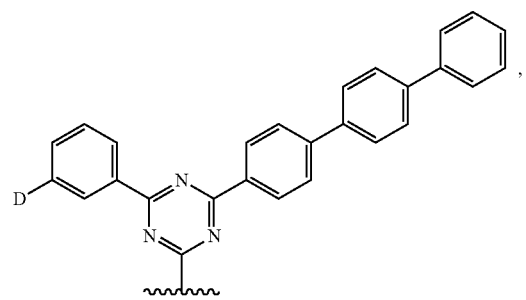
E-82
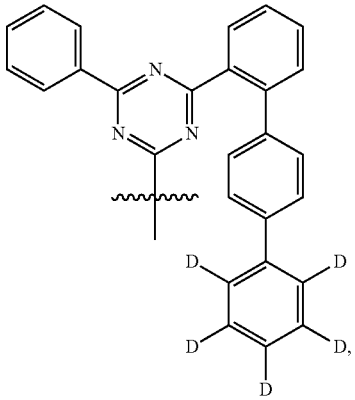
E-83
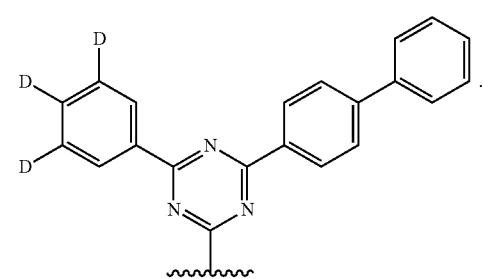
9. The compound according to claim 1, wherein the L has a structure represented by Formula 3:
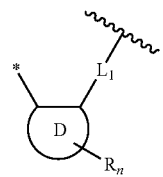
Formula 3
wherein the ring D is, at each occurrence identically or differently, selected from an aromatic ring having 6 to 18 carbon atoms or a heteroaromatic ring having 3 to 18 carbon atoms; $R_n$ and $R_m$ are, at each occurrence identically or differently, selected from the group consisting of: hydrogen, deuterium, halogen, substituted or unsubstituted alkyl having 1 to 20 carbon atoms, substituted or unsubstituted arylalkyl having 7 to 30 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, an isocyano group, a hydroxyl group, a sulfanyl group, and combinations thereof; adjacent substituents $R_n$, $R_m$ can be optionally joined to form a ring.

10. The compound according to claim 8, wherein L is selected from the group consisting of the following structures:

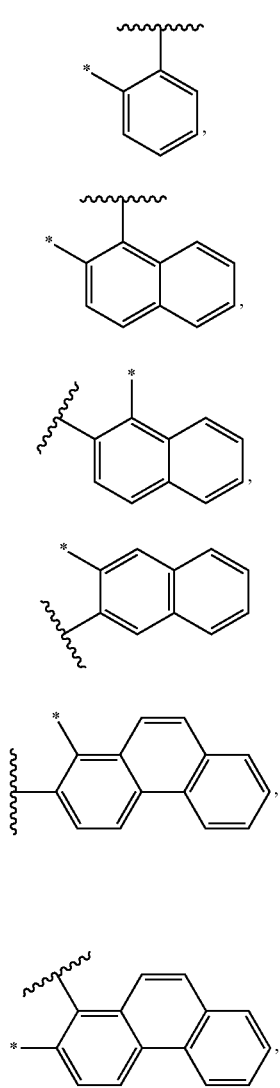

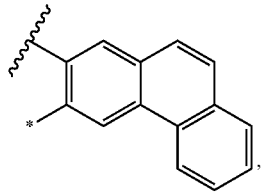

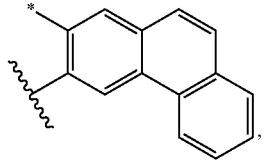

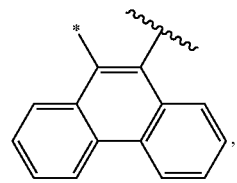

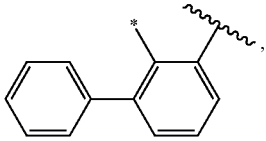

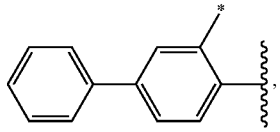

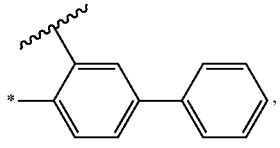

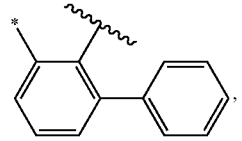

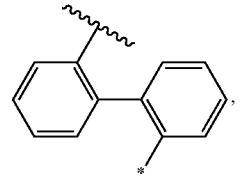

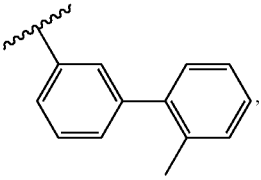

L-16
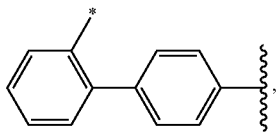
L-17
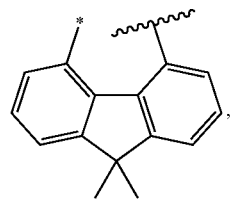
L-18
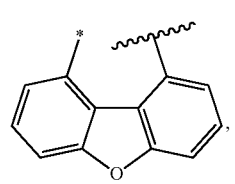
L-19
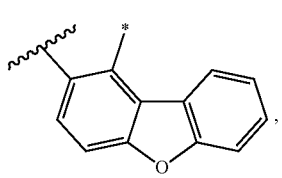
L-20
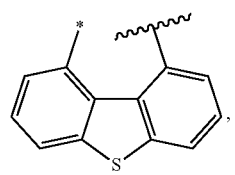
L-21
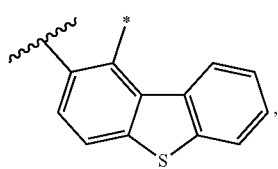
L-22
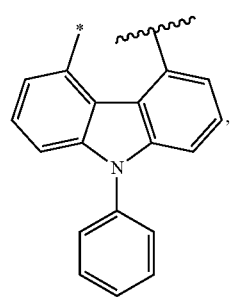
L-23
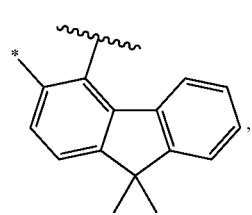
L-24
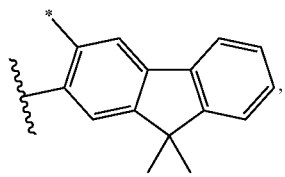
L-25
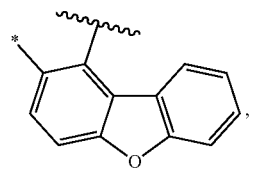
L-26
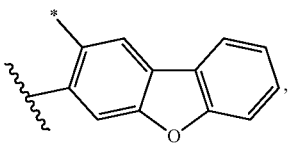
L-27
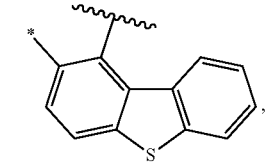
L-28
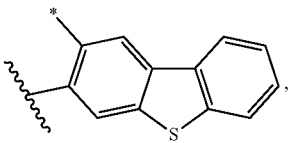
L-29
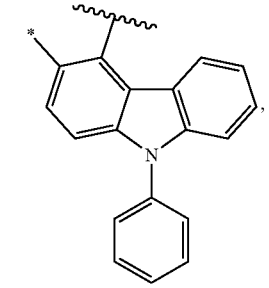
L-30
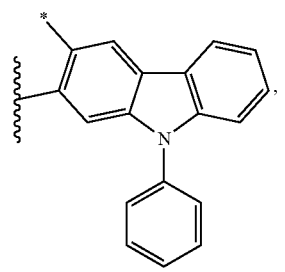
L-31
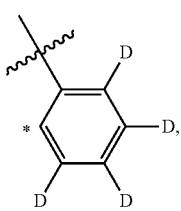

-continued

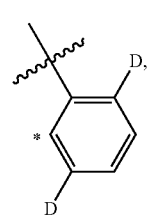
L-32

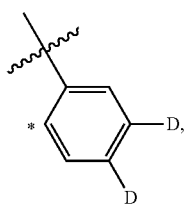
L-33

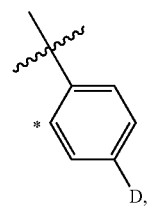
L-34

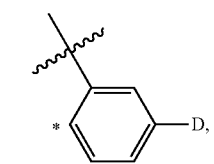
L-35

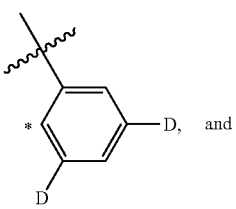
L-36, and

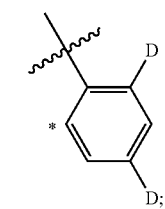
L-37 wherein in the structures of L-1 to L-37, "*" represents the position where the structures are connected to the structure H represented by Formula 1, and "⁓" represents the position where the structures are connected to the structure E represented by Formula 2;

wherein, optionally, hydrogens in the structures of L-1 to L-37 can be partially or completely substituted with deuterium.

11. The compound according to claim 10, wherein the compound is selected from the group consisting of Compound 1 to Compound 625, Compounds 632 to Compound 640, Compound 651, Compounds 653 to Compound 763, Compound 770 to Compound 778, Compound 789, Compound 791 to Compound 901, Compound 908 to Compound 916, Compound 927, Compound 929 to Compound 1000, and the Compound 1 to Compound 625, Compound 632 to Compound 640, Compound 651, Compound 653 to Compound 763, Compound 770 to Compound 778, Compounds 789, Compound 791 to Compound 901, Compound 908 to Compound 916, Compound 927, Compound 929 to Compound 1000, wherein each has a structure of H-L-E, wherein H, L, and E are selected from structures in the following table, respectively:

| Compound No. | H | L | E |
|---|---|---|---|
| 1 | H-1 | L-1 | E-1 |
| 2 | H-1 | L-1 | E-2 |
| 3 | H-1 | L-1 | E-3 |
| 4 | H-1 | L-1 | E-4 |
| 5 | H-1 | L-1 | E-5 |
| 6 | H-1 | L-1 | E-6 |
| 7 | H-1 | L-1 | E-7 |
| 8 | H-1 | L-1 | E-8 |
| 9 | H-1 | L-1 | E-9 |
| 10 | H-1 | L-1 | E-10 |
| 11 | H-1 | L-1 | E-11 |
| 12 | H-1 | L-1 | E-12 |
| 13 | H-1 | L-1 | E-13 |
| 14 | H-1 | L-1 | E-14 |
| 15 | H-1 | L-1 | E-15 |
| 16 | H-1 | L-1 | E-16 |
| 17 | H-1 | L-1 | E-17 |
| 18 | H-1 | L-1 | E-18 |
| 19 | H-1 | L-1 | E-19 |
| 20 | H-1 | L-1 | E-20 |
| 21 | H-1 | L-1 | E-21 |
| 22 | H-1 | L-1 | E-22 |
| 23 | H-1 | L-1 | E-23 |
| 24 | H-1 | L-1 | E-24 |
| 25 | H-1 | L-1 | E-25 |
| 26 | H-1 | L-1 | E-26 |
| 27 | H-1 | L-1 | E-27 |
| 28 | H-1 | L-1 | E-28 |
| 29 | H-1 | L-1 | E-29 |
| 30 | H-1 | L-1 | E-30 |
| 31 | H-1 | L-1 | E-31 |
| 32 | H-1 | L-1 | E-32 |
| 33 | H-1 | L-1 | E-33 |
| 34 | H-1 | L-1 | E-34 |
| 35 | H-1 | L-1 | E-35 |
| 36 | H-1 | L-1 | E-36 |
| 37 | H-1 | L-1 | E-37 |
| 38 | H-1 | L-1 | E-38 |
| 39 | H-1 | L-1 | E-39 |
| 40 | H-1 | L-1 | E-40 |
| 41 | H-1 | L-1 | E-41 |
| 42 | H-1 | L-1 | E-42 |
| 43 | H-1 | L-1 | E-43 |
| 44 | H-1 | L-1 | E-44 |
| 45 | H-1 | L-1 | E-45 |
| 46 | H-1 | L-1 | E-46 |
| 47 | H-1 | L-1 | E-47 |
| 48 | H-1 | L-1 | E-48 |
| 49 | H-1 | L-1 | E-49 |
| 50 | H-1 | L-1 | E-50 |
| 51 | H-1 | L-1 | E-51 |
| 52 | H-1 | L-1 | E-52 |
| 53 | H-1 | L-1 | E-53 |
| 54 | H-1 | L-2 | E-1 |
| 55 | H-1 | L-2 | E-2 |
| 56 | H-1 | L-2 | E-3 |
| 57 | H-1 | L-2 | E-4 |
| 58 | H-1 | L-2 | E-5 |
| 59 | H-1 | L-2 | E-6 |
| 60 | H-1 | L-2 | E-7 |
| 61 | H-1 | L-2 | E-8 |
| 62 | H-1 | L-2 | E-9 |
| 63 | H-1 | L-2 | E-10 |
| 64 | H-1 | L-2 | E-11 |
| 65 | H-1 | L-2 | E-12 |
| 66 | H-1 | L-2 | E-13 |
| 67 | H-1 | L-2 | E-14 |
| 68 | H-1 | L-2 | E-15 |
| 69 | H-1 | L-2 | E-16 |

| Compound No. | H | L | E |
|---|---|---|---|
| 70 | H-1 | L-2 | E-17 |
| 71 | H-1 | L-2 | E-18 |
| 72 | H-1 | L-2 | E-19 |
| 73 | H-1 | L-2 | E-20 |
| 74 | H-1 | L-2 | E-21 |
| 75 | H-1 | L-2 | E-22 |
| 76 | H-1 | L-2 | E-23 |
| 77 | H-1 | L-2 | E-24 |
| 78 | H-1 | L-2 | E-25 |
| 79 | H-1 | L-2 | E-26 |
| 80 | H-1 | L-2 | E-27 |
| 81 | H-1 | L-2 | E-28 |
| 82 | H-1 | L-2 | E-29 |
| 83 | H-1 | L-2 | E-30 |
| 84 | H-1 | L-2 | E-31 |
| 85 | H-1 | L-2 | E-32 |
| 86 | H-1 | L-2 | E-33 |
| 87 | H-1 | L-2 | E-34 |
| 88 | H-1 | L-2 | E-35 |
| 89 | H-1 | L-2 | E-36 |
| 90 | H-1 | L-2 | E-37 |
| 91 | H-1 | L-2 | E-38 |
| 92 | H-1 | L-2 | E-39 |
| 93 | H-1 | L-2 | E-40 |
| 94 | H-1 | L-2 | E-41 |
| 95 | H-1 | L-2 | E-42 |
| 96 | H-1 | L-2 | E-43 |
| 97 | H-1 | L-2 | E-44 |
| 98 | H-1 | L-2 | E-45 |
| 99 | H-1 | L-2 | E-46 |
| 100 | H-1 | L-2 | E-47 |
| 101 | H-1 | L-2 | E-48 |
| 102 | H-1 | L-2 | E-49 |
| 103 | H-1 | L-2 | E-50 |
| 104 | H-1 | L-2 | E-51 |
| 105 | H-1 | L-2 | E-52 |
| 106 | H-1 | L-2 | E-53 |
| 107 | H-1 | L-17 | E-1 |
| 108 | H-1 | L-3 | E-1 |
| 109 | H-1 | L-3 | E-2 |
| 110 | H-1 | L-3 | E-3 |
| 111 | H-1 | L-3 | E-4 |
| 112 | H-1 | L-3 | E-5 |
| 113 | H-1 | L-3 | E-6 |
| 114 | H-1 | L-3 | E-7 |
| 115 | H-1 | L-3 | E-8 |
| 116 | H-1 | L-3 | E-9 |
| 117 | H-1 | L-3 | E-10 |
| 118 | H-1 | L-3 | E-11 |
| 119 | H-1 | L-3 | E-12 |
| 120 | H-1 | L-3 | E-13 |
| 121 | H-1 | L-3 | E-14 |
| 122 | H-1 | L-3 | E-15 |
| 123 | H-1 | L-3 | E-16 |
| 124 | H-1 | L-3 | E-17 |
| 125 | H-1 | L-3 | E-18 |
| 126 | H-1 | L-3 | E-19 |
| 127 | H-1 | L-3 | E-20 |
| 128 | H-1 | L-3 | E-21 |
| 129 | H-1 | L-3 | E-22 |
| 130 | H-1 | L-3 | E-23 |
| 131 | H-1 | L-3 | E-24 |
| 132 | H-1 | L-3 | E-25 |
| 133 | H-1 | L-3 | E-26 |
| 134 | H-1 | L-3 | E-27 |
| 135 | H-1 | L-3 | E-28 |
| 136 | H-1 | L-3 | E-29 |
| 137 | H-1 | L-3 | E-30 |
| 138 | H-1 | L-3 | E-31 |
| 139 | H-1 | L-3 | E-32 |
| 140 | H-1 | L-3 | E-33 |
| 141 | H-1 | L-3 | E-34 |
| 142 | H-1 | L-3 | E-35 |
| 143 | H-1 | L-3 | E-36 |
| 144 | H-1 | L-3 | E-37 |
| 145 | H-1 | L-3 | E-38 |
| 146 | H-1 | L-3 | E-39 |
| 147 | H-1 | L-3 | E-40 |
| 148 | H-1 | L-3 | E-41 |
| 149 | H-1 | L-3 | E-42 |
| 150 | H-1 | L-3 | E-43 |
| 151 | H-1 | L-3 | E-44 |
| 152 | H-1 | L-3 | E-45 |
| 153 | H-1 | L-3 | E-46 |
| 154 | H-1 | L-3 | E-47 |
| 155 | H-1 | L-3 | E-48 |
| 156 | H-1 | L-3 | E-49 |
| 157 | H-1 | L-3 | E-50 |
| 158 | H-1 | L-3 | E-51 |
| 159 | H-1 | L-3 | E-52 |
| 160 | H-1 | L-3 | E-53 |
| 161 | H-1 | L-4 | E-1 |
| 162 | H-1 | L-4 | E-2 |
| 163 | H-1 | L-4 | E-3 |
| 164 | H-1 | L-4 | E-4 |
| 165 | H-1 | L-4 | E-5 |
| 166 | H-1 | L-4 | E-6 |
| 167 | H-1 | L-4 | E-7 |
| 168 | H-1 | L-4 | E-8 |
| 169 | H-1 | L-4 | E-9 |
| 170 | H-1 | L-4 | E-10 |
| 171 | H-1 | L-4 | E-11 |
| 172 | H-1 | L-4 | E-12 |
| 173 | H-1 | L-4 | E-13 |
| 174 | H-1 | L-4 | E-14 |
| 175 | H-1 | L-4 | E-15 |
| 176 | H-1 | L-4 | E-16 |
| 177 | H-1 | L-4 | E-17 |
| 178 | H-1 | L-4 | E-18 |
| 179 | H-1 | L-4 | E-19 |
| 180 | H-1 | L-4 | E-20 |
| 181 | H-1 | L-4 | E-21 |
| 182 | H-1 | L-4 | E-22 |
| 183 | H-1 | L-4 | E-23 |
| 184 | H-1 | L-4 | E-24 |
| 185 | H-1 | L-4 | E-25 |
| 186 | H-1 | L-4 | E-26 |
| 187 | H-1 | L-4 | E-27 |
| 188 | H-1 | L-4 | E-28 |
| 189 | H-1 | L-4 | E-29 |
| 190 | H-1 | L-4 | E-30 |
| 191 | H-1 | L-4 | E-31 |
| 192 | H-1 | L-4 | E-32 |
| 193 | H-1 | L-4 | E-33 |
| 194 | H-1 | L-4 | E-34 |
| 195 | H-1 | L-4 | E-35 |
| 196 | H-1 | L-4 | E-36 |
| 197 | H-1 | L-4 | E-37 |
| 198 | H-1 | L-4 | E-38 |
| 199 | H-1 | L-4 | E-39 |
| 200 | H-1 | L-4 | E-40 |
| 201 | H-1 | L-4 | E-41 |
| 202 | H-1 | L-4 | E-42 |
| 203 | H-1 | L-4 | E-43 |
| 204 | H-1 | L-4 | E-44 |
| 205 | H-1 | L-4 | E-45 |
| 206 | H-1 | L-4 | E-46 |
| 207 | H-1 | L-4 | E-47 |
| 208 | H-1 | L-4 | E-48 |
| 209 | H-1 | L-4 | E-49 |
| 210 | H-1 | L-4 | E-50 |
| 211 | H-1 | L-4 | E-51 |
| 212 | H-1 | L-4 | E-52 |
| 213 | H-1 | L-4 | E-53 |
| 214 | H-1 | L-9 | E-1 |
| 215 | H-1 | L-9 | E-2 |
| 216 | H-1 | L-9 | E-3 |
| 217 | H-1 | L-9 | E-4 |
| 218 | H-1 | L-9 | E-5 |
| 219 | H-1 | L-9 | E-6 |
| 220 | H-1 | L-9 | E-7 |
| 221 | H-1 | L-9 | E-8 |
| 222 | H-1 | L-9 | E-9 |
| 223 | H-1 | L-9 | E-10 |

| Compound No. | H | L | E |
| --- | --- | --- | --- |
| 224 | H-1 | L-9 | E-11 |
| 225 | H-1 | L-9 | E-12 |
| 226 | H-1 | L-9 | E-13 |
| 227 | H-1 | L-9 | E-14 |
| 228 | H-1 | L-9 | E-15 |
| 229 | H-1 | L-9 | E-16 |
| 230 | H-1 | L-9 | E-17 |
| 231 | H-1 | L-9 | E-18 |
| 232 | H-1 | L-9 | E-19 |
| 233 | H-1 | L-9 | E-20 |
| 234 | H-1 | L-9 | E-21 |
| 235 | H-1 | L-9 | E-22 |
| 236 | H-1 | L-9 | E-23 |
| 237 | H-1 | L-9 | E-24 |
| 238 | H-1 | L-9 | E-25 |
| 239 | H-1 | L-9 | E-26 |
| 240 | H-1 | L-9 | E-27 |
| 241 | H-1 | L-9 | E-28 |
| 242 | H-1 | L-9 | E-29 |
| 243 | H-1 | L-9 | E-30 |
| 244 | H-1 | L-9 | E-31 |
| 245 | H-1 | L-9 | E-32 |
| 246 | H-1 | L-9 | E-33 |
| 247 | H-1 | L-9 | E-34 |
| 248 | H-1 | L-9 | E-35 |
| 249 | H-1 | L-9 | E-36 |
| 250 | H-1 | L-9 | E-37 |
| 251 | H-1 | L-9 | E-38 |
| 252 | H-1 | L-9 | E-39 |
| 253 | H-1 | L-9 | E-40 |
| 254 | H-1 | L-9 | E-41 |
| 255 | H-1 | L-9 | E-42 |
| 256 | H-1 | L-9 | E-43 |
| 257 | H-1 | L-9 | E-44 |
| 258 | H-1 | L-9 | E-45 |
| 259 | H-1 | L-9 | E-46 |
| 260 | H-1 | L-9 | E-47 |
| 261 | H-1 | L-9 | E-48 |
| 262 | H-1 | L-9 | E-49 |
| 263 | H-1 | L-9 | E-50 |
| 264 | H-1 | L-9 | E-51 |
| 265 | H-1 | L-9 | E-52 |
| 266 | H-1 | L-9 | E-53 |
| 267 | H-1 | L-10 | E-1 |
| 268 | H-1 | L-10 | E-2 |
| 269 | H-1 | L-10 | E-3 |
| 270 | H-1 | L-10 | E-4 |
| 271 | H-1 | L-10 | E-5 |
| 272 | H-1 | L-10 | E-6 |
| 273 | H-1 | L-10 | E-7 |
| 274 | H-1 | L-10 | E-8 |
| 275 | H-1 | L-10 | E-9 |
| 276 | H-1 | L-10 | E-10 |
| 277 | H-1 | L-10 | E-11 |
| 278 | H-1 | L-10 | E-12 |
| 279 | H-1 | L-10 | E-13 |
| 280 | H-1 | L-10 | E-14 |
| 281 | H-1 | L-10 | E-15 |
| 282 | H-1 | L-10 | E-16 |
| 283 | H-1 | L-10 | E-17 |
| 284 | H-1 | L-10 | E-18 |
| 285 | H-1 | L-10 | E-19 |
| 286 | H-1 | L-10 | E-20 |
| 287 | H-1 | L-10 | E-21 |
| 288 | H-1 | L-10 | E-22 |
| 289 | H-1 | L-10 | E-23 |
| 290 | H-1 | L-10 | E-24 |
| 291 | H-1 | L-10 | E-25 |
| 292 | H-1 | L-10 | E-26 |
| 293 | H-1 | L-10 | E-27 |
| 294 | H-1 | L-10 | E-28 |
| 295 | H-1 | L-10 | E-29 |
| 296 | H-1 | L-10 | E-30 |
| 297 | H-1 | L-10 | E-31 |
| 298 | H-1 | L-10 | E-32 |
| 299 | H-1 | L-10 | E-33 |
| 300 | H-1 | L-10 | E-34 |
| 301 | H-1 | L-10 | E-35 |
| 302 | H-1 | L-10 | E-36 |
| 303 | H-1 | L-10 | E-37 |
| 304 | H-1 | L-10 | E-38 |
| 305 | H-1 | L-10 | E-39 |
| 306 | H-1 | L-10 | E-40 |
| 307 | H-1 | L-10 | E-41 |
| 308 | H-1 | L-10 | E-42 |
| 309 | H-1 | L-10 | E-43 |
| 310 | H-1 | L-10 | E-44 |
| 311 | H-1 | L-10 | E-45 |
| 312 | H-1 | L-10 | E-46 |
| 313 | H-1 | L-10 | E-47 |
| 314 | H-1 | L-10 | E-48 |
| 315 | H-1 | L-10 | E-49 |
| 316 | H-1 | L-10 | E-50 |
| 317 | H-1 | L-10 | E-51 |
| 318 | H-1 | L-10 | E-52 |
| 319 | H-1 | L-10 | E-53 |
| 320 | H-1 | L-11 | E-1 |
| 321 | H-1 | L-11 | E-2 |
| 322 | H-1 | L-11 | E-3 |
| 323 | H-1 | L-11 | E-4 |
| 324 | H-1 | L-11 | E-5 |
| 325 | H-1 | L-11 | E-6 |
| 326 | H-1 | L-11 | E-7 |
| 327 | H-1 | L-11 | E-8 |
| 328 | H-1 | L-11 | E-9 |
| 329 | H-1 | L-11 | E-10 |
| 330 | H-1 | L-11 | E-11 |
| 331 | H-1 | L-11 | E-12 |
| 332 | H-1 | L-11 | E-13 |
| 333 | H-1 | L-11 | E-14 |
| 334 | H-1 | L-11 | E-15 |
| 335 | H-1 | L-11 | E-16 |
| 336 | H-1 | L-11 | E-17 |
| 337 | H-1 | L-11 | E-18 |
| 338 | H-1 | L-11 | E-19 |
| 339 | H-1 | L-11 | E-20 |
| 340 | H-1 | L-11 | E-21 |
| 341 | H-1 | L-11 | E-22 |
| 342 | H-1 | L-11 | E-23 |
| 343 | H-1 | L-11 | E-24 |
| 344 | H-1 | L-11 | E-25 |
| 345 | H-1 | L-11 | E-26 |
| 346 | H-1 | L-11 | E-27 |
| 347 | H-1 | L-11 | E-28 |
| 348 | H-1 | L-11 | E-29 |
| 349 | H-1 | L-11 | E-30 |
| 350 | H-1 | L-11 | E-31 |
| 351 | H-1 | L-11 | E-32 |
| 352 | H-1 | L-11 | E-33 |
| 353 | H-1 | L-11 | E-34 |
| 354 | H-1 | L-11 | E-35 |
| 355 | H-1 | L-11 | E-36 |
| 356 | H-1 | L-11 | E-37 |
| 357 | H-1 | L-11 | E-38 |
| 358 | H-1 | L-11 | E-39 |
| 359 | H-1 | L-11 | E-40 |
| 360 | H-1 | L-11 | E-41 |
| 361 | H-1 | L-11 | E-42 |
| 362 | H-1 | L-11 | E-43 |
| 363 | H-1 | L-11 | E-44 |
| 364 | H-1 | L-11 | E-45 |
| 365 | H-1 | L-11 | E-46 |
| 366 | H-1 | L-11 | E-47 |
| 367 | H-1 | L-11 | E-48 |
| 368 | H-1 | L-11 | E-49 |
| 369 | H-1 | L-11 | E-50 |
| 370 | H-1 | L-11 | E-51 |
| 371 | H-1 | L-11 | E-52 |
| 372 | H-1 | L-11 | E-53 |
| 373 | H-1 | L-12 | E-1 |
| 374 | H-1 | L-12 | E-2 |
| 375 | H-1 | L-12 | E-3 |
| 376 | H-1 | L-12 | E-4 |
| 377 | H-1 | L-12 | E-5 |

| Compound No. | H | L | E |
| --- | --- | --- | --- |
| 378 | H-1 | L-12 | E-6 |
| 379 | H-1 | L-12 | E-7 |
| 380 | H-1 | L-12 | E-8 |
| 381 | H-1 | L-12 | E-9 |
| 382 | H-1 | L-12 | E-10 |
| 383 | H-1 | L-12 | E-11 |
| 384 | H-1 | L-12 | E-12 |
| 385 | H-1 | L-12 | E-13 |
| 386 | H-1 | L-12 | E-14 |
| 387 | H-1 | L-12 | E-15 |
| 388 | H-1 | L-12 | E-16 |
| 389 | H-1 | L-12 | E-17 |
| 390 | H-1 | L-12 | E-18 |
| 391 | H-1 | L-12 | E-19 |
| 392 | H-1 | L-12 | E-20 |
| 393 | H-1 | L-12 | E-21 |
| 394 | H-1 | L-12 | E-22 |
| 395 | H-1 | L-12 | E-23 |
| 396 | H-1 | L-12 | E-24 |
| 397 | H-1 | L-12 | E-25 |
| 398 | H-1 | L-12 | E-26 |
| 399 | H-1 | L-12 | E-27 |
| 400 | H-1 | L-12 | E-28 |
| 401 | H-1 | L-12 | E-29 |
| 402 | H-1 | L-12 | E-30 |
| 403 | H-1 | L-12 | E-31 |
| 404 | H-1 | L-12 | E-32 |
| 405 | H-1 | L-12 | E-33 |
| 406 | H-1 | L-12 | E-34 |
| 407 | H-1 | L-12 | E-35 |
| 408 | H-1 | L-12 | E-36 |
| 409 | H-1 | L-12 | E-37 |
| 410 | H-1 | L-12 | E-38 |
| 411 | H-1 | L-12 | E-39 |
| 412 | H-1 | L-12 | E-40 |
| 413 | H-1 | L-12 | E-41 |
| 414 | H-1 | L-12 | E-42 |
| 415 | H-1 | L-12 | E-43 |
| 416 | H-1 | L-12 | E-44 |
| 417 | H-1 | L-12 | E-45 |
| 418 | H-1 | L-12 | E-46 |
| 419 | H-1 | L-12 | E-47 |
| 420 | H-1 | L-12 | E-48 |
| 421 | H-1 | L-12 | E-49 |
| 422 | H-1 | L-12 | E-50 |
| 423 | H-1 | L-12 | E-51 |
| 424 | H-1 | L-12 | E-52 |
| 425 | H-1 | L-12 | E-53 |
| 426 | H-1 | L-14 | E-1 |
| 427 | H-1 | L-14 | E-2 |
| 428 | H-1 | L-14 | E-3 |
| 429 | H-1 | L-14 | E-4 |
| 430 | H-1 | L-14 | E-5 |
| 431 | H-1 | L-14 | E-6 |
| 432 | H-1 | L-14 | E-7 |
| 433 | H-1 | L-14 | E-8 |
| 434 | H-1 | L-14 | E-9 |
| 435 | H-1 | L-14 | E-10 |
| 436 | H-1 | L-14 | E-11 |
| 437 | H-1 | L-14 | E-12 |
| 438 | H-1 | L-14 | E-13 |
| 439 | H-1 | L-14 | E-14 |
| 440 | H-1 | L-14 | E-15 |
| 441 | H-1 | L-14 | E-16 |
| 442 | H-1 | L-14 | E-17 |
| 443 | H-1 | L-14 | E-18 |
| 444 | H-1 | L-14 | E-19 |
| 445 | H-1 | L-14 | E-20 |
| 446 | H-1 | L-14 | E-21 |
| 447 | H-1 | L-14 | E-22 |
| 448 | H-1 | L-14 | E-23 |
| 449 | H-1 | L-14 | E-24 |
| 450 | H-1 | L-14 | E-25 |
| 451 | H-1 | L-14 | E-26 |
| 452 | H-1 | L-14 | E-27 |
| 453 | H-1 | L-14 | E-28 |
| 454 | H-1 | L-14 | E-29 |
| 455 | H-1 | L-14 | E-30 |
| 456 | H-1 | L-14 | E-31 |
| 457 | H-1 | L-14 | E-32 |
| 458 | H-1 | L-14 | E-33 |
| 459 | H-1 | L-14 | E-34 |
| 460 | H-1 | L-14 | E-35 |
| 461 | H-1 | L-14 | E-36 |
| 462 | H-1 | L-14 | E-37 |
| 463 | H-1 | L-14 | E-38 |
| 464 | H-1 | L-14 | E-39 |
| 465 | H-1 | L-14 | E-40 |
| 466 | H-1 | L-14 | E-41 |
| 467 | H-1 | L-14 | E-42 |
| 468 | H-1 | L-14 | E-43 |
| 469 | H-1 | L-14 | E-44 |
| 470 | H-1 | L-14 | E-45 |
| 471 | H-1 | L-14 | E-46 |
| 472 | H-1 | L-14 | E-47 |
| 473 | H-1 | L-14 | E-48 |
| 474 | H-1 | L-14 | E-49 |
| 475 | H-1 | L-14 | E-50 |
| 476 | H-1 | L-14 | E-51 |
| 477 | H-1 | L-14 | E-52 |
| 478 | H-1 | L-14 | E-53 |
| 479 | H-1 | L-13 | E-1 |
| 480 | H-1 | L-13 | E-2 |
| 481 | H-1 | L-13 | E-3 |
| 482 | H-1 | L-13 | E-4 |
| 483 | H-1 | L-13 | E-5 |
| 484 | H-1 | L-13 | E-6 |
| 485 | H-1 | L-13 | E-7 |
| 486 | H-1 | L-13 | E-8 |
| 487 | H-1 | L-13 | E-9 |
| 488 | H-1 | L-13 | E-10 |
| 489 | H-1 | L-13 | E-11 |
| 490 | H-1 | L-13 | E-12 |
| 491 | H-1 | L-13 | E-13 |
| 492 | H-1 | L-13 | E-14 |
| 493 | H-1 | L-13 | E-15 |
| 494 | H-1 | L-13 | E-16 |
| 495 | H-1 | L-13 | E-17 |
| 496 | H-1 | L-13 | E-18 |
| 497 | H-1 | L-13 | E-19 |
| 498 | H-1 | L-13 | E-20 |
| 499 | H-1 | L-13 | E-21 |
| 500 | H-1 | L-13 | E-22 |
| 501 | H-1 | L-13 | E-23 |
| 502 | H-1 | L-13 | E-24 |
| 503 | H-1 | L-13 | E-25 |
| 504 | H-1 | L-13 | E-26 |
| 505 | H-1 | L-13 | E-27 |
| 506 | H-1 | L-13 | E-28 |
| 507 | H-1 | L-13 | E-29 |
| 508 | H-1 | L-13 | E-30 |
| 509 | H-1 | L-13 | E-31 |
| 510 | H-1 | L-13 | E-32 |
| 511 | H-1 | L-13 | E-33 |
| 512 | H-1 | L-13 | E-34 |
| 513 | H-1 | L-13 | E-35 |
| 514 | H-1 | L-13 | E-36 |
| 515 | H-1 | L-13 | E-37 |
| 516 | H-1 | L-13 | E-38 |
| 517 | H-1 | L-13 | E-39 |
| 518 | H-1 | L-13 | E-40 |
| 519 | H-1 | L-13 | E-41 |
| 520 | H-1 | L-13 | E-42 |
| 521 | H-1 | L-13 | E-43 |
| 522 | H-1 | L-13 | E-44 |
| 523 | H-1 | L-13 | E-45 |
| 524 | H-1 | L-13 | E-46 |
| 525 | H-1 | L-13 | E-47 |
| 526 | H-1 | L-13 | E-48 |
| 527 | H-1 | L-13 | E-49 |
| 528 | H-1 | L-13 | E-50 |
| 529 | H-1 | L-13 | E-51 |
| 530 | H-1 | L-13 | E-52 |
| 531 | H-1 | L-13 | E-53 |

-continued

| Compound No. | H | L | E |
|---|---|---|---|
| 532 | H-2 | L-1 | E-1 |
| 533 | H-3 | L-1 | E-1 |
| 534 | H-4 | L-1 | E-1 |
| 535 | H-5 | L-1 | E-1 |
| 536 | H-6 | L-1 | E-1 |
| 537 | H-7 | L-1 | E-1 |
| 538 | H-8 | L-1 | E-1 |
| 539 | H-9 | L-1 | E-1 |
| 540 | H-10 | L-1 | E-1 |
| 541 | H-11 | L-1 | E-1 |
| 542 | H-12 | L-1 | E-1 |
| 543 | H-13 | L-1 | E-1 |
| 544 | H-14 | L-1 | E-1 |
| 545 | H-15 | L-1 | E-1 |
| 546 | H-16 | L-1 | E-1 |
| 547 | H-17 | L-1 | E-1 |
| 548 | H-18 | L-1 | E-1 |
| 549 | H-19 | L-1 | E-1 |
| 550 | H-20 | L-1 | E-1 |
| 551 | H-21 | L-1 | E-1 |
| 552 | H-22 | L-1 | E-1 |
| 553 | H-23 | L-1 | E-1 |
| 554 | H-24 | L-1 | E-1 |
| 555 | H-25 | L-1 | E-1 |
| 556 | H-26 | L-1 | E-1 |
| 557 | H-27 | L-1 | E-1 |
| 558 | H-28 | L-1 | E-1 |
| 559 | H-29 | L-1 | E-1 |
| 560 | H-30 | L-1 | E-1 |
| 561 | H-31 | L-1 | E-1 |
| 562 | H-32 | L-1 | E-1 |
| 563 | H-33 | L-1 | E-1 |
| 564 | H-34 | L-1 | E-1 |
| 565 | H-35 | L-1 | E-1 |
| 566 | H-36 | L-1 | E-1 |
| 567 | H-37 | L-1 | E-1 |
| 568 | H-38 | L-1 | E-1 |
| 569 | H-39 | L-1 | E-1 |
| 570 | H-40 | L-1 | E-1 |
| 571 | H-41 | L-1 | E-1 |
| 572 | H-42 | L-1 | E-1 |
| 573 | H-43 | L-1 | E-1 |
| 574 | H-44 | L-1 | E-1 |
| 575 | H-45 | L-1 | E-1 |
| 576 | H-46 | L-1 | E-1 |
| 577 | H-47 | L-1 | E-1 |
| 578 | H-48 | L-1 | E-1 |
| 579 | H-49 | L-1 | E-1 |
| 580 | H-50 | L-1 | E-1 |
| 581 | H-51 | L-1 | E-1 |
| 582 | H-52 | L-1 | E-1 |
| 583 | H-53 | L-1 | E-1 |
| 584 | H-54 | L-1 | E-1 |
| 585 | H-55 | L-1 | E-1 |
| 586 | H-56 | L-1 | E-1 |
| 587 | H-57 | L-1 | E-1 |
| 588 | H-58 | L-1 | E-1 |
| 589 | H-59 | L-1 | E-1 |
| 590 | H-60 | L-1 | E-1 |
| 591 | H-61 | L-1 | E-1 |
| 592 | H-62 | L-1 | E-1 |
| 593 | H-63 | L-1 | E-1 |
| 594 | H-64 | L-1 | E-1 |
| 595 | H-65 | L-1 | E-1 |
| 596 | H-66 | L-1 | E-1 |
| 597 | H-67 | L-1 | E-1 |
| 598 | H-68 | L-1 | E-1 |
| 599 | H-69 | L-1 | E-1 |
| 600 | H-70 | L-1 | E-1 |
| 601 | H-71 | L-1 | E-1 |
| 602 | H-72 | L-1 | E-1 |
| 603 | H-73 | L-1 | E-1 |
| 604 | H-74 | L-1 | E-1 |
| 605 | H-75 | L-1 | E-1 |
| 606 | H-76 | L-1 | E-1 |
| 607 | H-77 | L-1 | E-1 |
| 608 | H-78 | L-1 | E-1 |
| 609 | H-79 | L-1 | E-1 |
| 610 | H-80 | L-1 | E-1 |
| 611 | H-81 | L-1 | E-1 |
| 612 | H-82 | L-1 | E-1 |
| 613 | H-83 | L-1 | E-1 |
| 614 | H-84 | L-1 | E-1 |
| 615 | H-85 | L-1 | E-1 |
| 616 | H-86 | L-1 | E-1 |
| 617 | H-87 | L-1 | E-1 |
| 618 | H-88 | L-1 | E-1 |
| 619 | H-89 | L-1 | E-1 |
| 620 | H-90 | L-1 | E-1 |
| 621 | H-91 | L-1 | E-1 |
| 622 | H-92 | L-1 | E-1 |
| 623 | H-93 | L-1 | E-1 |
| 624 | H-94 | L-1 | E-1 |
| 625 | H-95 | L-1 | E-1 |
| 626 | H-96 | L-1 | E-1 |
| 627 | H-97 | L-1 | E-1 |
| 628 | H-98 | L-1 | E-1 |
| 629 | H-99 | L-1 | E-1 |
| 630 | H-100 | L-1 | E-1 |
| 631 | H-101 | L-1 | E-1 |
| 632 | H-102 | L-1 | E-1 |
| 633 | H-103 | L-1 | E-1 |
| 634 | H-104 | L-1 | E-1 |
| 635 | H-105 | L-1 | E-1 |
| 636 | H-106 | L-1 | E-1 |
| 637 | H-107 | L-1 | E-1 |
| 638 | H-108 | L-1 | E-1 |
| 639 | H-109 | L-1 | E-1 |
| 640 | H-110 | L-1 | E-1 |
| 641 | H-111 | L-1 | E-1 |
| 642 | H-112 | L-1 | E-1 |
| 643 | H-113 | L-1 | E-1 |
| 644 | H-114 | L-1 | E-1 |
| 645 | H-115 | L-1 | E-1 |
| 646 | H-116 | L-1 | E-1 |
| 647 | H-117 | L-1 | E-1 |
| 648 | H-118 | L-1 | E-1 |
| 649 | H-119 | L-1 | E-1 |
| 650 | H-120 | L-1 | E-1 |
| 651 | H-121 | L-1 | E-1 |
| 652 | H-122 | L-1 | E-1 |
| 653 | H-123 | L-1 | E-1 |
| 654 | H-124 | L-1 | E-1 |
| 655 | H-125 | L-1 | E-1 |
| 656 | H-126 | L-1 | E-1 |
| 657 | H-127 | L-1 | E-1 |
| 658 | H-128 | L-1 | E-1 |
| 659 | H-129 | L-1 | E-1 |
| 660 | H-130 | L-1 | E-1 |
| 661 | H-131 | L-1 | E-1 |
| 662 | H-132 | L-1 | E-1 |
| 663 | H-133 | L-1 | E-1 |
| 664 | H-134 | L-1 | E-1 |
| 665 | H-135 | L-1 | E-1 |
| 666 | H-136 | L-1 | E-1 |
| 667 | H-137 | L-1 | E-1 |
| 668 | H-138 | L-1 | E-1 |
| 669 | H-139 | L-1 | E-1 |
| 670 | H-2 | L-4 | E-1 |
| 671 | H-3 | L-4 | E-1 |
| 672 | H-4 | L-4 | E-1 |
| 673 | H-5 | L-4 | E-1 |
| 674 | H-6 | L-4 | E-1 |
| 675 | H-7 | L-4 | E-1 |
| 676 | H-8 | L-4 | E-1 |
| 677 | H-9 | L-4 | E-1 |
| 678 | H-10 | L-4 | E-1 |
| 679 | H-11 | L-4 | E-1 |
| 680 | H-12 | L-4 | E-1 |
| 681 | H-13 | L-4 | E-1 |
| 682 | H-14 | L-4 | E-1 |
| 683 | H-15 | L-4 | E-1 |
| 684 | H-16 | L-4 | E-1 |
| 685 | H-17 | L-4 | E-1 |

| Compound No. | H | L | E |
|---|---|---|---|
| 686 | H-18 | L-4 | E-1 |
| 687 | H-19 | L-4 | E-1 |
| 688 | H-20 | L-4 | E-1 |
| 689 | H-21 | L-4 | E-1 |
| 690 | H-22 | L-4 | E-1 |
| 691 | H-23 | L-4 | E-1 |
| 692 | H-24 | L-4 | E-1 |
| 693 | H-25 | L-4 | E-1 |
| 694 | H-26 | L-4 | E-1 |
| 695 | H-27 | L-4 | E-1 |
| 696 | H-28 | L-4 | E-1 |
| 697 | H-29 | L-4 | E-1 |
| 698 | H-30 | L-4 | E-1 |
| 699 | H-31 | L-4 | E-1 |
| 700 | H-32 | L-4 | E-1 |
| 701 | H-33 | L-4 | E-1 |
| 702 | H-34 | L-4 | E-1 |
| 703 | H-35 | L-4 | E-1 |
| 704 | H-36 | L-4 | E-1 |
| 705 | H-37 | L-4 | E-1 |
| 706 | H-38 | L-4 | E-1 |
| 707 | H-39 | L-4 | E-1 |
| 708 | H-40 | L-4 | E-1 |
| 709 | H-41 | L-4 | E-1 |
| 710 | H-42 | L-4 | E-1 |
| 711 | H-43 | L-4 | E-1 |
| 712 | H-44 | L-4 | E-1 |
| 713 | H-45 | L-4 | E-1 |
| 714 | H-46 | L-4 | E-1 |
| 715 | H-47 | L-4 | E-1 |
| 716 | H-48 | L-4 | E-1 |
| 717 | H-49 | L-4 | E-1 |
| 718 | H-50 | L-4 | E-1 |
| 719 | H-51 | L-4 | E-1 |
| 720 | H-52 | L-4 | E-1 |
| 721 | H-53 | L-4 | E-1 |
| 722 | H-54 | L-4 | E-1 |
| 723 | H-55 | L-4 | E-1 |
| 724 | H-56 | L-4 | E-1 |
| 725 | H-57 | L-4 | E-1 |
| 726 | H-58 | L-4 | E-1 |
| 727 | H-59 | L-4 | E-1 |
| 728 | H-60 | L-4 | E-1 |
| 729 | H-61 | L-4 | E-1 |
| 730 | H-62 | L-4 | E-1 |
| 731 | H-63 | L-4 | E-1 |
| 732 | H-64 | L-4 | E-1 |
| 733 | H-65 | L-4 | E-1 |
| 734 | H-66 | L-4 | E-1 |
| 735 | H-67 | L-4 | E-1 |
| 736 | H-68 | L-4 | E-1 |
| 737 | H-69 | L-4 | E-1 |
| 738 | H-70 | L-4 | E-1 |
| 739 | H-71 | L-4 | E-1 |
| 740 | H-72 | L-4 | E-1 |
| 741 | H-73 | L-4 | E-1 |
| 742 | H-74 | L-4 | E-1 |
| 743 | H-75 | L-4 | E-1 |
| 744 | H-76 | L-4 | E-1 |
| 745 | H-77 | L-4 | E-1 |
| 746 | H-78 | L-4 | E-1 |
| 747 | H-79 | L-4 | E-1 |
| 748 | H-80 | L-4 | E-1 |
| 749 | H-81 | L-4 | E-1 |
| 750 | H-82 | L-4 | E-1 |
| 751 | H-83 | L-4 | E-1 |
| 752 | H-84 | L-4 | E-1 |
| 753 | H-85 | L-4 | E-1 |
| 754 | H-86 | L-4 | E-1 |
| 755 | H-87 | L-4 | E-1 |
| 756 | H-88 | L-4 | E-1 |
| 757 | H-89 | L-4 | E-1 |
| 758 | H-90 | L-4 | E-1 |
| 759 | H-91 | L-4 | E-1 |
| 760 | H-92 | L-4 | E-1 |
| 761 | H-93 | L-4 | E-1 |
| 762 | H-94 | L-4 | E-1 |
| 763 | H-95 | L-4 | E-1 |
| 764 | H-96 | L-4 | E-1 |
| 765 | H-97 | L-4 | E-1 |
| 766 | H-98 | L-4 | E-1 |
| 767 | H-99 | L-4 | E-1 |
| 768 | H-100 | L-4 | E-1 |
| 769 | H-101 | L-4 | E-1 |
| 770 | H-102 | L-4 | E-1 |
| 771 | H-103 | L-4 | E-1 |
| 772 | H-104 | L-4 | E-1 |
| 773 | H-105 | L-4 | E-1 |
| 774 | H-106 | L-4 | E-1 |
| 775 | H-107 | L-4 | E-1 |
| 776 | H-108 | L-4 | E-1 |
| 777 | H-109 | L-4 | E-1 |
| 778 | H-110 | L-4 | E-1 |
| 779 | H-111 | L-4 | E-1 |
| 780 | H-112 | L-4 | E-1 |
| 781 | H-113 | L-4 | E-1 |
| 782 | H-114 | L-4 | E-1 |
| 783 | H-115 | L-4 | E-1 |
| 784 | H-116 | L-4 | E-1 |
| 785 | H-117 | L-4 | E-1 |
| 786 | H-118 | L-4 | E-1 |
| 787 | H-119 | L-4 | E-1 |
| 788 | H-120 | L-4 | E-1 |
| 789 | H-121 | L-4 | E-1 |
| 790 | H-122 | L-4 | E-1 |
| 791 | H-123 | L-4 | E-1 |
| 792 | H-124 | L-4 | E-1 |
| 793 | H-125 | L-4 | E-1 |
| 794 | H-126 | L-4 | E-1 |
| 795 | H-127 | L-4 | E-1 |
| 796 | H-128 | L-4 | E-1 |
| 797 | H-129 | L-4 | E-1 |
| 798 | H-130 | L-4 | E-1 |
| 799 | H-131 | L-4 | E-1 |
| 800 | H-132 | L-4 | E-1 |
| 801 | H-133 | L-4 | E-1 |
| 802 | H-134 | L-4 | E-1 |
| 803 | H-135 | L-4 | E-1 |
| 804 | H-136 | L-4 | E-1 |
| 805 | H-137 | L-4 | E-1 |
| 806 | H-138 | L-4 | E-1 |
| 807 | H-139 | L-4 | E-1 |
| 808 | H-2 | L-1 | E-3 |
| 809 | H-3 | L-1 | E-3 |
| 810 | H-4 | L-1 | E-3 |
| 811 | H-5 | L-1 | E-3 |
| 812 | H-6 | L-1 | E-3 |
| 813 | H-7 | L-1 | E-3 |
| 814 | H-8 | L-1 | E-3 |
| 815 | H-9 | L-1 | E-3 |
| 816 | H-10 | L-1 | E-3 |
| 817 | H-11 | L-1 | E-3 |
| 818 | H-12 | L-1 | E-3 |
| 819 | H-13 | L-1 | E-3 |
| 820 | H-14 | L-1 | E-3 |
| 821 | H-15 | L-1 | E-3 |
| 822 | H-16 | L-1 | E-3 |
| 823 | H-17 | L-1 | E-3 |
| 824 | H-18 | L-1 | E-3 |
| 825 | H-19 | L-1 | E-3 |
| 826 | H-20 | L-1 | E-3 |
| 827 | H-21 | L-1 | E-3 |
| 828 | H-22 | L-1 | E-3 |
| 829 | H-23 | L-1 | E-3 |
| 830 | H-24 | L-1 | E-3 |
| 831 | H-25 | L-1 | E-3 |
| 832 | H-26 | L-1 | E-3 |
| 833 | H-27 | L-1 | E-3 |
| 834 | H-28 | L-1 | E-3 |
| 835 | H-29 | L-1 | E-3 |
| 836 | H-30 | L-1 | E-3 |
| 837 | H-31 | L-1 | E-3 |
| 838 | H-32 | L-1 | E-3 |
| 839 | H-33 | L-1 | E-3 |

-continued

| Compound No. | H | L | E |
|---|---|---|---|
| 840 | H-34 | L-1 | E-3 |
| 841 | H-35 | L-1 | E-3 |
| 842 | H-36 | L-1 | E-3 |
| 843 | H-37 | L-1 | E-3 |
| 844 | H-38 | L-1 | E-3 |
| 845 | H-39 | L-1 | E-3 |
| 846 | H-40 | L-1 | E-3 |
| 847 | H-41 | L-1 | E-3 |
| 848 | H-42 | L-1 | E-3 |
| 849 | H-43 | L-1 | E-3 |
| 850 | H-44 | L-1 | E-3 |
| 851 | H-45 | L-1 | E-3 |
| 852 | H-46 | L-1 | E-3 |
| 853 | H-47 | L-1 | E-3 |
| 854 | H-48 | L-1 | E-3 |
| 855 | H-49 | L-1 | E-3 |
| 856 | H-50 | L-1 | E-3 |
| 857 | H-51 | L-1 | E-3 |
| 858 | H-52 | L-1 | E-3 |
| 859 | H-53 | L-1 | E-3 |
| 860 | H-54 | L-1 | E-3 |
| 861 | H-55 | L-1 | E-3 |
| 862 | H-56 | L-1 | E-3 |
| 863 | H-57 | L-1 | E-3 |
| 864 | H-58 | L-1 | E-3 |
| 865 | H-59 | L-1 | E-3 |
| 866 | H-60 | L-1 | E-3 |
| 867 | H-61 | L-1 | E-3 |
| 868 | H-62 | L-1 | E-3 |
| 869 | H-63 | L-1 | E-3 |
| 870 | H-64 | L-1 | E-3 |
| 871 | H-65 | L-1 | E-3 |
| 872 | H-66 | L-1 | E-3 |
| 873 | H-67 | L-1 | E-3 |
| 874 | H-68 | L-1 | E-3 |
| 875 | H-69 | L-1 | E-3 |
| 876 | H-70 | L-1 | E-3 |
| 877 | H-71 | L-1 | E-3 |
| 878 | H-72 | L-1 | E-3 |
| 879 | H-73 | L-1 | E-3 |
| 880 | H-74 | L-1 | E-3 |
| 881 | H-75 | L-1 | E-3 |
| 882 | H-76 | L-1 | E-3 |
| 883 | H-77 | L-1 | E-3 |
| 884 | H-78 | L-1 | E-3 |
| 885 | H-79 | L-1 | E-3 |
| 886 | H-80 | L-1 | E-3 |
| 887 | H-81 | L-1 | E-3 |
| 888 | H-82 | L-1 | E-3 |
| 889 | H-83 | L-1 | E-3 |
| 890 | H-84 | L-1 | E-3 |
| 891 | H-85 | L-1 | E-3 |
| 892 | H-86 | L-1 | E-3 |
| 893 | H-87 | L-1 | E-3 |
| 894 | H-88 | L-1 | E-3 |
| 895 | H-89 | L-1 | E-3 |
| 896 | H-90 | L-1 | E-3 |
| 897 | H-91 | L-1 | E-3 |
| 898 | H-92 | L-1 | E-3 |
| 899 | H-93 | L-1 | E-3 |
| 900 | H-94 | L-1 | E-3 |
| 901 | H-95 | L-1 | E-3 |
| 902 | H-96 | L-1 | E-3 |
| 903 | H-97 | L-1 | E-3 |
| 904 | H-98 | L-1 | E-3 |
| 905 | H-99 | L-1 | E-3 |
| 906 | H-100 | L-1 | E-3 |
| 907 | H-101 | L-1 | E-3 |
| 908 | H-102 | L-1 | E-3 |
| 909 | H-103 | L-1 | E-3 |
| 910 | H-104 | L-1 | E-3 |
| 911 | H-105 | L-1 | E-3 |
| 912 | H-106 | L-1 | E-3 |
| 913 | H-107 | L-1 | E-3 |
| 914 | H-108 | L-1 | E-3 |
| 915 | H-109 | L-1 | E-3 |
| 916 | H-110 | L-1 | E-3 |
| 917 | H-111 | L-1 | E-3 |
| 918 | H-112 | L-1 | E-3 |
| 919 | H-113 | L-1 | E-3 |
| 920 | H-114 | L-1 | E-3 |
| 921 | H-115 | L-1 | E-3 |
| 922 | H-116 | L-1 | E-3 |
| 923 | H-117 | L-1 | E-3 |
| 924 | H-118 | L-1 | E-3 |
| 925 | H-119 | L-1 | E-3 |
| 926 | H-120 | L-1 | E-3 |
| 927 | H-121 | L-1 | E-3 |
| 928 | H-122 | L-1 | E-3 |
| 929 | H-123 | L-1 | E-3 |
| 930 | H-124 | L-1 | E-3 |
| 931 | H-125 | L-1 | E-3 |
| 932 | H-126 | L-1 | E-3 |
| 933 | H-127 | L-1 | E-3 |
| 934 | H-128 | L-1 | E-3 |
| 935 | H-129 | L-1 | E-3 |
| 936 | H-130 | L-1 | E-3 |
| 937 | H-131 | L-1 | E-3 |
| 938 | H-132 | L-1 | E-3 |
| 939 | H-133 | L-1 | E-3 |
| 940 | H-134 | L-1 | E-3 |
| 941 | H-135 | L-1 | E-3 |
| 942 | H-136 | L-1 | E-3 |
| 943 | H-137 | L-1 | E-3 |
| 944 | H-138 | L-1 | E-3 |
| 945 | H-139 | L-1 | E-3 |
| 946 | H-2 | L-1 | E-10 |
| 947 | H-3 | L-1 | E-10 |
| 948 | H-4 | L-1 | E-10 |
| 949 | H-5 | L-1 | E-10 |
| 950 | H-6 | L-1 | E-10 |
| 951 | H-7 | L-1 | E-10 |
| 952 | H-8 | L-1 | E-10 |
| 953 | H-9 | L-1 | E-10 |
| 954 | H-10 | L-1 | E-10 |
| 955 | H-11 | L-1 | E-10 |
| 956 | H-12 | L-1 | E-10 |
| 957 | H-13 | L-1 | E-10 |
| 958 | H-14 | L-1 | E-10 |
| 959 | H-15 | L-1 | E-10 |
| 960 | H-16 | L-1 | E-10 |
| 961 | H-17 | L-1 | E-10 |
| 962 | H-18 | L-1 | E-10 |
| 963 | H-19 | L-1 | E-10 |
| 964 | H-20 | L-1 | E-10 |
| 965 | H-21 | L-1 | E-10 |
| 966 | H-22 | L-1 | E-10 |
| 967 | H-23 | L-1 | E-10 |
| 968 | H-24 | L-1 | E-10 |
| 969 | H-25 | L-1 | E-10 |
| 970 | H-26 | L-1 | E-10 |
| 971 | H-27 | L-1 | E-10 |
| 972 | H-28 | L-1 | E-10 |
| 973 | H-29 | L-1 | E-10 |
| 974 | H-30 | L-1 | E-10 |
| 975 | H-31 | L-1 | E-10 |
| 976 | H-32 | L-1 | E-10 |
| 977 | H-33 | L-1 | E-10 |
| 978 | H-34 | L-1 | E-10 |
| 979 | H-35 | L-1 | E-10 |
| 980 | H-36 | L-1 | E-10 |
| 981 | H-37 | L-1 | E-10 |
| 982 | H-38 | L-1 | E-10 |
| 983 | H-39 | L-1 | E-10 |
| 984 | H-40 | L-1 | E-10 |
| 985 | H-41 | L-1 | E-10 |
| 986 | H-42 | L-1 | E-10 |
| 987 | H-43 | L-1 | E-10 |
| 988 | H-44 | L-1 | E-10 |
| 989 | H-45 | L-1 | E-10 |
| 990 | H-46 | L-1 | E-10 |
| 991 | H-47 | L-1 | E-10 |
| 992 | H-48 | L-1 | E-10 |
| 993 | H-49 | L-1 | E-10 |

-continued

| Compound No. | H | L | E |
|---|---|---|---|
| 994 | H-50 | L-1 | E-10 |
| 995 | H-51 | L-1 | E-10 |
| 996 | H-52 | L-1 | E-10 |
| 997 | H-53 | L-1 | E-10 |
| 998 | H-54 | L-1 | E-10 |
| 999 | H-55 | L-1 | E-10 |
| 1000 | H-56 | L-1 | E-10 | wherein, optionally, hydrogens in Compound 1 to Compound 625, Compound 632 to Compound 640, Compound 651, Compound 653 to Compound 763, Compound 770 to Compound 778, Compound 789, Compound 791 to Compound 901, Compound 908 to Compound 916, Compound 927, Compound 929 to Compound 1000 can be partially or completely substituted with deuterium.

12. A compound formulation, comprising the compound according to claim 1.

13. An electroluminescent device, comprising:
an anode,
a cathode, and
an organic layer disposed between the anode and the cathode, wherein the organic layer comprises a compound according to claim 1.

14. The compound according to claim 4, wherein at least one of R and $R_x$ is selected from deuterium, phenyl, biphenyl, or pyridyl.

15. The compound according to claim 7, wherein $Z_1$ to $Z_3$ are each N.

16. The compound according to claim 7, wherein Ar is, at each occurrence identically or differently, selected from the group consisting of: phenyl, deuterated phenyl, methylphenyl, fluorophenyl, tert-butylphenyl, trideuteratedmethyl phenyl, biphenyl, naphthyl, deuterated naphthyl, dibenzofuranyl, dibenzothienyl, 9,9-dimethylfluorenyl, carbazolyl, pyridyl, pyrimidinyl, 4-cyanophenyl, 3-cyanophenyl, triphenylene, and combinations thereof.

17. The compound according to claim 9, wherein, the ring D is, at each occurrence identically or differently, selected from a benzene ring, a naphthalene ring, a phenanthrene ring, a fluorene ring, a triphenylene ring, a carbazole ring, a dibenzofuran ring, a dibenzothiophene ring, a pyridine ring, and combinations thereof;
$L_1$ is selected from a single bond, substituted or unsubstituted phenylene, or substituted or unsubstituted naphthylene;
$R_n$ and $R_m$ are, at each occurrence identically or differently, selected from the group consisting of: hydrogen, deuterium, halogen, substituted or unsubstituted alkyl having 1 to 20 carbon atoms, substituted or unsubstituted arylalkyl having 7 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, a hydroxyl group, a sulfanyl group, and combinations thereof.

18. The compound according to claim 9, wherein $L_1$ is selected from a single bond.

19. A display assembly, comprising the organic electroluminescent device according to claim 13.

20. The device according to claim 13, wherein the organic layer is an emissive layer, and the compound is a host material.

21. The electroluminescent device according to claim 20, wherein the emissive layer further comprises at least one phosphorescent material.

22. The electroluminescent device according to claim 21, wherein the phosphorescent material is a metal complex, and the metal complex has a general formula of $M(L_a)_m(L_b)_n(L_c)_q$;
M is selected from a metal with a relative atomic mass greater than 40;
$L_a$, $L_b$, and $L_c$ are a first ligand, a second ligand, and a third ligand coordinated to the metal M, respectively; $L_a$, $L_b$, and $L_c$ can be optionally joined to form a multidentate ligand;
$L_a$, $L_b$, and $L_c$ can be the same or different; m is 1, 2, or 3; n is 0, 1, or 2; q is 0 or 1; the sum of m, n, and q equals to the oxidation state of M; when m is greater than or equal to 2, the plurality of $L_a$ can be the same or different; and when n is equal to 2, two $L_b$ can be the same or different;
$L_a$ has a structure represented by Formula 4:

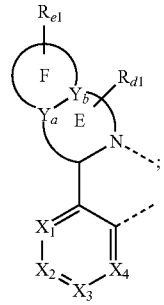

Formula 4 wherein,
the ring E is selected from a five-membered heteroaromatic ring or a six-membered heteroaromatic ring;
the ring F is selected from a five-membered unsaturated carbocyclic ring, a benzene ring, a five-membered heteroaromatic ring, or a six-membered heteroaromatic ring;
the ring E and the ring F are fused via $Y_a$ and $Y_b$;
$Y_a$ and $Y_b$ are, at each occurrence identically or differently, selected from C or N;
$R_{d1}$ and $R_{e1}$ represent, at each occurrence identically or differently, mono-substitution, multiple substitutions, or non-substitution;
$X_1$ to $X_4$ are, at each occurrence identically or differently, selected from $CR_{xx}$ or N;
$R_{d1}$, $R_{e1}$, and $R_{xx}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents $R_{d1}$, $R_{e1}$, $R_{xx}$ can be optionally joined to form a ring;

$L_b$ and $L_c$ are each independently selected from any one of the following structures:

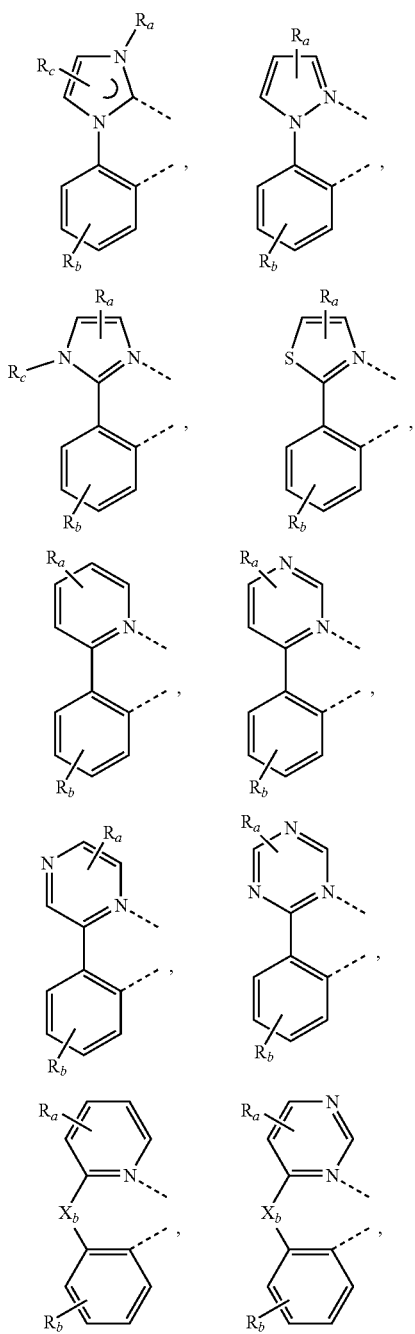

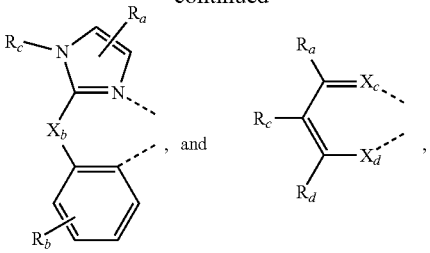

wherein, $R_a$, $R_b$, and $R_c$ are, at each occurrence identically or differently, represent mono-substitution, multi-substitution, or non-substitution;

$X_b$ is, at each occurrence identically or differently, selected from the group consisting of: O, S, Se, $NR_{N1}$, and $CR_{C1}R_{C2}$;

$X_c$ and $X_d$ are, at each occurrence identically or differently, selected from the group consisting of: O, S, Se, and $NR_{N2}$;

$R_a$, $R_b$, $R_c$, $R_{N1}$, $R_{N2}$, $R_{C1}$, and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

in structures of the ligands $L_b$ and $L_c$, adjacent substituents $R_a$, $R_b$, $R_c$, $R_{N1}$, $R_{N2}$, $R_{C1}$, and $R_{C2}$ can be optionally joined to form a ring.

23. The electroluminescent device according to claim 22, wherein the ligand $L_b$ has the following structure:

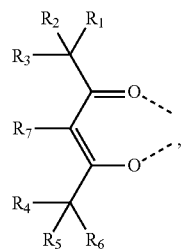

wherein $R_1$ to $R_7$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

24. The electroluminescent device according to claim 22, wherein the phosphorescent material is an Ir complex, a Pt complex or an Os complex.

25. The electroluminescent device according to claim 22, wherein the phosphorescent material is an Ir complex and has a structure represented by any one of: $Ir(L_a)(L_b)(L_c)$, $Ir(L_a)_2(L_b)$, $Ir(L_a)_2(L_c)$, or $Ir(L_a)(L_c)_2$.

* * * * *